(12) United States Patent
Iyidogan et al.

(10) Patent No.: US 11,203,779 B2
(45) Date of Patent: *Dec. 21, 2021

(54) SEQUENCING METHOD FOR RAPID IDENTIFICATION AND PROCESSING OF COGNATE NUCLEOTIDE PAIRS

(71) Applicant: Omniome, Inc., San Diego, CA (US)

(72) Inventors: Pinar Iyidogan, San Diego, CA (US); Kandaswamy Vijayan, San Diego, CA (US)

(73) Assignee: OMNIONIE, INC., San Diego, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 16/540,825

(22) Filed: Aug. 14, 2019

(65) Prior Publication Data

US 2019/0367967 A1 Dec. 5, 2019

Related U.S. Application Data

(63) Continuation of application No. 15/654,406, filed on Jul. 19, 2017, now Pat. No. 10,428,378.

(60) Provisional application No. 62/375,389, filed on Aug. 15, 2016.

(51) Int. Cl.
| | |
|---|---|
| *C12Q 1/686* | (2018.01) |
| *C12Q 1/6869* | (2018.01) |
| *C12Q 1/6806* | (2018.01) |
| *C12Q 1/6813* | (2018.01) |
| *C12Q 1/6853* | (2018.01) |
| *G01N 27/447* | (2006.01) |
| *C12Q 1/00* | (2006.01) |
| *G01N 21/45* | (2006.01) |
| *G01N 1/40* | (2006.01) |

(52) U.S. Cl.
CPC .......... *C12Q 1/686* (2013.01); *C12Q 1/6806* (2013.01); *C12Q 1/6813* (2013.01); *C12Q 1/6853* (2013.01); *C12Q 1/6869* (2013.01); *G01N 21/45* (2013.01); *G01N 27/447* (2013.01); *C12Q 1/00* (2013.01); *G01N 2001/4038* (2013.01)

(58) Field of Classification Search
CPC .... C12Q 1/686; C12Q 1/6869; C12Q 1/6806; C12Q 1/6813; C12Q 1/6853; C12Q 1/00; G01N 21/45; G01N 27/447; G01N 2001/4038
See application file for complete search history.

(56) References Cited

U.S. PATENT DOCUMENTS

| | | |
|---|---|---|
| 5,302,509 A | 4/1994 | Cheeseman |
| 5,614,365 A | 3/1997 | Tabor et al. |
| 6,485,909 B1 | 11/2002 | Hong et al. |
| 6,720,177 B2 | 4/2004 | Ghadiri et al. |
| 6,828,094 B2 | 12/2004 | Kilger et al. |
| 6,908,736 B1 | 6/2005 | Densham |
| 7,008,766 B1 | 3/2006 | Densham et al. |
| 7,057,026 B2 | 6/2006 | Barnes et al. |
| 7,223,540 B2 | 5/2007 | Pourmand et al. |
| 7,264,934 B2 | 9/2007 | Fuller et al. |
| 7,329,492 B2 | 2/2008 | Hardin et al. |
| 7,414,116 B2 | 8/2008 | Liu et al. |
| 7,427,673 B2 | 9/2008 | Balasubramanian et al. |
| 7,449,297 B2 | 11/2008 | Freije et al. |
| 7,482,120 B2 | 1/2009 | Buzby et al. |
| 7,544,794 B1 | 6/2009 | Benner et al. |
| 7,604,963 B2 | 10/2009 | Densham et al. |
| 7,635,578 B2 | 12/2009 | Li et al. |
| 7,713,698 B2 | 5/2010 | Li et al. |
| 7,871,771 B2 | 1/2011 | Fuller et al. |
| 7,939,264 B1 | 5/2011 | Densham et al. |
| 7,956,171 B2 | 6/2011 | Siddiqi et al. |
| 8,034,923 B1 | 10/2011 | Benner et al. |
| 8,071,755 B2 | 12/2011 | Efcavitch et al. |
| 8,133,672 B2 | 3/2012 | Bjornson et al. |
| 8,236,532 B2 | 8/2012 | Eltoukhy et al. |
| 8,298,792 B2 | 10/2012 | Meng et al. |
| 8,399,196 B2 | 3/2013 | Hoser et al. |
| 8,481,266 B2 | 7/2013 | Shao et al. |
| 8,535,881 B2 | 9/2013 | Schneider et al. |

(Continued)

FOREIGN PATENT DOCUMENTS

| | | |
|---|---|---|
| EP | 1115848 | 7/2001 |
| WO | 1990/013666 | 11/1990 |

(Continued)

OTHER PUBLICATIONS

"International Search Report and Written Opinion", PCT Application No. PCT/US2017/067976, Mar. 14, 2018, 13 pages.

Agnarsson et al., "On-Chip modulation of evanescent illumination and live-cell imaging with polymer waveguides", Optics Express, Nov. 7, 2011, vol. 19, No. 23, p. 22929-22935.

Anker et al., "Biosensing with Plasmonic Nanosensors", Nature Materials 7, No. 6, Jun. 2008, 442-453.

Bandwar et al., "Peculiar 2-Aminopurine Fluorescence Monitors the Dynamics of Open Complex Formation by Bacteriophage T7 RNA Polymerase", The Journal of Biological Chemistry, vol. 275, No. 17, 2001, 14075-14082.

Brockman et al., "A Multistep Chemical Modification Procedure to Create DNA Arrays on Gold Surfaces for the Study of Protein—DNA Interactions with Surface Plasmon Resonance Imaging", Journal of the American Chemical Society 121, Sep. 1999, 8044-8051.

(Continued)

*Primary Examiner* — Cynthia B Wilder

(74) *Attorney, Agent, or Firm* — Kilpatrick Townsend & Stockton LLP

(57) ABSTRACT

Provided are methods and systems for reducing the time needed for sequencing nucleic acids. The approach relies on detecting formation of nucleotide-specific ternary complexes comprising a polymerase (e.g., a DNA polymerizing enzyme), a primed template nucleic acid molecule, and a nucleotide complementary to the templated base of the primed template nucleic acid. The methods and systems facilitate determination of the next correct nucleotide, as well as the subsequent next correct nucleotide from a cycle of examining four different nucleotides without requiring chemical incorporation of any nucleotide into the primer.

16 Claims, 7 Drawing Sheets

(56) References Cited

U.S. PATENT DOCUMENTS

| | | | |
|---|---|---|---|
| 8,603,741 | B2 | 12/2013 | Emig et al. |
| 8,632,975 | B2 | 1/2014 | Vander Horn et al. |
| 8,703,461 | B2 | 4/2014 | Peris et al. |
| 8,808,989 | B1 | 8/2014 | Siddiqi et al. |
| 8,911,972 | B2 | 12/2014 | Chaisson et al. |
| 8,986,930 | B2 | 3/2015 | Fedorov et al. |
| 9,279,154 | B2 | 6/2016 | Previte et al. |
| 9,399,798 | B2 | 7/2016 | Morris et al. |
| 2006/0051807 | A1 | 3/2006 | Fuller |
| 2006/0292583 | A1 | 12/2006 | Schneider et al. |
| 2007/0009925 | A1 | 1/2007 | Fang et al. |
| 2009/0061447 | A1 | 3/2009 | Schneider |
| 2010/0316999 | A1 | 12/2010 | Densham |
| 2010/0317012 | A1 | 12/2010 | Ju et al. |
| 2010/0330570 | A1* | 12/2010 | Vander Horn ........... C12Q 1/68 435/6.11 |
| 2011/0008794 | A1 | 1/2011 | Schneider |
| 2011/0160077 | A1 | 6/2011 | Chaisson et al. |
| 2011/0237464 | A1 | 9/2011 | Cunningham et al. |
| 2014/0127680 | A1 | 5/2014 | Emig et al. |
| 2014/0234940 | A1 | 8/2014 | Peris et al. |
| 2016/0010150 | A1 | 1/2016 | Emig et al. |
| 2017/0022553 | A1 | 1/2017 | Vijayan et al. |
| 2017/0292157 | A1 | 10/2017 | Drmanac |
| 2017/0314064 | A1 | 11/2017 | Iyidogan et al. |
| 2018/0044715 | A1 | 2/2018 | Iyidogan et al. |

FOREIGN PATENT DOCUMENTS

| | | |
|---|---|---|
| WO | 91006678 | 5/1991 |
| WO | 9506138 | 3/1995 |
| WO | 2001/016375 | 3/2001 |
| WO | 2002/04680 | 1/2002 |
| WO | 2005/121363 | 12/2005 |
| WO | 2009061911 | 5/2009 |
| WO | WO 2009061911 * | 5/2009 |
| WO | 2009145820 | 12/2009 |
| WO | 2010/068884 | 6/2010 |
| WO | 2010/111690 | 9/2010 |
| WO | 2010141390 | 12/2010 |
| WO | 2007123744 | 11/2011 |
| WO | 2011/159942 | 12/2011 |
| WO | 2012/166742 | 12/2012 |
| WO | 2013/096692 | 6/2013 |
| WO | 2014114665 | 7/2014 |
| WO | 2016071689 | 5/2016 |
| WO | 2017014762 | 1/2017 |
| WO | 2017117235 | 1/2017 |
| WO | 2007048033 | 4/2017 |
| WO | 2017184996 | 10/2017 |
| WO | 2018034780 | 2/2018 |

OTHER PUBLICATIONS

Brown et al., "Pre-Steady-State Kinetic Analysis of Truncated and Full-Length Saccharomyces cerevisiae DNA Polymerase Eta", Journal of Nucleic Acids, 2010, Article ID 871939, 11 pages.

Campagnola et al., "High-throughput Screening Identification of Poliovirus RNA-dependent RNA Polymerase Inhibitors", Antiviral Res., Sep. 2011, vol. 91, No. 3, pp. 241-251.

Chan et al., "A general method for discovering inhibitors of protein-DNA interactions using photonic crystal biosensors", ACS Chem Biol, vol. 3, No. 7, Jul. 18, 2008, pp. 437-448.

Chen et al., "The History and Advances of Reversible Termintors Used in New Generations of Sequencing Technology", Genomics Proteomics Bioinformatics, 11(1), Feb. 1, 2013, pp. 34-40.

Chin et al., "The Effect of Divalent Nickel (Ni2+) on in Vivo DNA Replication by DNA Polymerase α1", Cancer Research, May 1, 1994, pp. 2337-2341.

Concepcion, "Label-Free Detection of Biomolecular Interactions Using BioLayer Interferometry for Kinetic Characterization", Combinatorial Chemistry and High Throughput Screening, vol. 12, No. 8, 2009, pp. 791-800.

Crumpacker, "Mechanism of action of foscarnet against viral polymerase", American Journal of Medicine, vol. 92, Issue 2, Supplement 1, Feb. 14, 1992, pp. S3-S7.

Datta, "Salt Dependence of DNA binding by Thermus aquaticus and Escherichia coli DNA Polymerases", Journal of Biological Chemistry, vol. 278, Issue of Feb. 21, 2003, pp. 5694-5701.

Deredge et al., "The Glutamate Effect on DNA Binding by Pol I DNA Polymerases: Osmotic Stress and the Effective Reversal of Salt Linkage", J. Mol. Biol., vol. 401, 2010, pp. 223-238.

Doublie et al., "An open and closed case for all polymerases", Structure, 7, Feb. 1999, pp. R31-R35.

Dunlap, "Use of 2-Aminopurine and Tryptophan Fluorescence as Probes in Kinetic Analyses of DNA Polymerase Beta", Biochemistry, 41, 2002, p. 11226-11235.

Dzantiev et al., "A conformational change in E. coli DNA polymerase I (Klenow fragment) is induced in the presence of a dNTP complementary to the template base in the active site", Biochemistry, vol. 39, No. 2, 2000, pp. 356-361.

Eriksson et al., "Pyrophosphate analogues as inhibitors of DNA polymerases of cytomegalovirus, herpes simplex virus and cellular origin", Biochimica et Biophysica Acta, vol. 696, No. 2, 1982, pp. 115-123.

Escobedo et al., "Integrated nanohole array surface plasmon resonance sensing device using a dual-wavelength source", Nov. 1, 2011, J. Micromech. Microeng., 21: 115001, 1-6.

Espinoza-Herrera et al., "Following DNA Chain Extension and Protein Conformational Changes in Crystals of a Y-Family DNA Polymerase via Raman Crystallography", Biochemistry, vol. 52, No. 29, Jul. 23, 2013.

Favicchio et al., "Fluorescence Spectroscopy and Anisotrophy in the analysis of DNA-Protein Interactions", Methods in Molecular Biology, DNA-Protein Interactions, vol. 543, 2009, pp. 589-611.

Federley, "New insights into the mechanism of dna replication on unmodified and benzo[a]pyrene modified templates using surface plasmon resonance", Wayne State University Dissertations, Paper 235, 2011.

Fuller et al., "The challenges of Sequencing by synthesis", Nature Biotechnology, vol. 27, No. 11, Nov. 2009, pp. 1013-1023.

Gralla et al., "Potassium Glutamate As A Transcriptional Inhibitor During Bacterial Osmoregulation", The EMBO Journal, vol. 25, No. 7, 2006, pp. 1515-1521.

Hoshino et al., "Effect of Ultrasound on DNA Polymerase Reactions: Monitoring on a 27-MHz Quartz Crystal Microbalance", Biomacromolecules, 7(3), 2006, pp. 682-685.

Hutter et al., "Labeled Nucleoside Triphosphates with Reversibly Terminating Aminoalkoxyl Groups", Nucleosides, Nucleotides and Nucleic Acids, vol. 29, Issue 11-12, 2010, pp. 879-895.

Ion Torrent, "Ion Torrent Amplicon Sequencing", Internet, Available at http://www.iontorrent.com/lib/images/PDFs/amplicon_application_note_040411.pdf, Apr. 4, 2011, pp. 1-5.

Jindal et al., "Suramin affects DNA Synthesis in HeLa Cells by Inhibition of DNA Polymerases", Cancer Research, 50, Dec. 15, 1990, pp. 7754-7757.

Jochmans et al., "Indolopyridones Inhibit Human Immunodeficiency Virus Reverse Transcriptase with a Novel Mechanism of Action", Journal of Virology, vol. 80, No. 24, Dec. 2006, p. 12283-12292.

Kaplan, "Photolabile chelators for the rapid photorelease of divalent cations", Proc. Natl. Acad. Sci. USA, vol. 85, Sep. 1988, pp. 6571-6575.

Kaushik et al., "Biochemical Analysis of Catalytically Crucial Aspartate Mutants of Human Immunodeficiency Virus Type 1 Reverse Transcriptase", Biochemistry, 35, 1996, 11536-11546.

Kim, "An FET-type charge sensor for highly sensitive detection of DNA sequence", Biosensors and Bioelectronics, Microsensors and Microsystems 2003, 20, No. 1, Jul. 30, 2004, 69-74.

Klenow et al., "Effect of Monovalent Cations on the Activity of the DNA Polymerase of Escherichia coli B", European J. Biochem., 1969, pp. 133-141.

Kumar et al., "Altered Order of Substrate Binding by DNA Polymerase X from African Swine Fever Virus", Biochemistry, 2008, pp. 7875-7887.

(56) References Cited

OTHER PUBLICATIONS

Leinbach et al., "Mechanism of phosphonoacetate inhibition of herpesvirus-induced DNA polymerase", Biochemistry, vol. 15, No. 2, 1976, pp. 426-430.
Lutz et al., "An in vitro screening technique for DNA polymerases that can incorporate modified nucleotides. Pseudothymidine as a substrate for thermostable polymerases", Nucleic Acids Research, vol. 27, No. 13, 1999, pp. 2792-2798.
Maga et al., "HIV-1 RT Inhibitors with a Novel Mechanism of Action: NNRTIs that Compete with the Nucleotide Substrate", Viruses, vol. 2, No. (4), 2010, pp. 880-899.
Maga et al., "Selective Interaction of the Human Immunodeficiency Virus Type 1 Reverse Transcriptase Nonnucleoside Inhibitor Efavirenz and Its Thio-Subsitituted Analog with Different Enzyme-Substrate Complexes", Antimicrobial Agents and Chemotherapy, vol. 44, No. 5, May 2000, pp. 1186-1194.
Mano, "Non-solid oncogenes in solid tumors: EML4-ALK fusion genes in lung cancer", Cancer Sci., vol. 99, 2008, pp. 2349-2355.
Markiewicz et al., "Single-Molecule Microscopy Reveals New Insights into Nucleotide Selection by DNA Polymerase 1", Nucleic Acids Research, vol. 40, No. 16, Jun. 4, 2012, pp. 7975-7984.
Mashayekhi, "Analysis of read length limiting factors in Pyrosequencing chemistry", Analytical Biochemistry, vol. 363, No. 2, Apr. 15, 2007, pp. 275-287.
Maxwell et al., "DNA Lesion Alters Global Conformational Dynamics of Y-family DNA Polymerase during Catalysis", The Journal of Biological Chemistry, vol. 287, No. 16, Apr. 13, 2012, pp. 13040-13047.
Namasivayam, "Light-Induced Molecular Cutting: Localized Reaction on a Single DNA Molecule", Anal. Chem., vol. 75, 2003, pp. 4118-4194.
Nath et al., "Label free colorimetric biosensing using nanoparticles", Journal of Fluorescence, vol. 14, No. 4, Jul. 2004, pp. 377-389.
Nazirizadeh, "Low-cost label-free biosensors using photonic crystals embedded between crossed polarizers", Optics Express, vol. 18, No. 18, Aug. 30, 2010, 19120-19128.
Nikiforov, "Oligonucleotides labeled with single flurophores as sensors for deoxynucleotide triphosphate binding by DNA polymerases", Analytical Biochemistry 444, 2014, pp. 60-66.
Patel, "Insights into DNA Polymerization Mechanisms from Structure and Function Analysis of HIV-1 Reverse Transcriptase ", Biochemistry, vol. 34, 1995, pp. 5351-5363.
PCT/US2017/042843, "PCT Search Report", Oct. 2, 2017, 15 pages.
PCT/US2017/042843, International Preliminary Report on Patentability dated Feb. 28, 2019, 8 pages.
Peletskaya et al., "Cross-Linking of the Fingers Subdomain of Human Immunodeficiency Virus Type 1 Reverse Transcriptase to Template-Primer", Journal of Virology, vol. 75, No. 19, Oct. 2001, pp. 9435-9445.
Pitta et al., "Synthesis and HIV-1 RT inhibitory action of novel (4/6-substituted benzo[d]thiazol-2-yl) thiazolidin-4-ones. Divergence from the non-competitive inhibition mechanism", J. Enzyme Inhib. Med. Chem., vol. 28, No. 10, 2013, pp. 113-122.
Potapova et al., "Interaction of dNTP, pyrophosphate and their analogs with the dNTP-binding sites of E. coli DNA polymerase I Klenow fragment and human DNA polymerase", FEBS letters, vol. 277, Issues 1-2, Dec. 17, 1990, pp. 194-196.
Previte et al., "DNA Sequencing Using Polymerase Substrate-binding Kinetics", Nature Communication, vol. 6, Jan. 23, 2015, 12 pages.
Ren et al., "Inhibition of Klenow DNA polymerase and poly(A)-specific ribonuclease by aminoglycosides", RNA 8, 2002, pp. 1393-1400.
Richard et al., "Thermal stability landscape for Klenow DNA polymerase as a function of pH and salt concentration", Biochemica et Biophysica Acta, vol. 1764, 2006, pp. 1546-1552.
Roettger et al., "Mismatched and Matched dNTP Incorporation by DNA Polymerase β Proceed via Analogues Kinetic Pathways", Biochemistry, 47, Sep. 16, 2008, pp. 9718-9727.
Santoso et al., "Conformational transitions in DNA polymerase I revealed by single-molecule FRET", Proceedings of the National Academy of Sciences, vol. 107, No. 2, Jan. 12, 2010, pp. 715-720.
Schadt et al., "Modeling Kinetic rate variation in third generation DNA sequencing data to detect putative modifications to DNA bases", Genome Research, 2013, pp. 129-141.
Schultz et al., "Single-target molecule detection with nonbleaching multicolor optical immunolabels", PNAS, vol. 96, No. 3, Feb. 1, 2000, 996-1001.
Sen et al., "Intrinsic fluorescence of E. coli RNA polymerase as a probe for its conformational changes during transcription initiation", Biochem Biophys Res Commun, vol. 201, No. 2, Jun. 15, 1994, pp. 820-828.
Star et al., "Electronic Detection of Specific Protein Binding Using Nanotube FET Devices", Nano Letters 3, No. 4, Apr. 1, 2003, 459-463.
Su, "Surface Plasmon Resonance Spectroscopy and Quartz Crystal Microbalance Study of Streptavidin Film Structure effects on Biotinylated DNA Assembly and Target DNA Hybridization", Langmuir, vol. 21, No. 1, 2005, pp. 348-353.
Tsai, "Kinetics of DNA Polymerase Conformational Changes during Nucleotide Binding and Incorporation", Dissertation, May 2005, pp. 1-48.
Tsai et al., "Site-specific labeling of T7 DNA polymerase with a conformationally sensitive fluorophore and its use in detecting single-nucleotide polymorphisms", Analytical Biochemistry, vol. 384, No. 1, Academic Press Inc., New York, Jan. 1, 2009, pp. 136-144.
Vaidyanathan et al., "Binary and ternary binding affinities between exonuclease-deficient Klenow fragment (Kf-exo(-)) and various arylamine DNA lesions characterized by surface plasmon resonance", Chem Res Toxicol, vol. 25, No. 8, Aug. 20, 2012, pp. 1568-1570.
Vaidyanathan et al., "Binding kinetics of DNA-protein interaction using surface plasmon resonance", Protocol Exchange, May 22, 2013.
Vollmer et al., "Whispering-gallery-mode biosensing: label-free detection down to single molecules", Nature Methods, vol. 5, No. 7, Jul. 2008, pp. 591-596.
Walsh, "Synthetic Nucleotides as Probes of DNA Polymerase Specificity", Journal of Nucleic Acids, vol. 2012, Article ID 530963, 17 pages.
Washington et al., "Human DNA Polymerase Utilizes Different Nucleotide Incorporation Mechanisms Dependent upon the Template Base", Molecular and Cellular Biology, vol. 24, No. 2, Jan. 2004, 936-943.
Xia et al., "DNA Mismatch Synthesis Complexes Provide Insights into Base Selectivity of a B family DNA Polymerase", J Am Chem Soc. 135(1), Jan. 9, 2013, 193-202.
Yuzenkova et al., "Tagetitoxin inhibits transcription by stabilizing pre-translocated state of the elongation complex", Nucleic Acids Research, 2013, pp. 9257-9265.
U.S. Appl. No. 15/654,406, "Non-Final Office Action", dated Apr. 11, 2019, 6 pages.
U.S. Appl. No. 15/654,406, "Notice of Allowance", dated Jul. 31, 2019, 9 pages.

* cited by examiner

US 11,203,779 B2

SEQUENCING METHOD FOR RAPID IDENTIFICATION AND PROCESSING OF COGNATE NUCLEOTIDE PAIRS

RELATED APPLICATIONS

This application is continuation application of U.S. application Ser. No. 15/654,406, filed on Jul. 19, 2017, which claims the benefit of U.S. Provisional Application No. 62/375,389, filed Aug. 15, 2016. The entire disclosure of these applications are hereby incorporated by reference.

TECHNICAL FIELD

The present invention relates generally to the field of biotechnology. More specifically, the invention concerns nucleic acid sequencing technology.

BACKGROUND

Simplifying large-scale sequencing projects, such as genome-scale projects, depends on rapid acquisition of DNA sequence data. Unfortunately, nucleic acid sequencing procedures typically involve time-consuming cycling of reagents, enzymatic reactions that must go to completion, and potentially long periods of acquiring measurement data. Of course, all of this is a legacy of the early nucleic acid sequencing paradigms that relied on processing one nucleotide position at a time.

Alternative methods aimed at identifying short stretches of sequence at one time (e.g., using sequencing-by-hybridization) have not found wide acceptance for determining unknown sequences. Instead, these techniques generally are applied to investigating subtle changes in sequences that already are known. The same is true for techniques that are based on "melting curve analysis," where the interrogation sequences are commonly no larger than about twenty nucleotides in length.

The techniques described herein provide an approach that advantageously speeds acquisition of nucleic acid sequence data and provide other advantages as well.

SUMMARY OF THE DISCLOSURE

In one aspect, the disclosure relates to a method of determining the identity of first and second correct nucleotides respectively including bases complementary to the next two bases of a template strand immediately downstream of a primer of a primed template nucleic acid molecule. The method includes the step of (a) conducting a plurality of cycles of contacting a first primed template nucleic acid molecule with a reaction mixture that includes a polymerase and, for each cycle, a different test nucleotide, and removing any polymerase and nucleotide that may have bound to the first primed template nucleic acid molecule. The polymerase does not incorporate any of the different test nucleotides into the primer of the first primed template nucleic acid molecule during any of the plurality of cycles. There also is the step of (b) measuring, for each of the cycles in step (a), signals indicating binding of the first primed template nucleic acid molecule to the polymerase and one of the different test nucleotides to identify a test nucleotide associated with the highest magnitude of ternary complex formation, and a test nucleotide associated with the second-highest magnitude of ternary complex formation. There also is the step of (c) determining the identities of the first correct nucleotide downstream of the primer, and the second correct nucleotide downstream of the primer using the measured binding signals from step (b). According to one generally preferred embodiment, the primer of the first primed template nucleic acid molecule is an extendable primer that does not include a reversible terminator moiety attached to its 3' terminal nucleotide. When this is the case, the reaction mixture can include either a divalent non-catalytic metal ion that inhibits polymerase-mediated incorporation, or a trivalent non-catalytic metal ion that inhibits polymerase-mediated incorporation. Alternatively, the plurality of cycles in step (a) can include four cycles. According to another alternative, step (c) can involve determining that the test nucleotide associated with the highest magnitude of ternary complex formation is the first correct nucleotide downstream of the primer, and that the test nucleotide associated with the second-highest magnitude of ternary complex formation is the second correct nucleotide downstream of the primer. According to still a different alternative, the method further includes the step of (d) incorporating a reversible terminator nucleotide including a reversible terminator moiety into the first primed template nucleic acid molecule to produce a first blocked primed template nucleic acid molecule. More preferably, there is the further step of (e) removing the reversible terminator moiety from the first blocked primed template nucleic acid molecule to produce a first de-blocked primed template nucleic acid molecule. Still more preferably, the method further involves repeating steps (a)-(c) using the first de-blocked primed template nucleic acid molecule in place of the first primed template nucleic acid molecule. Alternatively, the method further includes the steps of: (f) incorporating a reversible terminator nucleotide including a reversible terminator moiety into the first de-blocked primed template nucleic acid molecule to produce a second blocked primed template nucleic acid molecule; and (g) removing the reversible terminator moiety from the second blocked primed template nucleic acid molecule to produce a second de-blocked primed template nucleic acid molecule. More preferably, the method further involves repeating steps (a)-(c) using the second de-blocked primed template nucleic acid molecule in place of the first primed template nucleic acid molecule. More preferably, step (c) occurs after all of steps (a)-(b) and (d)-(g) have been performed. Optionally, none of the different test nucleotides includes an exogenous fluorescent label. When this is the case, each of the different test nucleotides can be a different native nucleotide. Optionally, the polymerase does not include an exogenous fluorescent label, and step (b) does not include measuring any fluorescent signal from the polymerase. According to another generally preferred embodiment, the first primed template nucleic acid molecule is a first blocked primed template nucleic acid molecule, and the primer of the first blocked primed template nucleic acid molecule includes a reversible terminator moiety that blocks phosphodiester bond formation. When this is the case, the reaction mixture can include a catalytic metal ion. Alternatively, the plurality of cycles in step (a) can include four cycles. According to another alternative, step (c) involves determining that the test nucleotide associated with the highest magnitude of ternary complex formation is the first correct nucleotide downstream of the primer, and that the test nucleotide associated with the second-highest magnitude of ternary complex formation is the second correct nucleotide downstream of the primer. According to still another alternative, the method further includes the steps of: (d) removing the reversible terminator moiety from the primer of the first blocked primed template nucleic acid molecule to produce a first de-blocked primer; and (e) incorporating a reversible terminator nucleotide including a reversible terminator moiety into the first de-blocked primer to produce a second blocked primed template nucleic acid molecule. More preferably, steps (a)-(c) are repeated using the second blocked primed template nucleic acid molecule in place of the first blocked primed template nucleic acid molecule. Alternatively, the method further includes, after step (e), the steps of: (f) removing the reversible terminator moiety from the second blocked primed template nucleic acid molecule to produce a second de-blocked primer; and (g) incorporating a reversible terminator nucleotide including a reversible terminator moiety into the second de-blocked primer to produce a third blocked primed template nucleic acid molecule. More preferably, steps (a)-(c) can be repeated using the third blocked primed template nucleic acid molecule in place of the first blocked primed template nucleic acid molecule. Still more preferably, step (c) occurs after all of steps (a)-(b) and (d)-(g) have been performed. Optionally, in any of the embodiments none of the different test nucleotides includes an exogenous fluorescent label. When this is the case, each of the different test nucleotides can be a different native nucleotide. Optionally, in any of the embodiments the polymerase does not include an exogenous fluorescent label, and step (b) does not include measuring any fluorescent signal from the polymerase. According to still yet another embodiment, when the first primed template nucleic acid molecule is a first blocked primed template nucleic acid molecule, and when the primer of the first blocked primed template nucleic acid molecule includes a reversible terminator moiety that blocks phosphodiester bond formation, the reversible terminator moiety that blocks phosphodiester bond formation can be a 3'-ONH$_2$ moiety.

In another aspect, the disclosure relates to a method of identifying a nucleotide that includes a base complementary to the next base of a template strand immediately downstream of the primer of a primed template nucleic acid molecule. The method includes the step of (a) contacting the primed template nucleic acid molecule with a first reaction mixture that includes a polymerase, a reversible terminator nucleotide that includes a reversible terminator moiety, and a catalytic metal ion. The reversible terminator nucleotide can incorporate at the 3'-end of the primer of the primed template nucleic acid molecule to produce a reversibly blocked under examination reaction conditions.
blocked primed template nucleic acid molecule with a second reaction mixture that includes a polymerase, at least one nucleotide molecule, and a catalytic metal ion. A ternary complex forms if one of said at least one nucleotide molecule includes the base complementary to the next base of the template strand. There also is the step of (c) monitoring interaction of the polymerase from the second reaction mixture and the reversibly blocked primed template nucleic acid molecule to detect any of the ternary complex that may have formed. There also is the step of (d) determining either that: one of the at least one nucleotide molecule of the second reaction mixture is the next correct nucleotide if the ternary complex is detected in step (c), or none of said at least one nucleotide molecule of the second reaction mixture is the next correct nucleotide if the ternary complex is not detected in step (c). According to one generally preferred embodiment, the at least one nucleotide molecule includes a plurality of nucleotide molecules, where the ternary complex forms if one of the plurality of nucleotide molecules includes the base complementary to the next base of the template strand, and where step (d) includes determining either that: one of the plurality of nucleotide molecules of the second reaction mixture is the next correct nucleotide if the ternary complex is detected in step (c), or none of the plurality of nucleotide molecules of the second reaction mixture is the next correct nucleotide if the ternary complex is not detected in step (c). Optionally, the method further includes the steps of: (e) removing the reversible terminator moiety from the reversibly blocked primed template nucleic acid molecule to produce an unblocked primed template nucleic acid molecule; and (f) repeating steps (a)-(d) using the unblocked primed template nucleic acid molecule in place of the primed template nucleic acid molecule. More preferably, the at least one nucleotide molecule in step (b) is only a single nucleotide molecule, the ternary complex forms if the single nucleotide molecule includes the base complementary to the next base of the template strand, and step (d) includes determining either that: the single nucleotide molecule of the second reaction mixture is the next correct nucleotide if the ternary complex is detected in step (c), or the single nucleotide molecule of the second reaction mixture is not the next correct nucleotide if the ternary complex is not detected in step (c). Optionally, in any of the embodiments the primed template nucleic acid molecule is immobilized to a solid support, and steps (a) and (b) include flowing the reaction mixtures over the immobilized primed template nucleic acid molecule. Optionally, in any of the embodiments the catalytic metal ion is magnesium ion or manganese ion. Optionally, in any of the embodiments the reversible terminator moiety includes a chemical moiety attached at the 3' position of the terminal nucleotide of the primer. When this is the case, the chemical moiety includes a 3'-ONH$_2$ moiety. Optionally, in any of the embodiments step (c) can involve monitoring continuously. Optionally, the polymerase of the second reaction mixture includes an exogenous label. When this is the case, the exogenous label can include a fluorescent label. More preferably, the fluorescent label of the polymerase of the second reaction mixture is not a conformationally sensitive fluorescent label that changes optical properties upon interaction with a nucleotide. Still more preferably, the polymerases of the first and second reaction mixtures are different DNA polymerases. Optionally, step (d) involves removing with a chemical reagent. Optionally, each of the at least one nucleotide molecules is a native nucleotide molecule that does not include an exogenous fluorescent label.

In another aspect, the disclosure relates to a method of determining the identity of first and second correct nucleotides respectively including bases complementary to the next two bases of a template strand immediately downstream of a primer in a primed template nucleic acid molecule. The method includes the step of (a) conducting a plurality of cycles of contacting a first primed template nucleic acid molecule with a reaction mixture including a polymerase and, for each cycle, a different pair of test nucleotides, and removing any polymerase and nucleotide that may have bound to the first primed template nucleic acid molecule, where the polymerase does not incorporate any of the different test nucleotides into the primer of the first primed template nucleic acid molecule during any of the four cycles. There also is the step of (b) measuring, for each of the cycles in step (a), signals indicating binding of the first primed template nucleic acid molecule to the polymerase and at least one of the test nucleotides among the different pairs of test nucleotides to identify a test nucleotide associated with the highest magnitude of ternary complex formation, and a test nucleotide associated with the second-highest magnitude of ternary complex formation. There also is the step of (c) determining the identities of the first correct nucleotide downstream of the primer, and the second correct nucleotide downstream of the primer using the measured binding signals from step (c). According to one generally preferred embodiment, the plurality of cycles in step (a) includes at least four cycles. According to a different generally preferred embodiment, step (c) can involve determining that the test nucleotide associated with the highest magnitude of ternary complex formation is the first correct nucleotide downstream of the primer, and the test nucleotide associated with the second-highest magnitude of ternary complex formation is the second correct nucleotide downstream of the primer. According to still a different generally preferred embodiment, conducting the plurality of cycles in step (a) can involve conducting only four cycles, and the different pairs of test nucleotides of the reaction mixture of step (a) can be any of: (i) dATP and dGTP, dATP and dCTP, dGTP and dTTP, dCTP and dTTP; (ii) dATP and dGTP, dATP and dTTP, dGTP and dCTP, dCTP and dTTP; and (iii) dATP and dCTP, dATP and dTTP, dGTP and dCTP, dGTP and dTTP. According to still a different generally preferred embodiment, conducting the plurality of cycles in step (a) can involve conducting six cycles, and the different pairs of test nucleotides of the reaction mixture can be: dATP and dGTP, dATP and dCTP, dATP and dTTP, dGTP and dCTP, dGTP and dTTP, and dCTP and dTTP. According to still yet a different generally preferred embodiment, the method further includes the step of: (d) incorporating a reversible terminator nucleotide including a reversible terminator moiety into the first primed template nucleic acid molecule to produce a first blocked primed template nucleic acid molecule. When this is the case, the method may further include the step of: (e) removing the reversible terminator moiety from the first blocked primed template nucleic acid molecule to produce a first de-blocked primed template nucleic acid molecule. More preferably, the method further involves repeating steps (a)-(c) using the first de-blocked primed template nucleic acid molecule in place of the first primed template nucleic acid molecule. Alternatively, the method further includes the steps of: (f) incorporating a reversible terminator nucleotide including a reversible terminator moiety into the first de-blocked primed template nucleic acid molecule to produce a second blocked primed template nucleic acid molecule; and (g) removing the reversible terminator moiety from the second blocked primed template nucleic acid molecule to produce a second de-blocked primed template nucleic acid molecule. More preferably, the method further involves repeating steps (a)-(c) using the second de-blocked primed template nucleic acid molecule in place of the first primed template nucleic acid molecule. Optionally, in any of the embodiments that include step (d), step (c) occurs after all of the other steps have been performed. Optionally, in any of the embodiments none of the different test nucleotides includes an exogenous fluorescent label. Optionally, in any of the embodiments each of the different test nucleotides is a different native nucleotide. Optionally, in any of the embodiments the polymerase does not include an exogenous fluorescent label, and step (b) does not include measuring any fluorescent signal produced by the polymerase. Optionally, in any of the embodiments the reaction mixture includes a non-catalytic metal ion that inhibits polymerase-mediated incorporation. Optionally, in any of the embodiments the reaction mixture includes a catalytic metal ion.

In another aspect, the disclosure relates to a method of determining the identity of first and second correct nucleotides respectively including bases complementary to the next two bases of a template strand in a blocked primed template nucleic acid molecule. The method includes the steps of: (a) conducting a plurality of cycles of contacting a first blocked primed template nucleic acid molecule with a reaction mixture including a polymerase and, for each cycle, a different pair of test nucleotides, and removing any polymerase and nucleotide that may have bound to the first blocked primed template nucleic acid molecule, where the first blocked primed template nucleic acid molecule includes a primer with a reversible terminator moiety that blocks phosphodiester bond formation. There also is the step of (b) measuring, for each of the cycles in step (a), signals indicating binding of the first blocked primed template nucleic acid molecule to the polymerase and at least one of the test nucleotides among the different pairs of test nucleotides to identify a test nucleotide associated with the highest magnitude of ternary complex formation, and a test nucleotide associated with the second-highest magnitude of ternary complex formation. There also is the step of (c) determining the identities of the first correct nucleotide downstream of the primer, and the second correct nucleotide downstream of the primer using the measured binding signals from step (c). According to one generally preferred embodiment, the plurality of cycles in step (a) involves at least four cycles. According to a different generally preferred embodiment, step (c) involves determining that the test nucleotide associated with the highest magnitude of ternary complex formation is the first correct nucleotide downstream of the primer, and that the test nucleotide associated with the second-highest magnitude of ternary complex formation is the second correct nucleotide downstream of the primer. According to still a different generally preferred embodiment, conducting the plurality of cycles in step (a) can involve conducting only four cycles, and the different pairs of test nucleotides of the reaction mixture of step (a) can be any of: (i) dATP and dGTP, dATP and dCTP, dGTP and dTTP, dCTP and dTTP; (ii) dATP and dGTP, dATP and dTTP, dGTP and dCTP, dCTP and dTTP; and (iii) dATP and dCTP, dATP and dTTP, dGTP and dCTP, dGTP and dTTP. According to yet a different generally preferred embodiment, conducting the plurality of cycles in step (a) can involve conducting six cycles, and the different pairs of test nucleotides of the reaction mixture can be: dATP and dGTP, dATP and dCTP, dATP and dTTP, dGTP and dCTP, dGTP and dTTP, and dCTP and dTTP. According to still yet a different generally preferred embodiment, the method can further include the steps of: (d) removing the reversible terminator moiety from the primer of the first blocked primed template nucleic acid molecule to produce a first de-blocked primer; and (e) incorporating a reversible terminator nucleotide including a reversible terminator moiety into the first de-blocked primer to produce a second blocked primed template nucleic acid molecule. When this is the case, steps (a)-(c) can be repeated using the second blocked primed template nucleic acid molecule in place of the first blocked primed template nucleic acid molecule. More preferably, conducting the plurality of cycles in step (a) can involve conducting only four cycles, and the different pairs of test nucleotides of the reaction mixture of step (a) can be any of: (i) dATP and dGTP, dATP and dCTP, dGTP and dTTP, dCTP and dTTP; (ii) dATP and dGTP, dATP and dTTP, dGTP and dCTP, dCTP and dTTP; and (iii) dATP and dCTP, dATP and dTTP, dGTP and dCTP, dGTP and dTTP. Still more preferably, conducting the plurality of cycles in step (a) can involve conducting six cycles, and the different pairs of test nucleotides of the reaction mixture can be: dATP and dGTP, dATP and dCTP, dATP and dTTP, dGTP and dCTP, dGTP and dTTP, and dCTP and dTTP. In accordance with embodiments that include steps (d) and (e), the method further includes, after step (e), the steps of: (f) removing the reversible terminator moiety from the second blocked primed template nucleic acid molecule to produce a second de-blocked primer; and (g) incorporating a reversible terminator nucleotide including a reversible terminator moiety into the second de-blocked primer to produce a third blocked primed template nucleic acid molecule. More preferably, steps (a)-(c) can be repeated using the third blocked primed template nucleic acid molecule in place of the first blocked primed template nucleic acid molecule. Still more preferably, conducting the plurality of cycles in step (a) involves conducting only four cycles, and where the different pairs of test nucleotides of the reaction mixture of step (a) are any of: (i) dATP and dGTP, dATP and dCTP, dGTP and dTTP, dCTP and dTTP; (ii) dATP and dGTP, dATP and dTTP, dGTP and dCTP, dCTP and dTTP; and (iii) dATP and dCTP, dATP and dTTP, dGTP and dCTP, dGTP and dTTP. Alternatively, conducting the plurality of cycles in step (a) involves conducting six cycles, and the different pairs of test nucleotides of the reaction mixture can be: dATP and dGTP, dATP and dCTP, dATP and dTTP, dGTP and dCTP, dGTP and dTTP, and dCTP and dTTP. Optionally, in any of the embodiments step (c) occurs after all of the other steps have been performed. Optionally, in any of the embodiments none of the different test nucleotides includes an exogenous fluorescent label. Optionally, in any of the embodiments each of the different test nucleotides is a different native nucleotide. Optionally, in any of the embodiments the polymerase does not include an exogenous fluorescent label, and step (b) does not involve measuring any fluorescent signal from the polymerase. Optionally, in any of the embodiments the reaction mixture includes a non-catalytic metal ion that inhibits polymerase-mediated incorporation. Optionally, in any of the embodiments the reaction mixture includes a catalytic metal ion.

In another aspect, the disclosure relates to a method of determining the identity of first and second correct nucleotides respectively including bases complementary to the next two bases of a template strand immediately downstream of a primer in a primed template nucleic acid molecule. The method includes the step of (a) conducting a plurality of cycles of contacting a first primed template nucleic acid molecule with a reaction mixture that includes a polymerase and, for each cycle, a different test nucleotide, and removing any polymerase and nucleotide that may have bound to the first primed template nucleic acid molecule. The polymerase does not incorporate any of the different test nucleotides into the primer of the first primed template nucleic acid molecule during any of the plurality of cycles. There also is the step of (b) measuring, for each of the cycles in step (a), signals indicating binding of the first primed template nucleic acid molecule to the polymerase and one of the different test nucleotides to identify a test nucleotide associated with the highest magnitude of ternary complex formation, and a test nucleotide associated with the second-highest magnitude of ternary complex formation. There also is the step of (c) determining the identities of the first correct nucleotide downstream of the primer, and the second correct nucleotide downstream of the primer using the measured binding signals from step (b). According to one generally preferred embodiment, the plurality of cycles in step (a) includes four cycles. According to a different generally preferred embodiment, step (c) can involve determining that the test nucleotide associated with the highest magnitude of ternary complex formation is the first correct nucleotide downstream of the primer, and that the test nucleotide associated with the second-highest magnitude of ternary complex formation is the second correct nucleotide downstream of the primer. According to still a different generally preferred embodiment, the method further includes the step of (d) incorporating a reversible terminator nucleotide including a reversible terminator moiety into the first primed template nucleic acid molecule to produce a first blocked primed template nucleic acid molecule. When this is the case, the method can further include the step of (e) removing the reversible terminator moiety from the first blocked primed template nucleic acid molecule to produce a first de-blocked primed template nucleic acid molecule. More preferably, the method can further involve repeating steps (a)-(c) using the first de-blocked primed template nucleic acid molecule in place of the first primed template nucleic acid molecule. Still more preferably, the method further includes the steps of: (f) incorporating a reversible terminator nucleotide including a reversible terminator moiety into the first de-blocked primed template nucleic acid molecule to produce a second blocked primed template nucleic acid molecule; and (g) removing the reversible terminator moiety from the second blocked primed template nucleic acid molecule to produce a second de-blocked primed template nucleic acid molecule. Yet still more preferably, the method can further involve repeating steps (a)-(c) using the second de-blocked primed template nucleic acid molecule in place of the first primed template nucleic acid molecule. When this is the case, step (c) can occur after all of the other steps have been performed. Optionally, in any of the embodiments none of the different test nucleotides includes an exogenous fluorescent label. More preferably, each of the different test nucleotides is a different native nucleotide. Optionally, in any of the embodiments the polymerase does not include an exogenous fluorescent label, and step (b) does not include measuring any fluorescent signal from the polymerase. Optionally, in any of the embodiments the reaction mixture includes a non-catalytic metal ion that inhibits polymerase-mediated incorporation. Optionally, in any of the embodiments the reaction mixture includes a catalytic metal ion.

In another aspect, the disclosure relates to method of determining the identity of first and second correct nucleotides respectively including bases complementary to the next two bases of a template strand in a blocked primed template nucleic acid molecule. The method includes the step of (a) conducting a plurality of cycles of contacting a first blocked primed template nucleic acid molecule with a reaction mixture including a polymerase and, for each cycle, a different test nucleotide, and removing any polymerase and nucleotide that may have bound to the first blocked primed template nucleic acid molecule, where the first blocked primed template nucleic acid molecule includes a primer with a reversible terminator moiety that blocks phosphodiester bond formation. There also is the step of (b) measuring, for each of the cycles in step (a), signals indicating binding of the first blocked primed template nucleic acid molecule to the polymerase and one of the different test nucleotides to identify a test nucleotide associated with the highest magnitude of ternary complex formation, and a test nucleotide associated with the second-highest magnitude of ternary complex formation. There also is the step of (c) determining the identities of the first correct nucleotide downstream of the primer, and the second correct nucleotide downstream of the primer using the measured binding signals from step (c). According to one generally preferred embodiment, the plurality of cycles in step (a) includes four cycles. According to a different generally preferred embodiment, step (c) can involve determining that the test nucleotide associated with the highest magnitude of ternary complex formation is the first correct nucleotide downstream of the primer, and that the test nucleotide associated with the second-highest magnitude of ternary complex formation is the second correct nucleotide downstream of the primer. According to still a different generally preferred embodiment, the method further includes the steps of: (d) removing the reversible terminator moiety from the primer of the first blocked primed template nucleic acid molecule to produce a first de-blocked primer; and (e) incorporating a reversible terminator nucleotide including a reversible terminator moiety into the first de-blocked primer to produce a second blocked primed template nucleic acid molecule. When this is the case, steps (a)-(c) can be repeated using the second blocked primed template nucleic acid molecule in place of the first blocked primed template nucleic acid molecule. More preferably, the method further includes, after step (e), the steps of: (f) removing the reversible terminator moiety from the second blocked primed template nucleic acid molecule to produce a second de-blocked primer; and (g) incorporating a reversible terminator nucleotide including a reversible terminator moiety into the second de-blocked primer to produce a third blocked primed template nucleic acid molecule. Still more preferably, steps (a)-(c) are repeated using the third blocked primed template nucleic acid molecule in place of the first blocked primed template nucleic acid molecule. Optionally, in any of the embodiments step (c) occurs after all of the other steps have been performed. Optionally, in any of the embodiments none of the different test nucleotides includes an exogenous fluorescent label. Optionally, in any of the embodiments each of the different test nucleotides is a different native nucleotide. Optionally, in any of the embodiments the polymerase does not include an exogenous fluorescent label, and step (b) does not include measuring any fluorescent signal from the polymerase. Optionally, in any of the embodiments the reaction mixture includes a non-catalytic metal ion that inhibits polymerase-mediated incorporation. Optionally, in any of the embodiments the reaction mixture includes a catalytic metal ion.

BRIEF DESCRIPTION OF THE DRAWINGS

FIG. 5A is an interferometry trace showing magnitude of binding (vertical axis) as a function of time (horizontal axis), where different nucleotide pairs were used during examination. FIG. 5B is a bar graph showing the calculated $R_{eq}$ parameter for each different nucleotide pair used in the examination step. FIG. 5C is a bar graph showing the calculated $k_{obs}$ parameter for each different nucleotide pair used in the examination step.

FIG. 6A is an interferometry trace showing magnitude of binding (vertical axis) as a function of time (horizontal axis), where different nucleotide pairs were used during examination. FIG. 6B is a bar graph showing the calculated $R_{eq}$ parameter for each different nucleotide pair used in the examination step. FIG. 6C is a bar graph showing the calculated $k_{obs}$ parameter for each different nucleotide pair used in the examination step.

DETAILED DESCRIPTION

Figure 1A:
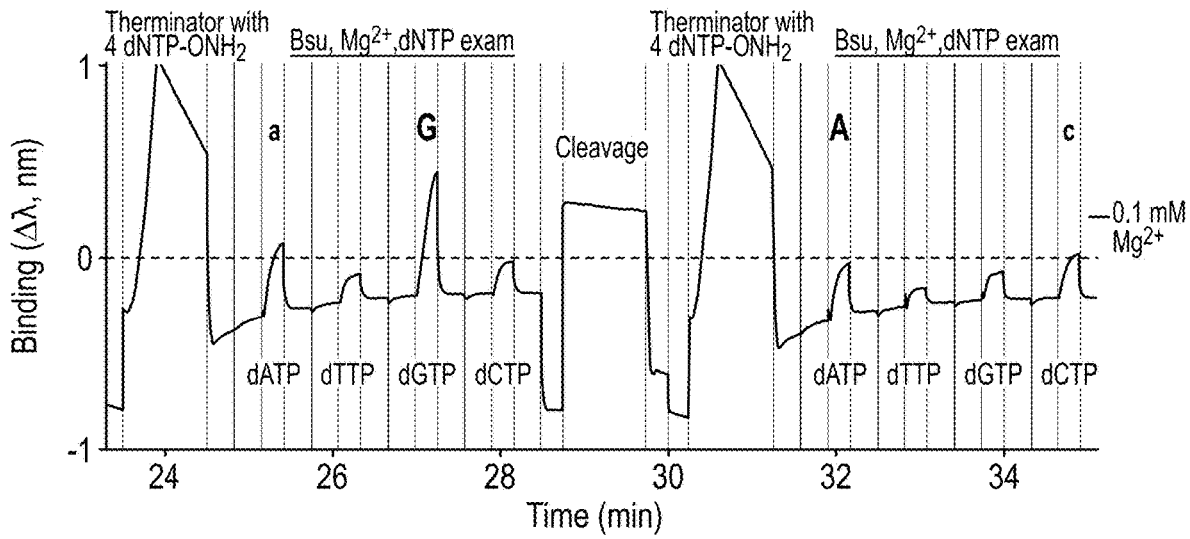
FIGS. 1A-1B are interferometry traces for the examination and incorporation cycles of the expected sequence (GAC) in example sequencing runs. Binding signals for all four dNTPs at the same position are illustrated in the presence of 0.1 mM MgCl$_2$ (FIG. 1A) or 1 mM MgCl$_2$ (FIG. 1B). All examination cycles were conducted after incorporating the correct 3'-blocked nucleotide, but before cleavage of the 3'-ONH$_2$ reversible terminator moiety to reveal an extendable 3'-OH group. Bases for the next correct incoming nucleotides (n+1) are highlighted using bold uppercase base identifiers for their respective positions in the sequence. Additionally, the second correct bases (n+2) are highlighted using bold lowercase base identifiers on their respective binding signal peaks. The order of nucleotide examination was: dATP, dTTP, dGTP, and dCTP.

Provided herein is a method for identifying the next two cognate nucleotides downstream of a primer in a primed template nucleic acid, with or without a blocking moiety that precludes phosphodiester bond formation involving the 3'-OH group. The identification does not depend on incorporation of any nucleotide into the primer. The method can be practiced using a sequencing-by-binding platform, and can involve examination in the presence of any of non-catalytic metal ions that inhibit polymerase-mediated incorporation, reversibly terminated primers, or the combination of reversibly terminated primers and catalytic metal ions. Alternatively or additionally, examination can use a polymerase mutant that is catalytically inactive such that extension is inhibited. Another means to prevent extension during an examination step is to use non-incorporable nucleotide analogs. Results from the identification can be used for confirming sequencing information (e.g., serving a verification function), or can facilitate incorporation of two nucleotides to extend the primer before any subsequent examination is performed. When the primer is extended by incorporating two nucleotides preliminary to the next examination step, the time needed to complete a sequencing procedure can be reduced significantly.

In particular embodiments the method involves detecting the magnitudes of interaction between a primed template nucleic acid molecule (optionally having a blocked 3'-end), a polymerase, and a set of four different nucleotides without incorporating any of the nucleotides into the primer of the primed template nucleic acid. More particularly, the method can involve detecting signals indicating formation of a complex that includes three molecular species and determining which two out of the possible four nucleotides are associated with the greatest amount or magnitude of complex formation. The nucleotide giving the highest amount of complex formation (e.g., the highest magnitude of binding signal) is the next correct nucleotide. The nucleotide giving the second-highest level of complex formation (e.g., the second-highest magnitude of binding signal) is the subsequent correct nucleotide.

Advantageously, the technique can even be practiced using various types of nucleotides, including native (e.g., unlabeled) nucleotides, nucleotides with detectable labels (e.g., fluorescent or other optically detectable labels), or labeled or unlabeled nucleotide analogs (e.g., modified nucleotides containing reversible terminator moieties). Further, the technique provides controlled reaction conditions, unambiguous determination of sequence, low overall cost of reagents, and low instrument cost.

Indeed, numerous variations on the sequencing-by-binding assay chemistry are within the scope of alternatives that can be used for carrying out the method described herein. Optionally, the primer of the primed template nucleic acid molecule used in the examination step can be a blocked template nucleic acid molecule (e.g., as may result following incorporation of a reversible terminator nucleotide into the primer component of the primed template nucleic acid molecule). Optionally, nucleotides used in the examination steps can include exogenous labels, such as exogenous fluorescent labels. Alternatively or additionally to the use of labeled nucleotides, the polymerase used in the examination steps includes an exogenous fluorescent label. Optionally, neither the nucleotides nor the polymerase used in the examination steps include exogenous detectable labels, and the system provides a route for label-free determination of the identities of two cognate nucleotides from examination of four different nucleotides. Optionally, reversible terminator nucleotides can be incorporated into a primer strand to ensure that only a single nucleotide is incorporated. Optionally, a pair of reversible terminator nucleotides is incorporated into a primer strand, with the reversible terminator moiety of the first reversible terminator nucleotide being removed before the second reversible terminator nucleotide is incorporated. Optionally, the reversible terminator moiety is removed from the primer of a blocked primed template nucleic acid before individuals from the next set of four different nucleotides are tested for binding in the presence of a polymerase. By this approach, the primer used in the examination steps will terminate in a 3'-OH group that can participate in phosphodiester bond formation with a cognate nucleotide. Optionally, the reversible terminator moiety of the primer of a blocked primed template nucleic acid is left in place before individuals from the next set of four different nucleotides are tested for binding in the presence of a polymerase. By this approach, the blocked primer is used in the examination reaction.

The technique may be applied to single nucleotide determination (e.g., SNP determination based on a single full cycle procedure), or alternatively to more extensive nucleic acid sequencing procedures employing reiterative cycles that identify one nucleotide at a time. For example, the methods provided herein can be used in connection with sequencing-by-binding procedures, as described in the commonly owned U.S. patent applications identified by Ser. Nos. 62/447,319 and 2017/0022553, the disclosures of which are incorporated by reference herein in their entireties.

Definitions

Unless defined otherwise, all technical and scientific terms used herein have the same meaning as is commonly understood by one of ordinary skill in the art. For clarity, the following specific terms have the specified meanings. Other terms are defined in other sections herein.

The singular forms "a" "an" and "the" include plural referents unless the context clearly dictates otherwise. Approximating language, as used in the description and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the compositions, apparatus, or methods of the present disclosure. At the very least, each numerical parameter should at least be construed in light of the number of reported significant digits and by applying ordinary rounding techniques.

As used herein, "sequencing-by-binding" refers to a sequencing technique wherein specific binding of a polymerase and a next correct nucleotide to a primed template nucleic acid is used for identifying the next correct nucleotide to be incorporated into the primer strand of the primed template nucleic acid. The specific binding interaction precedes chemical incorporation of the nucleotide into the primer strand, and so identification of the next correct nucleotide can take place either without or before incorporation of the next correct nucleotide.

As used herein, "nucleic acid" or "oligonucleotide" or "polynucleotide" means at least two nucleotides covalently linked together. Thus, the terms include, but are not limited to, DNA, RNA, analogs (e.g., derivatives) thereof or any combination thereof, that can be acted upon by a polymerizing enzyme during nucleic acid synthesis. The term includes single-, double-, or multiple-stranded DNA, RNA and analogs (e.g., derivatives) thereof. Double-stranded nucleic acids advantageously can minimize secondary structures that may hinder nucleic acid synthesis. A double-stranded nucleic acid may possess a nick or a single-stranded gap. A nucleic acid may represent a single, plural, or clonally amplified population of nucleic acid molecules.

As used herein, a "template nucleic acid" is a nucleic acid to be detected, sequenced, evaluated or otherwise analyzed using a method or apparatus disclosed herein.

As used herein, a "primed template nucleic acid" (or alternatively, "primed template nucleic acid molecule") is a template nucleic acid primed with (i.e., hybridized to) a primer, wherein the primer is an oligonucleotide having a 3'-end with a sequence complementary to a portion of the template nucleic acid. The primer can optionally have a free 5'-end (e.g., the primer being noncovalently associated with the template) or the primer can be continuous with the template (e.g., via a hairpin structure). The primed template nucleic acid includes the complementary primer and the template nucleic acid to which it is bound. A primed template nucleic acid molecule can be extendable in a polymerization reaction or it can be a blocked primed template nucleic acid. By "extendable" it is meant that a cognate nucleotide can be joined to the 3'-end of a primer strand by formation of a phosphodiester bond.

As used herein, a "blocked primed template nucleic acid" (or alternatively, "blocked primed template nucleic acid molecule") is a primed template nucleic acid modified to preclude or prevent phosphodiester bond formation at the 3'-end of the primer. Blocking may be accomplished, for example, by chemical modification with a blocking group at either the 3' or 2' position of the five-carbon sugar at the 3' terminus of the primer. Alternatively, or in addition, chemical modifications that preclude or prevent phosphodiester bond formation may also be made to the nitrogenous base of a nucleotide. Reversible terminator nucleotide analogs including each of these types of blocking groups will be familiar to those having an ordinary level of skill in the art. Incorporation of these analogs at the 3' terminus of a primer of a primed template nucleic acid molecule results in a blocked primed template nucleic acid molecule. The blocked primed template nucleic acid includes the complementary primer, blocked from extension at its 3'-end, and the template nucleic acid to which it is bound.

As used herein, a "nucleotide" is a molecule that includes a nitrogenous base, a five-carbon sugar (e.g., ribose or deoxyribose), and at least one phosphate group or functional analogs of such a molecule. The functional analogs may have a function of forming a ternary complex with a polymerase and primed template nucleic acid (or blocked primed template nucleic acid) and/or a function of being incorporated into a primed template nucleic acid. The term embraces ribonucleotides, deoxyribonucleotides, nucleotides modified to include exogenous labels or reversible terminators, and nucleotide analogs.

As used herein, a "native" nucleotide refers to a naturally occurring nucleotide that does not include an exogenous label (e.g., a fluorescent dye, or other label) or chemical modification such as may characterize a nucleotide analog. Examples of native nucleotides useful for carrying out the sequencing-by-binding procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, a "nucleotide analog" has one or more modifications, such as chemical moieties, which replace, remove and/or modify any of the components (e.g., nitrogenous base, five-carbon sugar, or phosphate group(s)) of a native nucleotide. Nucleotide analogs may be either incorporable or non-incorporable by a polymerase in a nucleic acid polymerization reaction. Optionally, the 3'-OH group of a nucleotide analog is modified with a moiety. The moiety may be a 3' reversible or irreversible terminator of polymerase extension. The base of a nucleotide may be any of adenine, cytosine, guanine, thymine, or uracil, or analogs thereof. Optionally, a nucleotide has an inosine, xanthine, hypoxanthine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dUTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP, ddUTP and ddCTP).

As used herein, the "next template nucleotide" (or the "next template base") refers to the next nucleotide (or base) in a template nucleic acid that is located immediately downstream of the 3'-end of a hybridized primer.

As used herein, the term "next correct nucleotide" refers to the nucleotide type that will bind and/or incorporate at the 3' end of a primer to complement a base in a template strand to which the primer is hybridized. The base in the template strand is referred to as the "next template nucleotide" and is immediately 5' of the base in the template that is hybridized to the 3' end of the primer. The next correct nucleotide can be referred to as the "cognate" of the next template nucleotide and vice versa. Cognate nucleotides that interact with each other in a ternary complex or in a double stranded nucleic acid are said to "pair" with each other. A nucleotide having a base that is not complementary to the next template base is referred to as an "incorrect", "mismatch" or "non-cognate" nucleotide.

As used herein, a "blocking moiety," when used with reference to a nucleotide analog, is a part of the nucleotide that inhibits or prevents the nucleotide from forming a covalent linkage to a second nucleotide (e.g., via the 3'-OH of a primer nucleotide) during the incorporation step of a nucleic acid polymerization reaction. The blocking moiety of a "reversible terminator" nucleotide can be removed from the nucleotide analog to allow for nucleotide incorporation. Such a blocking moiety is referred to herein as a "reversible terminator moiety." Exemplary reversible terminator moieties are set forth in U.S. Pat Nos. 7,427,673; 7,414,116; 7,057,026; 7,544,794 and 8,034,923; and PCT publications WO 91/06678 and WO 07/123744, each of which is incorporated by reference.

As used herein, a "test nucleotide" is a nucleotide being investigated for its ability to participate in formation of a ternary complex that further includes a primed template nucleic acid and a polymerase.

As used herein, "polymerase" is a generic term for a protein or other molecule that forms a ternary complex with a cognate nucleotide and primed template nucleic acid (or blocked primed template nucleic acid) including but not limited to, DNA polymerase, RNA polymerase, reverse transcriptase, primase and transferase. Typically, the polymerase includes one or more active sites at which nucleotide binding may occur. Optionally a polymerase includes one or more active sites at which catalysis of nucleotide polymerization may occur. Optionally a polymerase lacks catalytic nucleotide polymerization function, for example, due to a modification such as a mutation or chemical modification. Alternatively, the polymerase may catalyze the polymerization of nucleotides to the 3'-end of a primer bound to its complementary nucleic acid strand. For example, a polymerase catalyzes the addition of a next correct nucleotide to the 3'-OH group of the primer via a phosphodiester bond, thereby chemically incorporating the nucleotide into the primer. Optionally, the polymerase used in the provided methods is a processive polymerase. Optionally, the polymerase used in the provided methods is a distributive polymerase.

As used herein, "biphasic" refers to a two-stage process wherein a primed template nucleic acid is contacted with a polymerase and a test nucleotide. The first phase of the process involves contacting the primed template nucleic acid with a polymerase in the presence of a sub-saturating level of nucleotide(s), or even in the absence of nucleotides. The term "sub-saturating" refers to a concentration below that required for achieving maximal binding at equilibrium. The second phase of the process involves contacting the primed template nucleic acid from the first phase with a polymerase in the presence of a higher concentration of nucleotide(s) than used in the first phase, where the higher concentration is sufficient to yield maximal ternary complex formation when a nucleotide in the reaction is the next correct nucleotide.

As used herein, "providing" a template, a primer, a primed template nucleic acid, or a blocked primed template nucleic acid refers to the preparation or delivery of one or many nucleic acid polymers, for example to a reaction mixture or reaction chamber.

As used herein, "monitoring" (or sometimes "measuring"), when used in reference to a molecular binding event, refers to a process of detecting a measurable interaction or binding between two molecular species. For example, monitoring may involve detecting measurable interactions between a polymerase and primed template nucleic acid (or blocked primed template nucleic acid), typically at various points throughout a procedure. Monitoring can be intermittent (e.g., periodic) or continuous (e.g., without interruption), and can involve acquisition of quantitative results. Monitoring can be carried out by detecting multiple signals over a period of time during a binding event or, alternatively, by detecting signal(s) at a single time point during or after a binding event.

As used herein, "contacting," when used in reference to chemical reagents, refers to the mixing together of reagents (e.g., mixing an immobilized template nucleic acid and either a buffered solution that includes a polymerase, or the combination of a polymerase and a test nucleotide) so that a physical binding reaction or a chemical reaction may take place.

As used herein, "incorporating" or "chemically incorporating" or "incorporation," when used in reference to a nucleic acid and nucleotide, refers to the process of joining a cognate nucleotide to a nucleic acid primer by formation of a phosphodiester bond.

As used herein, a "binary complex" is a complex between a polymerase and a primed template nucleic acid (e.g., blocked primed template nucleic acid), where the complex does not include a nucleotide molecule such as the next correct nucleotide.

As used herein, a "ternary complex" is a complex between a polymerase, a primed template nucleic acid (e.g., blocked primed template nucleic acid), and the next correct nucleotide positioned immediately downstream of the primer and complementary to the template strand of the primed template nucleic acid or the blocked primed template nucleic acid. The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation).

As used herein, a "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at concentrations necessary to stabilize formation of a complex between a polymerase, a nucleotide, and a primed template nucleic acid, referred to as non-catalytic concentrations of a metal ion. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, a "non-catalytic metal ion" refers to a metal ion that, when in the presence of a polymerase enzyme, does not facilitate phosphodiester bond formation needed for chemical incorporation of a nucleotide into a primer. Typically, the non-catalytic metal ion is a cation. A non-catalytic metal ion may inhibit phosphodiester bond formation by a polymerase, and so may stabilize a ternary complex by preventing nucleotide incorporation. Non-catalytic metal ions may interact with polymerases, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein an "exogenous label" refers to a detectable chemical moiety of a sequencing reagent that is not present in a natural analog of the sequencing reagent, such as a non-naturally occurring label present on a synthetic nucleotide analog or a synthetic polymerase analog (e.g., a DNA polymerase). While a native dNTP may have a characteristic limited fluorescence profile, the native dNTP does not include any added colorimetric or fluorescent moiety. Conversely, a dATP (2'-deoxyadenosine-5'-triphosphate) molecule modified to include a chemical linker and fluorescent moiety attached to the gamma phosphate would be said to include an exogenous label because the attached chemical components are not ordinarily a part of the nucleotide. Of course, chemical modifications to add detectable labels to nucleotide bases also would be considered exogenous labels. Likewise, a DNA polymerase modified to include a fluorescent dye (e.g., by attachment to a cys residue that is part of the primary sequence of the enzyme) also would be said to include an exogenous label because the label is not ordinarily a part of the polymerase.

As used herein, "unlabeled" refers to a molecular species free of added or exogenous label(s) or tag(s). Of course, unlabeled nucleotides will not include either of an exogenous fluorescent label, or an exogenous Raman scattering tag. A native nucleotide is another example of an unlabeled molecular species. An unlabeled molecular species can exclude one or more of the labels set forth herein or otherwise known in the art relevant to nucleic acid sequencing or analytical biochemistry.

As used herein, "stabilize," and its grammatical variants mean to hold steady or limit disruption. "Stabilizing" a complex refers to promoting or prolonging the existence of the complex or inhibiting disruption of the complex. The term can be applied to any of a variety of complexes including, but not limited to a binary complex or ternary complex. For example, the complex that is stabilized can be a ternary complex between a polymerase, primed template nucleic acid molecule (or blocked primed template nucleic acid) and cognate nucleotide. Generally, stabilization of the ternary complex prevents incorporation of the nucleotide component of the ternary complex into the primed nucleic acid component of the ternary complex. Accordingly, stabilizing a ternary complex can refer to promoting or prolonging non-covalent interactions that bind components of the ternary complex, or inhibiting disruption of non-covalent interactions that bind components of the ternary complex.

As used herein, the position of the 3' terminal nucleotide of a primer represents position "N" or "n." Thus, "N+1"

refers to the position of the first cognate nucleotide to be incorporated into the primer, while "N+2" refers to the position of the second cognate nucleotide to be incorporated into the primer.

As used herein, "extension" refers to the process after an oligonucleotide primer and a template nucleic acid have annealed to one another, wherein a polymerase enzyme catalyzes addition of one or more nucleotides at the 3'-end of the primer. A nucleotide that is added to a nucleic acid by extension is said to be "incorporated" into the nucleic acid. Accordingly, the term "incorporating" can be used to refer to the process of joining a nucleotide to the 3'-end of a primer by formation of a phosphodiester bond.

The terms "cycle" or "round," when used in reference to a sequencing procedure, refer to the portion of a sequencing run that is repeated to indicate the presence of a nucleotide. Typically, a cycle or round includes several steps such as steps for delivery of reagents, washing away unreacted reagents and detection of signals indicative of changes occurring in response to added reagents.

As used herein, a "ternary complex-stabilizing agent" is any agent that promotes or maintains stability of a ternary complex that includes: either a primed template nucleic acid molecule or a blocked primed template nucleic acid molecule; a polymerase; and a cognate nucleotide (i.e., the next correct nucleotide). Examples include: a non-catalytic metal ion that inhibits enzyme-mediated polymerization (e.g., $Ca^{2+}$, $Zn^{2-}$, $Co^{2-}$, $Ni^{2+}$, and $Sr^{2+}$), including trivalent lanthanide cations (e.g., $Eu^{3+}$ and $Tb^{3-}$); polymerases engineered to have reduced capacity for binary complex formation while exhibiting ternary complex formation capacity; polymerases engineered for complete loss of ability to catalyze phosphodiester bond formation in the presence of $Mg^{2+}$ ion.

As used herein, "destabilize" and its grammatical variants mean to cause something to be unable to continue existing or working in its usual way. "Destabilizing" a complex refers to the process of promoting dissolution or breakdown of the complex (e.g., separation of the components of the complex). "Destabilizing" a complex also includes the process of inhibiting or preventing formation of the complex. The term can be applied to any of a variety of complexes including, but not limited to a binary complex or ternary complex. A ternary complex can be destabilized in a way that does not necessarily result in formation of a covalent bond between a primed template nucleic acid and next correct nucleotide. For example, destabilization can result in dissociation of one or more components from a ternary complex.

As used herein, the "magnitude of ternary complex formation" refers to the measurable amount of a ternary complex that forms, where measurement may involve qualitative assessment of binding curve height or shape; or alternatively quantitative assessment of curve height, time to reach a maximum binding (e.g., "saturation"), a value based on a mathematical curve fitting projection (e.g., related to a projected plateau level), and the like. A higher magnitude of ternary complex formation will indicate a greater number of ternary complexes formed.

Sequencing-by-Binding

Described herein are polymerase-based, nucleic acid sequencing-by-binding (SBB) reactions, wherein the polymerase undergoes conformational transitions between open and closed conformations during discrete steps of the reaction. In one step, the polymerase binds to a primed template nucleic acid to form a binary complex, also referred to herein as the pre-insertion conformation. In a subsequent step, an incoming nucleotide is bound and the polymerase fingers close, forming a pre-chemistry conformation including a polymerase, primed template nucleic acid and nucleotide; wherein the bound nucleotide has not been incorporated. This step, also referred to herein as the "examination" step, may be followed by a chemical step wherein a phosphodiester bond is formed with concomitant pyrophosphate cleavage from the nucleotide (i.e., nucleotide incorporation). The polymerase, primed template nucleic acid and newly incorporated nucleotide produce a post-chemistry, pre-translocation conformation. As both the pre-chemistry conformation and the pre-translocation conformation include a polymerase, primed template nucleic acid and nucleotide, wherein the polymerase is in a closed state, either conformation may be referred to herein as a closed-complex or a closed ternary complex. In the closed pre-insertion state, divalent catalytic metal ions, such as $Mg^{2+}$ mediate a rapid chemical reaction involving nucleophilic displacement of a pyrophosphate (PPi) by the 3' hydroxyl of the primer. The polymerase returns to an open state upon the release of PPi, the post-translocation step, and translocation initiates the next round of reaction. While a closed-complex can form in the absence of divalent catalytic metal ions (e.g., $Mg^{2+}$), the polymerase of the closed-complex is proficient in chemical addition of nucleotide in the presence of the divalent metal ions when provided with an appropriate substrate having an available 3'-hydroxyl group. Low or deficient levels of catalytic metal ions, such as $Mg^{2+}$, lead to non-covalent (e.g., physical) sequestration of the next correct nucleotide in a closed-complex. This closed-complex may be referred to as a stabilized or trapped closed-complex. A stabilized complex can also be formed using a catalytically inactive polymerase mutant or a polymerase that is complexed with a non-catalytic metal ion. Other means for forming a stabilized ternary complex include use of a non-incorporable nucleotide analog or use of a 3' blocked primer in the ternary complex. In any reaction step described above, the polymerase configuration and/or interaction with a nucleic acid may be monitored during an examination step to identify the next correct base in the template nucleic acid sequence. Before or after incorporation, reaction conditions can be changed to disengage the polymerase from the primed template nucleic acid, and changed again to remove from the local environment any reagents that inhibit polymerase binding.

Generally speaking, a procedure disclosed herein can include a series of four or more "examination" steps that assess interaction between a test nucleotide and the next template base, and optionally an "incorporation" step that adds one or more complementary nucleotides (e.g., reversible terminator nucleotides) to the 3'-end of the primer component of the primed template nucleic acid molecule. Identity of the next correct nucleotide to be added is determined either without or before chemical linkage of that nucleotide to the 3'-end of the primer through a covalent bond. The examination step can involve providing a primed template nucleic acid to be used in the procedure, and contacting the primed template nucleic acid with a polymerase enzyme (e.g., a DNA polymerase) and one or more test nucleotides being investigated as the possible next correct nucleotide. Further, there is a step that involves monitoring or measuring the interaction between the polymerase and the primed template nucleic acid in the presence of the test nucleotides. Optionally, the interaction can take place in the presence of stabilizers, whereby the polymerase-nucleic acid interaction is stabilized in the presence of the next correct nucleotide. In some embodiments, the examination steps are capable of identifying or determining the identities of the two next correct nucleotides without requiring incorporation of those nucleotides. Stated differently, identity of the next correct nucleotide, and the subsequent correct nucleotide, can be established without chemical incorporation of any nucleotide into the primer when one or more cycles of examination are carried out using labeled or unlabeled nucleotides.

Whereas methods involving a single template nucleic acid molecule may be described for convenience, these methods are merely illustrative. The sequencing methods provided herein readily encompass a plurality of template nucleic acids, wherein the plurality of nucleic acids may be clonally amplified copies of a single nucleic acid, or disparate nucleic acids, including combinations, such as populations of disparate nucleic acids that are clonally amplified. Thus, such sequencing methods are fully disclosed herein.

The Examination Step

An examination step according to the technique described herein typically includes the following substeps: (1) providing a primed template nucleic acid (i.e., a template nucleic acid molecule hybridized with a primer that optionally may be blocked from extension at its 3'-end); (2) contacting the primed template nucleic acid with a reaction mixture that includes a polymerase and at least one test nucleotide; (3) monitoring the interaction of the polymerase with the primed template nucleic acid molecule in the presence of the nucleotide and without chemical incorporation of any nucleotide into the primed template nucleic acid; (4) repeating the process until binding reactions have been monitored for four different test nucleotides (e.g., dATP, dGTP, dCTP, and either dTTP or dUTP; or nucleotide analogs thereof); and (5) identifying the next two bases in the template nucleic acid (i.e., the next correct nucleotide) using the monitored interactions. Optionally, the primed template nucleic acid molecule can be contacted initially with the polymerase in the absence of nucleotide before contacting any nucleotide. The primer of the primed template nucleic acid can be an extendible primer or a blocked primer. The primed template nucleic acid, the polymerase and the test nucleotide are capable of forming a ternary complex when the base of the test nucleotide is complementary to the next base of the primed template nucleic acid molecule. The primed template nucleic acid and the polymerase are capable of forming a binary complex when the base of the test nucleotide is not complementary to the next base of the primed template nucleic acid molecule. Optionally, the contacting occurs under conditions that favor formation of the ternary complex over formation of the binary complex. The identifying step can include identifying the base of the nucleotide that is complementary to the next base of the primed template nucleic acid. Optionally, this includes contacting ternary complexes with one or more wash solutions having different nucleotide compositions that permit ternary complexes to be selectively maintained or dissociated.

All of these steps can be repeated one or more times to obtain extensive sequence information. For example, ternary complexes can be formed initially by contacting a primed template nucleic acid (optionally including a blocked 3'-end) with a polymerase (optionally labeled with an exogenous label) and, in serial fashion, four different nucleotides (optionally including one or more exogenous labels).

The examination step may be controlled so that nucleotide incorporation is either attenuated or accomplished. If nucleotide incorporation is attenuated during the examination step, then a separate incorporation step may be performed after determining the identity of the next correct nucleotide. The separate incorporation step may be accomplished without the need for monitoring, as the cognate nucleotide has already been identified during the examination step. If nucleotide incorporation proceeds during examination, subsequent nucleotide incorporation may be attenuated by use of a stabilizer that traps the polymerase on the nucleic acid after incorporation. A reversibly terminated nucleotide may also be used to prevent the addition of subsequent nucleotides. The SBB method allows for controlled determination of a template nucleic acid base without requiring the use of labeled nucleotides, as the interaction between the polymerase and template nucleic acid can be monitored without a label on the nucleotide. To be clear, however, the use of a labeled nucleotide (e.g., a fluorescent nucleotide) is optional when performing the presently disclosed procedure to allow for fluorescent detection of bound nucleotide.

In the sequencing methods provided herein, the test nucleotide undergoing examination can include a 3' hydroxyl group, or a blocking moiety that prevents phosphodiester bond formation at the 3'-end of the primer. A 3' terminator moiety or a 2' terminator moiety may be either a reversible terminator or an irreversible terminator. Optionally, a reversible terminator moiety is linked to the base of the 3' nucleotide of the primer strand in the primed template nucleic acid molecule. Optionally, the reversible terminator of the at least one nucleotide molecule is replaced or removed at some point after the examination step that employed the test nucleotide that included the reversible terminator.

Contacting Steps

Contacting of the primed template nucleic acid molecule with reaction mixtures that include the polymerase and one or more test nucleotide molecules can occur under conditions that stabilize formation of the ternary complex and/or destabilize formation of the binary complex. Optionally, the reaction mixture includes potassium glutamate. Optionally, the conditions that stabilize formation of the ternary complex include contacting the primed template nucleic acid with a stabilizing agent. Optionally, the reaction mixture includes a stabilizing agent. The stabilizing agent can be one or more non-catalytic metal ions that inhibit polymerase-mediated incorporation. Exemplary non-catalytic metal ions that inhibit polymerase-mediated incorporation include strontium ion, tin ion, nickel ion, and europium ion. For example, the reaction mixture of the examination step that includes the primed template nucleic acid, the polymerase, and the test nucleotide also may include from 0.01 mM to 30 mM strontium chloride as a stabilizing agent.

Alternatively, and particularly when using a blocked primed template nucleic acid to form a ternary complex in the examination step, reaction mixtures used for conducting examination and monitoring steps optionally can include catalytic metal ions (e.g., $Mg^{2+}$ $Mn^{2+}$). Concentrations of the catalytic metal ions needed to support polymerization activity when using unmodified (i.e., not 3' blocked) primers will be familiar to those having an ordinary level of skill in the art.

In certain embodiments, the primed template nucleic acid is immobilized to the surface of a solid support. The immobilization may employ either a covalent or a noncovalent bond between one or the other, or even both strands of the primed template nucleic acid and the solid support. For example, when the template and primer strands of the primed template nucleic acid are different molecules, the template strand can be immobilized, for example via its 5'-end. What is necessary, however, is that the 3' terminus of the primer is available for interacting with the polymerase.

When the primed template nucleic acid is immobilized to a solid support, there are alternatives for how the contacting steps are performed. For example, the solid support can be physically transferred between different vessels (e.g., individual wells of a multiwell plate) containing different reagent solutions. This is conveniently accomplished using an automated or robotic instrument. In another example, the primed template nucleic acid is immobilized to a solid support inside a flow cell or chamber. In this instance, different contacting steps can be executed by controlled flow of different liquid reagents through the chamber, or across the immobilized primed template nucleic acid.

The Monitoring Step

Monitoring or measuring the interaction of the polymerase with the primed template nucleic acid molecule in the presence of a nucleotide molecule may be accomplished in many different ways. For example, monitoring can include measuring association kinetics for the interaction between the primed template nucleic acid, the polymerase, and a nucleotide. Monitoring the interaction of the polymerase with the primed template nucleic acid molecule in the presence of a nucleotide molecule can include measuring equilibrium binding constants between the polymerase and primed template nucleic acid molecule (i.e., equilibrium binding constants of polymerase to the template nucleic acid in the presence of a nucleotide). Thus, for example, the monitoring includes measuring the equilibrium binding constant of the polymerase to the primed template nucleic acid in the presence of a nucleotide. Monitoring the interaction of the polymerase with the primed template nucleic acid molecule in the presence of a nucleotide molecule includes measuring dissociation kinetics of the polymerase from the primed template nucleic acid in the presence of any one of the four nucleotides. Optionally, monitoring the interaction of the polymerase with the primed template nucleic acid molecule in the presence of a nucleotide molecule includes measuring kinetics of the dissociation of the closed complex (i.e., dissociation of the primed template nucleic acid, the polymerase, and the nucleotide). Optionally, the measured association kinetics differ depending on the identity of the nucleotide molecule. Optionally, the polymerase has a different affinity for each type of nucleotide employed. Optionally, the polymerase has a different dissociation constant for each type of nucleotide in each type of closed-complex. Association, equilibrium and dissociation kinetics are known and can be readily determined by one in the art. See, for example, Markiewicz et al., *Nucleic Acids Research* 40(16):7975-84 (2012); Xia et al., *J. Am. Chem. Soc.* 135 (1):193-202 (2013); Brown et al., *J. Nucleic Acids*, Article ID 871939, 11 pages (2010); Washington, et al., *Mol. Cell. Biol.* 24(2):936-43 (2004); Walsh and Beuning, *J. Nucleic Acids*, Article ID 530963, 17 pages (2012); and Roettger, et al., *Biochemistry* 47(37):9718-9727 (2008), which are incorporated by reference herein in their entireties.

The monitoring step can include monitoring the steady state interaction of the polymerase with the primed template nucleic acid in the presence of a first nucleotide, without chemical incorporation of the first nucleotide into the primer of the primed template nucleic acid. Optionally, monitoring includes monitoring the dissociation of the polymerase from the primed template nucleic acid in the presence of a first nucleotide, without chemical incorporation of the first nucleotide into the primer of the primed template nucleic acid. Optionally, monitoring includes monitoring the association of the polymerase with the primed template nucleic acid in the presence of the first nucleotide, without chemical incorporation of the first nucleotide into the primer of the primed template nucleic acid. Again, test nucleotides in these procedures may be native nucleotides (i.e., unlabeled), labeled nucleotides (e.g., fluorescently labeled nucleotides), or nucleotide analogs (e.g., nucleotides modified to include reversible or irreversible terminator moieties).

In the sequencing methods provided herein, the absence of a catalytic metal ion in the reaction mixture or the absence of a catalytic metal ion in the active site of the polymerase prevents the chemical incorporation of the nucleotide into the primer of the primed template nucleic acid. Optionally, the chelation of a catalytic metal ion in the reaction mixtures of the contacting step prevents the chemical incorporation of the nucleotide into the primer of the primed template nucleic acid. Optionally, a non-catalytic metal ion acts as a stabilizer for the ternary closed-complex in the presence of the next correct nucleotide. Optionally, the substitution of a catalytic metal ion in the reaction mixtures of the contacting step with a non-catalytic metal ion prevents the chemical incorporation of the nucleotide molecule to the primed template nucleic acid. Optionally, the catalytic metal ion is magnesium. The metal ion mechanisms of polymerases postulates that a low concentration of metal ions may be needed to stabilize the polymerase-nucleotide-DNA binding interaction. See, for instance, Section 27.2.2, Berg J M, Tymoczko J L, Stryer L, *Biochemistry 5th Edition*, WH Freeman Press, 2002.

Optionally, a low concentration of a catalytic ion in the reaction mixtures of the examination step (i.e., that are used for binding polymerase in the presence or absence of a test nucleotide) prevents the chemical incorporation of the test nucleotide into the primer of the primed template nucleic acid. Optionally, a low concentration of the catalytic ion (e.g., magnesium ion) is from about 1 $\mu$M to less than 100 $\mu$M. Optionally, a low concentration is from about 0.5 $\mu$M to about 5 $\mu$M. Optionally, the reaction mixtures of the examination step include cobalt, and the incorporating step includes contacting with an incorporation reaction mixture containing a higher concentration of cobalt as compared to the concentration of cobalt in the reaction mixtures of the examination step.

The examination step may be controlled, in part, by providing reaction conditions to prevent chemical incorporation of a nucleotide while allowing monitoring of the interaction between the polymerase and the primed template nucleic acid, thereby permitting determination of the identity of the next base of the nucleic acid template strand. Such reaction conditions may be referred to as "examination reaction conditions." Optionally, a ternary complex or closed-complex is formed under examination conditions. Optionally, a stabilized ternary complex or closed-complex is formed under examination conditions or in a pre-chemistry conformation. Optionally, a stabilized closed-complex is in a pre-translocation conformation, wherein the enclosed nucleotide has been incorporated, but the closed-complex does not allow for the incorporation of a subsequent nucleotide. Optionally, the examination conditions accentuate the difference in affinity for polymerase to primed template nucleic acids in the presence of different nucleotides. Optionally, the examination conditions cause differential affinity of the polymerase to the primed template nucleic acid in the presence of different nucleotides. By way of example, the examination conditions that cause differential affinity of the polymerase to the primed template nucleic acid in the presence of different nucleotides include, but are not limited to, high salt and inclusion of potassium glutamate. Concentrations of potassium glutamate that can be used to alter polymerase affinity for the primed template nucleic acid include 10 mM to 1.6 M of potassium glutamate, or any amount in between 10 mM and 1.6 M. Optionally, high salt refers to a concentration of salt from 50 mM to 1,500 mM salt.

Examination typically involves, in the monitoring step, detecting polymerase interaction with a template nucleic acid, or with template nucleic acid and nucleotide in combination. Detection may include optical, electrical, thermal, acoustic, chemical and mechanical means. Optionally, monitoring is performed after a buffer change or a wash step, wherein the wash step removes any non-bound reagents (e.g., unbound polymerases and/or nucleotides) from the region of observation. Optionally, monitoring is performed during a buffer change or a wash step, such that the dissociation kinetics of the polymerase-nucleic acid or polymerase-nucleic acid-nucleotide complexes may be used to determine the identity of the next base. Optionally, monitoring is performed during the course of addition of the examination reaction mixture or first reaction mixture, such that the association kinetics of the polymerase to the nucleic acid may be used to determine the identity of the next base on the nucleic acid. Optionally, monitoring involves distinguishing closed-complexes from binary complexes of polymerase and primed template nucleic acid. Optionally, monitoring is performed under equilibrium conditions where the affinities measured are equilibrium affinities. Multiple examination steps including different or similar examination reagents, may be performed sequentially to ascertain the identity of the next template base. Multiple examination steps may be utilized in cases where multiple template nucleic acids are being sequenced simultaneously in one sequencing reaction, wherein different nucleic acids react differently to the different examination reagents. Optionally, multiple examination steps may improve the accuracy of next base determination.

In an exemplary sequencing reaction, the examination step includes formation and/or stabilization of a closed-complex including a polymerase, a primed template nucleic acid, and the next correct nucleotide. Characteristics of the formation and/or release of the closed-complex are monitored to identify the enclosed nucleotide and therefore the next base in the template nucleic acid. Closed-complex characteristics can be dependent on the sequencing reaction components (e.g., polymerase, primer, template nucleic acid, nucleotide) and/or reaction mixture components and/or conditions. Optionally, the closed-complex is in a pre-chemistry conformation. Optionally, the closed-complex is in a pre-translocation conformation. Optionally, the closed-complex is in a post-translocation conformation.

The examination step involves monitoring the interaction of a polymerase with a primed template nucleic acid in the presence of a test nucleotide. The formation of a closed-complex may be monitored. Optionally, the absence of formation of a closed-complex is monitored. Optionally, the dissociation of a closed-complex is monitored. Optionally, the incorporation step involves monitoring incorporation of a nucleotide. Optionally, the incorporation step involves monitoring the absence of nucleotide incorporation.

Any process of the examination and/or incorporation step may be monitored. Optionally, a polymerase has an exogenous label or "tag." Optionally, the detectable tag or label on the polymerase is removable. Optionally, the nucleotides or polymerases have a detectable label, however, the label is not detected during sequencing. Optionally, no component of the sequencing reaction is detectably labeled with an exogenous label.

Monitoring the variation in affinity of a polymerase for a template nucleic acid in the presence of correct and incorrect nucleotides, under conditions that may or may not allow the incorporation of the nucleotide, may be used to determine the sequence of the nucleic acid. The affinity of a polymerase for a template nucleic acid in the presence of different nucleotides, including modified or labeled nucleotides, can be monitored as the off-rate of the polymerase-nucleic acid interaction in the presence of the various nucleotides. The affinities and off-rates of many standard polymerases to various matched/correct, mismatched/incorrect and modified nucleotides are known in the art. Single molecule imaging of Klenow polymerase reveals that the off-rate for a template nucleic acid for different nucleotide types, where the nucleotide types are prevented from incorporating, are distinctly and measurably different.

Optionally, a nucleotide of a particular type is made available to a polymerase in the presence of a primed template nucleic acid. The reaction is monitored, wherein, if the nucleotide is a next correct nucleotide, the polymerase may be stabilized to form a closed-complex. If the nucleotide is an incorrect nucleotide, a closed-complex may still be formed; however, without the additional assistance of stabilizing agents or reaction conditions (e.g., absence of catalytic ions, polymerase inhibitors, salt), the closed-complex may dissociate. The rate of dissociation is dependent on the affinity of the particular combination of polymerase, template nucleic acid, and nucleotide, as well as reaction conditions. Optionally, the affinity is measured as an off-rate. Optionally, the affinity is different between different nucleotides for the closed-complex. For example, if the next base in the template nucleic acid downstream of the 3'-end of the primer is G, the polymerase-nucleic acid affinity, measured as an off-rate, is expected to be different based on whether dATP, dCTP, dGTP or dTTP are added. In this case, dCTP would have the slowest off-rate, with the other nucleotides providing different off-rates for the interaction. Optionally, the off-rate may be different depending on the reaction conditions, for example, the presence of stabilizing agents (e.g., absence of magnesium or inhibitory compounds) or reaction conditions (e.g., nucleotide modifications or modified polymerases). Once the identity of the next correct nucleotide is determined, 1, 2, 3, 4 or more nucleotide types may be introduced simultaneously to the reaction mixture under conditions that specifically target the formation of a closed-complex. Excess nucleotides may be removed from the reaction mixture and the reaction conditions modulated to incorporate the next correct nucleotide of the closed-complex. This sequencing reaction ensures that only one nucleotide is incorporated per sequencing cycle.

The affinity of a polymerase for a template nucleic acid in the presence of a nucleotide can be measured in a variety of methods known to one of skill in the art. Optionally, the affinity is measured as an off-rate, where the off-rate is measured by monitoring the release of the polymerase from the template nucleic acid as the reaction is washed by a wash buffer. Optionally, the affinity is measured as an off-rate, where the off-rate is measured by monitoring the release of the polymerase from the template nucleic acid under equilibrium binding conditions, especially equilibrium binding conditions in which the polymerase binding rates are low or diffusion limited. The polymerase binding rates may be diffusion limited at sufficiently low concentrations of polymerase, wherein if the polymerase falls off from the DNA-polymerase complex, it does not load back immediately, allowing for sufficient time to detect that the polymerase has been released from the complex. For a higher affinity interaction, the polymerase is released from the nucleic acid slowly, whereas a low affinity interaction results in the polymerase being released more rapidly. The spectrum of affinities, in this case, translates to different off-rates, with the off-rates measured under dynamic wash conditions or at equilibrium. The smallest off-rate corresponds to the base complementary to the added nucleotide, while the other off-rates vary, in a known fashion, depending on the combination of polymerase and nucleotide selected.

Optionally, the off-rate is measured as an equilibrium signal intensity after the polymerase and nucleotide are provided in the reaction mixture, wherein the interaction with the lowest off-rate (highest affinity) nucleotide produces the strongest signal, while the interactions with other, varying, off-rate nucleotides produce signals of measurably different intensities. As a non-limiting example, a fluorescently labeled polymerase, measured, preferably, under total internal reflection (TIRF) conditions, produces different measured fluorescence intensities depending on the number of polymerase molecules bound to surface-immobilized nucleic acid molecules in a suitably chosen window of time. The intrinsic fluorescence of the polymerase, for instance, tryptophan fluorescence, may also be utilized. A high off-rate interaction produces low measured intensities, as the number of bound polymerase molecules, in the chosen time window is very small, wherein a high off-rate indicates that most of the polymerase is unbound from the nucleic acid. Any surface localized measurement scheme may be employed including, but not limited to, labeled or fluorescence schemes. Suitable measurement schemes that measure affinities under equilibrium conditions include, but are not limited to, bound mass, refractive index, surface charge, dielectric constant, and other schemes known in the art. Optionally, a combination of on-rate and off-rate engineering yields higher fidelity detection in the proposed schemes. As a non-limiting example, a uniformly low on-rate, base-dependent, varying off-rate results in an unbound polymerase remaining unbound for prolonged periods, allowing enhanced discrimination of the variation in off-rate and measured intensity. The on-rate may be manipulated by lowering the concentration of the added polymerase, nucleotide, or both polymerase and nucleotide.

Optionally, the interaction between the polymerase and the nucleic acid is monitored via a detectable tag attached to the polymerase. The tag may be monitored by detection methods including, but limited to, optical, electrical, thermal, mass, size, charge, vibration, and pressure. The label may be magnetic, fluorescent or charged. For external and internal label schemes, fluorescence anisotropy may be used to determine the stable binding of a polymerase to a nucleic acid in a closed-complex.

By way of example, a polymerase is tagged with a fluorophore, wherein ternary complex formation is monitored as a stable fluorescent signal. The unstable interaction of the polymerase with the template nucleic acid in the presence of an incorrect nucleotide results in a measurably weaker signal compared to the closed-complex formed in the presence of the next correct nucleotide. In certain preferred embodiments, however, the sequencing-by-binding procedure does not rely on detection of any exogenous label (e.g., a fluorescent label) joined to the polymerase. For example, the polymerase can be a native polymerase.

Optionally, a primed template nucleic acid molecule (optionally blocked at its 3'-end) is contacted with polymerase and one exogenously labeled nucleotide during each of the four or more examination steps used for each cycle of determining identity of the next two cognate nucleotides. Monitoring of signal generated as a consequence of the presence of the labeled nucleotide provides information concerning formation and stabilization/destabilization of the ternary complex that includes the labeled nucleotide. For example, if the exogenous label is a fluorescent label, and if the primed template nucleic acid is immobilized to a solid support at a particular locus, then monitoring fluorescent signal associated with that locus can be used for monitoring ternary complex formation and stability under different reaction mixture conditions. In some embodiments, a primed template nucleic acid is contacted with a polymerase and a plurality of different exogenously labeled nucleotides. For example, at least 2, 3, 4 or more types of nucleotides can be simultaneously present. Optionally, different labels can be present for nucleotides having different base types, respectively.

The Identifying Step

The identity of the next correct base or nucleotide can be determined by monitoring the presence, formation and/or dissociation of the ternary complex or closed-complex. The identities of the next two bases in the template are determined without chemically incorporating the next correct nucleotide into the 3'-end of the primer. Optionally, the identities of the next two bases are determined by monitoring the affinity of the polymerase for the primed template nucleic acid in the presence of added nucleotides. Optionally, the affinity of the polymerase for the primed template nucleic acid in the presence of the next correct nucleotide may be used to determine the next correct base on the template nucleic acid. Optionally, the affinity of the polymerase for the primed template nucleic acid in the presence of an incorrect nucleotide may be used to determine the next correct base on the template nucleic acid.

In certain embodiments, a ternary complex that includes a primed template nucleic acid (or a blocked primed template nucleic acid) is formed in the presence of a polymerase and a plurality of nucleotides. Cognate nucleotide participating in the ternary complex optionally is identified by observing destabilization of the complex that occurs when the cognate nucleotide is absent from the reaction mixture. This is conveniently carried out, for example, by exchanging one reaction mixture for another. Here, loss of the complex is an indicator of cognate nucleotide identity. Loss of binding signal (e.g., a fluorescent binding signal associated with a particular locus on a solid support) can occur when the primed template nucleic acid is exposed to a reaction mixture that does not include the cognate nucleotide. Optionally, maintenance of a ternary complex in the presence of a single nucleotide in a reaction mixture also can indicate identity of the cognate nucleotide.

The Incorporation Step

Optionally, the methods provided herein further include one or more incorporation steps. By way of example, the incorporation step includes incorporating a single nucleotide (e.g., an unlabeled nucleotide, a reversible terminator nucleotide, or a detectably labeled nucleotide analog) complementary to the next base of the template nucleic acid into the primer of the primed template nucleic acid molecule. Optionally, the incorporation step includes contacting the primed template nucleic acid molecule, polymerase and nucleotide with an incorporation reaction mixture. The incorporation reaction mixture, typically includes a catalytic metal ion.

The provided method may further include preparing the primed template nucleic acid molecule for a next examination step after the incorporation step. Optionally, the preparing includes subjecting the primed template nucleic acid or the nucleic acid/polymerase complex to one or more wash steps; a temperature change; a mechanical vibration; a pH change; salt or buffer composition changes, an optical stimulation or a combination thereof. Optionally, the wash step includes contacting the primed template nucleic acid or the primed template nucleic acid/polymerase complex with one or more buffers, detergents, protein denaturants, proteases, oxidizing agents, reducing agents, or other agents capable of releasing internal crosslinks within a polymerase or crosslinks between a polymerase and nucleic acid.

Optionally, the method further includes repeating the examination step and the incorporation step to sequence a template nucleic acid molecule. The examination step may be repeated one or more times prior to performing the incorporation step. Optionally, two consecutive examination steps include reaction mixtures with different nucleotide molecules (e.g., different nucleotides that are labeled or unlabeled). Optionally, prior to incorporating the single nucleotide into the primed template nucleic acid molecule, the first reaction mixture is replaced with a second reaction mixture including a polymerase and 1, 2, 3, or 4 types of nucleotide molecules (e.g., different unlabeled nucleotides). Optionally, the nucleotide molecules are native nucleotides selected from dATP, dTTP, dCTP, and dGTP.

The incorporation reaction may be enabled by an incorporation reaction mixture. Optionally, the incorporation reaction mixture includes a different composition of nucleotides than the examination reaction. For example, the examination reaction includes one type of nucleotide and the incorporation reaction includes another type of nucleotide. By way of another example, the examination reaction includes one type of nucleotide and the incorporation reaction includes four types of nucleotides, or vice versa. Optionally, the examination reaction mixture is altered or replaced by the incorporation reaction mixture. Optionally, the incorporation reaction mixture includes a catalytic metal ion, potassium chloride, or a combination thereof.

Nucleotides present in the reaction mixture but not sequestered in a closed-complex may cause multiple nucleotide insertions. Thus, a wash step can be employed prior to the chemical incorporation step to ensure only the nucleotide sequestered within a trapped closed-complex is available for incorporation during the incorporation step. Optionally, free nucleotides may be removed by enzymes such as phosphatases. The trapped polymerase complex may be a closed-complex, a stabilized closed-complex or ternary complex involving the polymerase, primed template nucleic acid and next correct nucleotide.

Optionally, the nucleotide enclosed within the closed-complex of the examination step is incorporated into the 3'-end of the template nucleic acid primer during the incorporation step. Optionally, the nucleotide enclosed within the closed-complex of the examination step is incorporated during the examination step, but the closed-complex does not allow for the incorporation of a subsequent nucleotide; in this instance, the closed-complex is released during an incorporation step, allowing for a subsequent nucleotide to become incorporated.

Optionally, the incorporation step includes replacing a nucleotide from the examination step and incorporating another nucleotide into the 3'-end of the template nucleic acid primer. The incorporation step can further involve releasing a nucleotide from within a closed-complex (e.g., the nucleotide is a modified nucleotide or nucleotide analog) and incorporating a nucleotide of a different kind to the 3'-end of the template nucleic acid primer. Optionally, the released nucleotide is removed and replaced with an incorporation reaction mixture including a next correct nucleotide.

Suitable reaction conditions for incorporation may involve replacing the examination reaction mixture with an incorporation reaction mixture. Optionally, nucleotides present in the examination reaction mixture are replaced with one or more nucleotides in the incorporation reaction mixture. Optionally, the polymerase present during the examination step is replaced for the incorporation step. Optionally, the polymerase present during the examination step is modified for the incorporation step. Optionally, the one or more nucleotides present during the examination step are modified for the incorporation step. The reaction mixture and/or reaction conditions present during the examination step may be altered by any means for the incorporation step. These means include, but are not limited to, removing reagents, chelating reagents, diluting reagents, adding reagents, altering reaction conditions such as conductivity or pH, and any combination thereof. The reagents in the reaction mixture including any combination of polymerase, primed template nucleic acid, and nucleotide may be modified during the examination step and/or incorporation step.

Optionally, the reaction mixture of the incorporation step includes competitive inhibitors, wherein the competitive inhibitors reduce the occurrence of multiple incorporations. In certain embodiments, the competitive inhibitor is a non-incorporable nucleotide. In certain embodiments, the competitive inhibitor is an aminoglycoside. The competitive inhibitor is capable of replacing either the nucleotide or the catalytic metal ion in the active site, such that after the first incorporation the competitive inhibitor occupies the active site preventing a second incorporation. In some embodiments, both an incorporable nucleotide and a competitive inhibitor are introduced in the incorporation step, such that the ratio of the incorporable nucleotide and the inhibitor can be adjusted to ensure incorporation of a single nucleotide at the 3'-end of the primer.

Optionally, the provided reaction mixtures, including the incorporation reaction mixtures, include at least one unlabeled nucleotide molecule that is a non-incorporable nucleotide. In other words, the provided reaction mixtures can include one or more unlabeled nucleotide molecules that are incapable of incorporation into the primer of the primed template nucleic acid molecule. Nucleotides incapable of incorporation include, for example, diphosphate nucleotides. For instance, the nucleotide may contain modifications to the triphosphate group that make the nucleotide non-incorporable. Examples of non-incorporable nucleotides may be found in U.S. Pat. No. 7,482,120, the disclosure of which is incorporated by reference herein in its entirety. Optionally, the primer may not contain a free hydroxyl group at its 3'-end, thereby rendering the primer incapable of incorporating any nucleotide, and, thus making any nucleotide non-incorporable.

A polymerase inhibitor optionally may be included with the reaction mixtures containing test nucleotides in the examination step to trap the polymerase on the nucleic acid upon binding the next correct nucleotide. Optionally, the polymerase inhibitor is a pyrophosphate analog. Optionally, the polymerase inhibitor is an allosteric inhibitor. Optionally, the polymerase inhibitor is a DNA or an RNA aptamer. Optionally, the polymerase inhibitor competes with a catalytic-ion binding site in the polymerase. Optionally, the polymerase inhibitor is a reverse transcriptase inhibitor. The polymerase inhibitor may be an HIV-1 reverse transcriptase inhibitor or an HIV-2 reverse transcriptase inhibitor. The HIV-1 reverse transcriptase inhibitor may be a (4/6-halogen/MeO/EtO-substituted benzo[d]thiazol-2-yl)thiazolidin-4-one.

In the provided sequencing methods, the next correct nucleotide is identified before the incorporation step, allowing the incorporation step to not require labeled reagents and/or monitoring. Thus, in the provided methods, a nucleotide, optionally, does not contain an attached detectable tag or label. Optionally, the nucleotide contains a detectable label, but the label is not detected in the method. Optionally, the correct nucleotide does not contain a detectable label; however, an incorrect or non-complementary nucleotide to the next base contains a detectable label. Optionally, the nucleotide contains a detectable label, that is detected during the examination step, however a different nucleotide is incorporated during the incorporation step.

The examination step of the sequencing reaction may be repeated 1, 2, 3, 4 or more times prior to the incorporation step. The examination and incorporation steps may be repeated until the desired sequence of the template nucleic acid is obtained.

The formation of the closed-complex or the stabilized closed-complex can be employed to ensure that only one nucleotide is added to the template nucleic acid primer per cycle of sequencing, wherein the added nucleotide is sequestered within the closed-complex. The controlled incorporation of a single nucleotide per sequencing cycle enhances sequencing accuracy for nucleic acid regions including homopolymer repeats.

Reaction Mixtures

Nucleic acid sequencing reaction mixtures, or simply "reaction mixtures," typically include reagents that are commonly present in polymerase-based nucleic acid synthesis reactions. Reaction mixture reagents include, but are not limited to, enzymes (e.g., the polymerase), dNTPs, template nucleic acids, primer nucleic acids, salts, buffers, small molecules, co-factors, metals, and ions. The ions may be catalytic ions, divalent catalytic ions, non-catalytic ions that inhibit polymerase-mediated incorporation, non-covalent metal ions, or a combination thereof. The reaction mixture can include salts such as NaCl, KCl, potassium acetate, ammonium acetate, potassium glutamate, $NH_4Cl$, or $NH_4HSO_4$. The reaction mixture can include a source of ions, such as $Mg^{2+}$ or $Mn^{2+}$ Mg-acetate, $Co^{2+}$ or $Ba^{2+}$. The reaction mixture can include tin ions, $Ca^{2+}$, $Zn^{2+}$, $Cu^{2+}$, $Co^{2+}$, $Fe^{2+}$, $Ni^{2+}$, or $Eu^{3+}$. The buffer can include Tris, Tricine, HEPES, MOPS, ACES, MES, phosphate-based buffers, and acetate-based buffers. The reaction mixture can include chelating agents such as EDTA, EGTA, and the like. Optionally, the reaction mixture includes cross-linking reagents. Provided herein are reaction mixtures, optionally, used during the examination step, as well as incorporation reaction mixtures used during nucleotide incorporation that can include one or more of the aforementioned agents. Reaction mixtures, when used during examination, can be referred to herein as examination reaction mixtures. Optionally, the examination reaction mixture includes a high concentration of salt; a high pH; 1, 2, 3, 4, or more types of unlabeled nucleotides; potassium glutamate; a chelating agent; a polymerase inhibitor; a catalytic metal ion; a non-catalytic metal ion that inhibits polymerase-mediated incorporation; or any combination thereof. The examination reaction mixture can include 10 mM to 1.6 M of potassium glutamate or any amount in between 10 mM and 1.6 M. Optionally, the incorporation reaction mixture includes a catalytic metal ion; 1, 2, 3, 4, or more types of nucleotides (e.g., unlabeled nucleotides); potassium chloride; a non-catalytic metal ion; or any combination thereof.

Optionally, reaction mixtures in accordance with the disclosed techniques modulate the formation and stabilization of a closed-complex during an examination step. For example, the reaction conditions of the examination step optionally can favor the formation and/or stabilization of a closed-complex encapsulating a nucleotide, and hinder the formation and/or stabilization of a binary complex. The binary interaction between the polymerase and template nucleic acid may be manipulated by modulating sequencing reaction parameters such as ionic strength, pH, temperature, or any combination thereof, or by the addition of a binary complex destabilizing agent to the reaction. Optionally, high salt (e.g., 50 mM to 1,500 mM) and/or pH changes are utilized to destabilize a binary complex. Optionally, a binary complex may form between a polymerase and a template nucleic acid during the examination or incorporation step of the sequencing reaction, regardless of the presence of a nucleotide. Optionally, the reaction conditions favor the stabilization of a closed ternary complex and destabilization of a binary complex. By way of example, the pH of the examination reaction mixture can be adjusted from pH 4.0 to pH 10.0 to favor the stabilization of a ternary complex and destabilization of a binary complex. Optionally, the pH of the examination reaction mixture is from pH 4.0 to pH 6.0. Optionally, the pH of the examination reaction mixture is pH 6.0 to pH 10.0.

The provided reaction mixtures and sequencing methods disclosed herein encourage polymerase interaction with the nucleotides and template nucleic acid in a manner that reveals the identity of the next base while controlling the chemical addition of a nucleotide. Optionally, the methods are performed in the absence of detectably labeled nucleotides or in the presence of labeled nucleotides wherein the labels are not detected. Optionally, the reaction mixtures include nucleotides that harbor an exogenous detectable label (e.g., a fluorescent label). Optionally, a plurality of nucleotides in a reaction mixture harbor the same exogenous detectable label. Optionally, a plurality of nucleotides in a reaction mixture harbor different exogenous detectable labels. Optionally, the reaction mixtures can include one or more exogenously labeled polymerase enzymes.

Provided herein are reaction mixtures and methods that facilitate formation and/or stabilization of a closed-complex that includes a polymerase bound to a primed template nucleic acid and a nucleotide enclosed within the polymerase-template nucleic acid complex, under examination reaction mixture conditions. Examination reaction conditions may inhibit or attenuate nucleotide incorporation. Optionally, incorporation of the enclosed nucleotide is inhibited and the complex is stabilized or trapped in a pre-chemistry conformation or a ternary complex. Optionally, the enclosed nucleotide is incorporated and subsequent nucleotide incorporation is inhibited. In this instance, the complex is stabilized or trapped in a pre-translocation conformation. For the sequencing reactions provided herein, the closed-complex is stabilized during the examination step, allowing for controlled nucleotide incorporation. Optionally, a stabilized closed-complex is a complex wherein incorporation of an enclosed nucleotide is attenuated, either transiently (e.g., to examine the complex and then incorporate the nucleotide) or permanently (e.g., for examination only) during an examination step. Optionally, a stabilized closed-complex allows for the incorporation of the enclosed nucleotide, but does not allow for the incorporation of a subsequent nucleotide. Optionally, the closed complex is stabilized in order to monitor any polymerase interaction with a template nucleic acid in the presence of a nucleotide for identification of the next base in the template nucleic acid.

Optionally, the enclosed nucleotide has severely reduced or disabled binding to the template nucleic acid in the closed-complex. Optionally, the enclosed nucleotide is base-paired to the template nucleic acid at a next base. Optionally, the identity of the polymerase, nucleotide, primer, template nucleic acid, or any combination thereof, affects the interaction between the enclosed nucleotide and the template nucleic acid in the closed-complex.

Optionally, the enclosed nucleotide is bound to the polymerase of the closed complex. Optionally, the enclosed nucleotide is weakly associated with the polymerase of the closed-complex. Optionally, the identity of the polymerase, nucleotide, primer, template nucleic acid, or any combination thereof, affects the interaction between the enclosed nucleotide and the polymerase in the closed-complex. For a given polymerase, each nucleotide has a different affinity for the polymerase than another nucleotide. Optionally, this affinity is dependent, in part, on the template nucleic acid and/or the primer.

The closed-complex may be transiently formed. Optionally, the enclosed nucleotide is a next correct nucleotide. In some methods, the presence of the next correct nucleotide contributes, in part, to the stabilization of a closed-complex. Optionally, the enclosed nucleotide is not a next correct nucleotide.

Optionally, the examination reaction condition comprises a plurality of primed template nucleic acids, polymerases, nucleotides, or any combination thereof. Optionally, the plurality of nucleotides comprises 1, 2, 3, 4, or more types of different nucleotides, for example dATP, dTTP, dGTP, and dCTP. Optionally, the plurality of template nucleic acids is a clonal population of template nucleic acids.

Reaction conditions that may modulate the stability of a closed-complex include, but are not limited to, the availability of catalytic metal ions, suboptimal or inhibitory metal ions, ionic strength, pH, temperature, polymerase inhibitors, cross-linking reagents, and any combination thereof. Reaction reagents which may modulate the stability of a closed-complex include, but are not limited to, non-incorporable nucleotides, incorrect nucleotides, nucleotide analogs, modified polymerases, template nucleic acids with non-extendible polymerization initiation sites, and any combination thereof.

The examination reaction mixture can include other molecules including, but not limited to, enzymes. Optionally, the examination reaction mixture includes any reagents or biomolecules generally present in a nucleic acid polymerization reaction. Reaction components may include, but are not limited to, salts, buffers, small molecules, metals, and ions. Optionally, properties of the reaction mixture may be manipulated, for example, electrically, magnetically, and/or with vibration.

Nucleotides and Nucleotide Analogs

Nucleotides useful for carrying out the sequencing-by-binding procedures described herein include native nucleotides, labeled nucleotides (e.g., nucleotides that include an exogenous fluorescent dye or other label not found in native nucleotides), and nucleotide analogs (e.g., nucleotides having a reversible terminator moiety).

There is flexibility in the nature of the nucleotides that may be employed in connection with the presently described technique. A nucleotide may include as its nitrogenous base any of: adenine, cytosine, guanine, thymine, or uracil. Optionally, a nucleotide includes inosine, xanthine, hypoxanthine, isocytosine, isoguanine, nitropyrrole (including 3-nitropyrrole) or nitroindole (including 5-nitroindole) base. Useful nucleotides include, but are not limited to, ATP, UTP, CTP, GTP, ADP, UDP, CDP, GDP, AMP, UMP, CMP, GMP, dATP, dTTP, dCTP, dGTP, dUTP, dADP, dTDP, dCDP, dGDP, dUDP, dAMP, dTMP, dCMP, dGMP, and dUMP. Optionally, the phosphate group is modified with a moiety. The moiety may include a detectable label. Optionally, the 3' OH group of the nucleotide is modified with a moiety, where the moiety may be a 3' reversible or irreversible terminator moiety. Optionally, the 2' position of the nucleotide is modified with a moiety, where the moiety may be a 2' reversible or irreversible terminator moiety. Optionally, the base of the nucleotide is modified to include a reversible terminator moiety. Nucleotides may also contain terminating inhibitors of DNA polymerase, dideoxynucleotides or 2',3' dideoxynucleotides, which are abbreviated as ddNTPs (ddGTP, ddATP, ddTTP, ddCTP, and ddUTP).

Optionally, a closed-complex of an examination step includes a nucleotide analog or modified nucleotide to facilitate stabilization of the closed-complex. Optionally, a nucleotide analog includes a nitrogenous base, five-carbon sugar, and phosphate group and any component of the nucleotide may be modified and/or replaced. Nucleotide analogs may be non-incorporable nucleotides. Non-incorporable nucleotides may be modified to become incorporable at any point during the sequencing method.

Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein in its entirety.

Nucleotide analogs can include terminators that reversibly prevent attachment of a subsequent nucleotide to the 3'-end of a primer that has been extended with the nucleotide analog. One type of reversible terminator is a 3'-O-blocked reversible terminator. Here the terminator moiety is linked to the oxygen atom of the 3'-OH end of the 5-carbon sugar of a nucleotide. For example, U.S. Pat. Nos. 7,544,794 and 8,034,923 (the disclosures of these patents are incorporated by reference) describe reversible terminator dNTPs having the 3'-OH group replaced by a 3'-ONH$_2$ group. Another type of reversible terminator is a 3'-unblocked reversible terminator, wherein the terminator moiety is linked to the nitrogenous base of a nucleotide. For example, U.S. Pat. No. 8,808,989 (the disclosure of which is incorporated by reference) discloses particular examples of base-modified reversible terminator nucleotides that may be used in connection with the methods described herein. Other reversible terminators that similarly can be used in connection with the methods described herein include those described in U.S. Pat. Nos. 7,956,171, 8,071,755, and 9,399,798 (the disclosures of these U.S. patents are incorporated by reference). For reviews of nucleotide analogs having terminators see e.g., Mu, R., et al., "The History and Advances of Reversible Terminators Used in New Generations of Sequencing Technology," Genomics, Proteomics & Bioinformatics 11(1):34-40 (2013). Optionally, one or more native nucleotides employed during the examination step is replaced by a second type of nucleotide that is incorporated during the incorporation step. For example, nucleotides present in the reaction mixture used during an examination step may be replaced by nucleotide analogs that include reversible terminator moieties (e.g., positioned on the base or sugar of the nucleotide molecule).

Optionally, nucleotides are substituted for modified nucleotide analogs having terminators that irreversibly prevent nucleotide incorporation to the 3'-end of the primers that have incorporated the modified nucleotide analogs. Irreversible nucleotide analogs include dideoxynucleotides, ddNTPs (ddGTP, ddATP, ddTTP, ddCTP). Dideoxynucleotides lack the 3'-OH group of dNTPs that is essential for polymerase-mediated synthesis.

Optionally, non-incorporable nucleotides include a blocking moiety that inhibits or prevents the nucleotide from forming a covalent linkage to a second nucleotide (3' OH of a primer) during the incorporation step of a nucleic acid polymerization reaction. The blocking moiety can be removed from the nucleotide after it has been incorporated into a primer by primer extension, allowing for incorporation of a subsequent nucleotide into the extended primer.

Optionally, a nucleotide analog present in a closed-complex renders the closed-complex stable. Optionally, the nucleotide analog is non-incorporable. Optionally, the nucleotide analog is released and a native nucleotide is incorporated. Optionally, the closed-complex is released, the nucleotide analog is modified, and the modified nucleotide analog is incorporated. Optionally, the closed-complex is released under reaction conditions that modify and/or destabilize the nucleotide analog in the closed-complex.

Optionally, a nucleotide analog present in a closed-complex is incorporated and the closed-complex is stabilized. The closed-complex may be stabilized by the nucleotide analog, or for example, by any stabilizing methods disclosed herein. Optionally, the nucleotide analog does not allow for the incorporation of a subsequent nucleotide. The closed-complex can be released, for example, by any methods described herein, and the nucleotide analog is modified. The modified nucleotide analog may allow for subsequent incorporation of a nucleotide to its 3'-end.

Optionally, a nucleotide analog is present in the reaction mixture during the examination step. For example, 1, 2, 3, 4 or more nucleotide analogs are present in the reaction mixture during the examination step. Optionally, a nucleotide analog is replaced, diluted, or sequestered during an incorporation step. Optionally, a nucleotide analog is replaced with a native nucleotide. The native nucleotide may include a next correct nucleotide. Optionally, a nucleotide analog is modified during an incorporation step. The modified nucleotide analog can be similar to or the same as a native nucleotide.

Optionally, a nucleotide analog has a different binding affinity for a polymerase than a native nucleotide. Optionally, a nucleotide analog has a different interaction with a next base than a native nucleotide. Nucleotide analogs and/or non-incorporable nucleotides may base-pair with a complementary base of a template nucleic acid.

Optionally, a nucleotide analog is a nucleotide, modified or native, fused to a polymerase. Optionally, a plurality of nucleotide analogs includes fusions to a plurality of polymerases, wherein each nucleotide analog includes a different polymerase.

A nucleotide can be modified to favor the formation of a closed complex over the formation of a binary complex. A nucleotide may be selected or modified to have a high affinity for a polymerase, wherein the polymerase binds to a nucleotide prior to binding to the template nucleic acid.

Any nucleotide modification that traps the polymerase in a closed-complex may be used in the methods disclosed herein. The nucleotide may be trapped permanently or transiently. Optionally, the nucleotide analog is not the means by which a closed complex is stabilized. Any closed-complex stabilization method may be combined in a reaction utilizing a nucleotide analog.

Optionally, a nucleotide analog that allows for the stabilization of a closed complex is combined with reaction conditions that usually release the closed-complex. The conditions include, but are not limited to, the presence of a release reagent (e.g., catalytic metal ion, such as magnesium or manganese). Optionally, the closed-complex is stabilized even in the presence of a catalytic metal ion. Optionally, the closed-complex is released even in the presence of a nucleotide analog. Optionally, the stabilization of the closed-complex is dependent, in part, on the concentrations and/or identity of the stabilization reagent and/or release reagents, and any combination thereof. Optionally, the stabilization of a closed-complex using nucleotide analogs is combined with additional reaction conditions that function to stabilize a closed-complex, including, but not limited to, sequestering, removing, reducing, omitting, and/or chelating a catalytic metal ion; the presence of a polymerase inhibitor, cross-linking agent; and any combination thereof.

Optionally, one or more nucleotides can be labeled with distinguishing and/or detectable tags or labels; however, such tags or labels are not detected during examination, identification of the base or incorporation of the base, and are not detected during the sequencing methods disclosed herein. The tags may be distinguishable by means of their differences in fluorescence, Raman spectrum, charge, mass, refractive index, luminescence, length, or any other measurable property. The tag may be attached to one or more different positions on the nucleotide, so long as the fidelity of binding to the polymerase-nucleic acid complex is sufficiently maintained to enable identification of the complementary base on the template nucleic acid correctly. Optionally, the tag is attached to the nucleobase position of the nucleotide. Under suitable reaction conditions, the tagged nucleotides may be enclosed in a closed-complex with the polymerase and the primed template nucleic acid. Alternatively, a tag is attached to the gamma phosphate position of the nucleotide.

Optionally, the labeled nucleotide can include 3-10 or more phosphate groups. Optionally, the labeled nucleotide can be any of adenosine, guanosine, cytidine, thymidine or uridine, or any other type of labeled nucleotide. Optionally, the label can be an energy transfer acceptor reporter moiety. Optionally, the label can be a fluorescent dye. Optionally, the polymerase can be contacted with more than one type of labeled nucleotide (e.g., A, G, C, and/or T/U, or others). Optionally, each type of labeled nucleotides can be operably linked to a different reporter moiety to permit nucleotide identification. Optionally, each type of labeled nucleotide can be operably linked to the same type of reporter moiety. Optionally, the labeled nucleotides are operably linked at the terminal phosphate group with a reporter moiety. Optionally, the labeled nucleotides are operably linked at the base moiety with a reporter moiety. Optionally, the labeled nucleotide can be a non-incorporable nucleotide. Optionally, the non-incorporable nucleotide can bind to the polymerase and primed template nucleic acid molecule in a template-dependent manner, but does not incorporate. Optionally, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/ intensity of transiently-bound complementary and non-complementary nucleotides. Under circumstances involving direct excitation of the reporter moiety, the length of the transient binding time of a complementary nucleotide can be longer and/or more frequent compared to that of a non-complementary nucleotide.

Polymerases

Polymerases useful for carrying out the disclosed sequencing-by-binding technique include naturally occurring polymerases and modified variants thereof, including, but not limited to, mutants, recombinants, fusions, genetic modifications, chemical modifications, synthetics, and analogs. Naturally occurring polymerases and modified variants thereof are not limited to polymerases that retain the ability to catalyze a polymerization reaction. Optionally, the naturally occurring and/or modified variations thereof retain the ability to catalyze a polymerization reaction. Optionally, the naturally occurring and/or modified variations have special properties that enhance their ability to sequence DNA, including enhanced binding affinity to nucleic acids, reduced binding affinity to nucleic acids, enhanced catalysis rates, reduced catalysis rates etc. Mutant polymerases include polymerases wherein one or more amino acids are replaced with other amino acids (naturally or non-naturally occurring), and insertions or deletions of one or more amino acids.

Modified polymerases include polymerases that contain an external tag, which can be used to monitor the presence and interactions of the polymerase. Optionally, intrinsic signals from the polymerase can be used to monitor their presence and interactions. Thus, the provided methods can include monitoring the interaction of the polymerase, nucleotide and template nucleic acid through detection of an intrinsic signal from the polymerase. Optionally, the intrinsic signal is a light scattering signal. For example, intrinsic signals include native fluorescence of certain amino acids such as tryptophan, wherein changes in intrinsic signals from the polymerase may indicate the formation of a ternary-complex. Thus, in the provided methods, the polymerase can be an unlabeled polymerase and monitoring can be performed in the absence of a detectable label associated with the polymerase. Some modified polymerases or naturally occurring polymerases, under specific reaction conditions, may incorporate only single nucleotides and may remain bound to the primer-template after the incorporation of the single nucleotide. Optionally, the thumb and finger domains of the polymerase may form transient or covalent crosslinks due to their physical proximity in the closed form of the polymerase. The crosslinks may be formed, for example by native or engineered cysteines at suitable positions on the thumb and finger domains.

Optionally, the polymerase employed during the examination step includes one or more exogenous detectable label (e.g., a fluorescent label or Raman scattering tag) chemically linked to the structure of the polymerase by a covalent bond. Optionally, the label(s) can be attached after the polymerase has been at least partially purified using protein isolation techniques. For example, the exogenous detectable label can be chemically linked to the polymerase using a free sulfhydryl or a free amine moiety of the polymerase. This can involve chemical linkage to the polymerase through the side chain of a cysteine residue, or through the free amino group of the N-terminus. An exogenous label can also be attached to a polymerase via protein fusion. Exemplary fluorescent labels that can be attached via protein fusion include, for example, Green Fluorescent Protein (and wavelength shifted variants thereof) and phycobiliproteins (e.g., phycocyanin, phycoerythrin and variants thereof). In certain preferred embodiments, a fluorescent label attached to the polymerase is useful for locating the polymerase, as may be important for determining whether or not the polymerase has localized to a feature or spot on an array corresponding to immobilized primed template nucleic acid. The fluorescent signal need not, and preferably does not change absorption or emission characteristics as the result of binding any nucleotide. Stated differently, the signal emitted by the labeled polymerase can be maintained substantially uniformly in the presence and absence of any nucleotide being investigated as a possible next correct nucleotide. In certain other preferred embodiments, the fluorescent signal emitted by the labeled polymerase is differentially affected by inclusion of the polymerase in binary and ternary complexes. Labels useful in this regard are known to those having an ordinary level of skill in the art.

The term polymerase and its variants, as used herein, also refers to fusion proteins including at least two portions linked to each other, for example, where one portion includes a peptide that can catalyze the polymerization of nucleotides into a nucleic acid strand is linked to another portion that includes a second moiety, such as, a reporter enzyme or a processivity-modifying domain. For example, T7 DNA polymerase includes a nucleic acid polymerizing domain and a thioredoxin binding domain, wherein thioredoxin binding enhances the processivity of the polymerase. Absent the thioredoxin binding, T7 DNA polymerase is a distributive polymerase with processivity of only one to a few bases. Although DNA polymerases differ in detail, they have a similar overall shape of a hand with specific regions referred to as the fingers, the palm, and the thumb; and a similar overall structural transition, including the movement of the thumb and/or finger domains, during the synthesis of nucleic acids.

DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, €, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Other DNA polymerases include thermostable and/or thermophilic DNA polymerases such as DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7

DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine *archaea Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated by reference in its entirety.

RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and *Archaea* RNA polymerases.

Reverse transcriptases include, but are not limited to, HIV-1 reverse transcriptase from human immunodeficiency virus type 1 (PDB 1HMV), HIV-2 reverse transcriptase from human immunodeficiency virus type 2, MMLV reverse transcriptase from the Moloney murine leukemia virus, AMV reverse transcriptase from the avian myeloblastosis virus, and telomerase reverse transcriptase that maintains the telomeres of eukaryotic chromosomes.

Optionally, a polymerase is tagged with a chemiluminescent tag, wherein closed complex formation is monitored as a stable luminescence signal in the presence of the appropriate luminescence triggers. The unstable interaction of the polymerase with the template nucleic acid in the presence of an incorrect nucleotide results in a measurably weaker signal compared to the closed-complex formed in the presence of the next correct nucleotide. Additionally, a wash step prior to triggering luminescence could remove all polymerase molecules not bound in a stable closed-complex.

Optionally, a polymerase is tagged with an optical scattering tag, wherein closed-complex formation is monitored as a stable optical scattering signal. The unstable interaction of the polymerase with the nucleic acid in the presence of an incorrect nucleotide results in a measurably weaker signal compared to the closed-complex formed in the presence of the next correct nucleotide.

Optionally, the polymerase is tagged with a plasmonic nanoparticle tag, wherein the closed-complex formation is monitored as a shift in plasmonic resonance that is different from the plasmonic resonance in the absence of the closed-complex or the presence of a closed-complex including an incorrect nucleotide. The change in plasmon resonance may be due to the change in local dielectric environment in the closed-complex, or it may be due to the synchronous aggregation of the plasmonic nanoparticles on a cluster of clonally amplified nucleic acid molecules or another means that affects the plasmons differently in the closed complex configuration.

Optionally, the polymerase is tagged with a Raman scattering tag, wherein the closed-complex formation is monitored as a stable Raman scattering signal. The unstable interaction of polymerase with the nucleic acid in the presence of an incorrect nucleotide results in a measurably weaker signal compared to the closed-complex formed in the presence of the next correct nucleotide.

Optionally, the next two correct nucleotides are identified by a tag on a polymerase selected or modified to have a high affinity for nucleotides, wherein the polymerase binds to a nucleotide prior to binding to the template nucleic acid. For example, the DNA polymerase X from the African Swine Fever virus has an altered order of substrate binding, where the polymerase first binds to a nucleotide, then binds to the template nucleic acid. Optionally, a polymerase is incubated with each type of nucleotide in separate compartments, where each compartment contains a different type of nucleotide and where the polymerase is labeled differently with a tag depending on the nucleotide with which it is incubated. In these conditions, unlabeled nucleotides are bound to differently labeled polymerases. The polymerases may be the same kind of polymerase bound to each nucleotide type or different polymerases bound to each nucleotide type. The differentially tagged polymerase-nucleotide complexes may be added simultaneously to any step of the sequencing reaction. Each polymerase-nucleotide complex binds to a template nucleic acid whose next base is complementary to the nucleotide in the polymerase-nucleotide complex. The next two correct nucleotides are identified by the tag on the polymerase carrying the nucleotides. The interrogation of the next template base by the labeled polymerase-nucleotide complex may be performed under non-incorporating and/or examination conditions, where once the identity of the next template base is determined, the complex is destabilized and removed, sequestered, and/or diluted and a separate incorporation step is performed in a manner ensuring that only one nucleotide is incorporated.

A common method of introducing a detectable tag on a polymerase optionally involves chemical conjugation to amines or cysteines present in the non-active regions of the polymerase. Such conjugation methods are well known in the art. As non-limiting examples, n-hydroxysuccinimide esters (NHS esters) are commonly employed to label amine groups that may be found on an enzyme. Cysteines readily react with thiols or maleimide groups, while carboxyl groups may be reacted with amines by activating them with EDC (1-Ethyl-3-[3-dimethylaminopropyl]carbodiimide hydrochloride). Optionally, N-hydroxysuccinimide (NHS) chemistry is employed at pH ranges where only the N-terminal amines are reactive (for instance, pH 7), such that only a single tag is added per polymerase.

Optionally, the tag attached to the polymerase is a charge tag, such that the formation of stable closed-complex can be detected by electrical means by measuring changes in local charge density around the template nucleic acids. Methods for detecting electrical charges are well known in the art, including methods such as field-effect transistors, dielectric spectroscopy, impedance measurements, and pH measurements, among others. Field-effect transistors include, but are not limited to, ion-sensitive field-effect transistors (ISFET), charge-modulated field-effect transistors, insulated-gate field-effect transistors, metal oxide semiconductor field-effect transistors and field-effect transistors fabricated using semiconducting single wall carbon nanotubes.

Optionally, a charge tag is a peptide tag having an isoelectric point below about 4 or above about 10. Optionally, a polymerase including a peptide tag has a total isoelectric point below about 5 or above about 9. A charge tag may be any moiety which is positively or negatively charged. The charge tag may include additional moieties including mass and/or labels such as dyes. Optionally, the charge tag possesses a positive or negative charge only under certain reaction conditions such as changes in pH.

A polymerase may be labeled with a fluorophore and/or quencher. Optionally, a nucleic acid is labeled with a fluorophore and/or quencher. Optionally, one or more nucleotides are labeled with a fluorophore and/or quencher. Exemplary fluorophores include, but are not limited to, fluorescent nanocrystals; quantum dots; d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorophores include, but are not limited to, MDCC (7-diethylamino-3-[([(2-maleimidyl)ethyl]amino)carbonyl]coumarin), TET, HEX, Cy3, TMR, ROX, Texas Red, Cy5, LC red 705 and LC red 640. Fluorophores and methods for their use including attachment to polymerases and other molecules are described in The Molecular Probes® Handbook (Life Technologies; Carlsbad Calif.) and Fluorophores Guide (Promega; Madison, Wis.), which are incorporated herein by reference in their entireties. Exemplary quenches include, but are not limited to, ZEN, IBFQ, BHQ-1, BHQ-2, DDQ-I, DDQ-11, Dabcyl, Qx1 quencher, Iowa Black RQ, and IRDye QC-1.

Optionally, a conformationally sensitive dye may be attached close to the active site of the polymerase without adversely affecting the polymerization ability or fidelity of the polymerase; wherein a change in conformation, or a change in polar environment due to the formation of a closed-complex is reflected as a change in fluorescence or absorbance properties of the dye. Common fluorophores such as Cy3 and fluorescein are known to have strong solvatochromatic response to polymerase binding and closed-complex formation, to the extent that the formation of closed-complex can be distinguished clearly from the binary polymerase-nucleic acid complex. Optionally, the closed-complex can be distinguished from binary complexes based on differences in fluorescence or absorbance signals from a conformationally sensitive dye. Optionally, a solvatochromatic dye may be employed to monitor conformational transitions; wherein the change in local polar environment induced by the conformational change can be used as the reporter signal. Solvatochromatic dyes include, but are not limited to, Reichart's dye, IR44, merocyanine dyes (e.g., merocyanine 540), 4-[2-N-substituted-1,4-hydropyridin-4-ylidine)ethylidene]cyclohexa-2,5-dien-1-one, red pyrazolone dyes, azomethine dyes, indoaniline dyes, diazamerocyanine dyes, indigoid dyes, as exemplified by indigo, and others as well as mixtures thereof. Methods to introduce dyes or fluorophores to specific sites of a polymerase are well known in the art. As a non-limiting example, a procedure for site specific labeling of a T7 DNA polymerase with a dye is provided by Tsai et al., in "Site-Specific Labeling of T7 DNA Polymerase with a Conformationally Sensitive Fluorophore and Its Use in Detecting Single-Nucleotide Polymorphisms," *Analytical Biochemistry* 384: 136-144 (2009), which is incorporated by reference herein in its entirety.

Optionally, a polymerase is tagged with a fluorophore at a position that could sense closed-complex formation without interfering with the reaction. The polymerase may be a native or modified polymerase. Modified polymerases include those with one or more amino acid mutations, additions, and/or deletions. Optionally, one or more, but not all, cysteine amino acids are mutated to another amino acid, such as alanine. In this case, the remaining one or more cysteines are used for site-specific conjugation to a fluorophore. Alternatively, one or more amino acids are mutated to a reactive amino acid suitable for fluorophore conjugation, such as cysteines or amino acids including primary amines.

Optionally, binding between a polymerase and a template nucleic acid in the presence of a correct nucleotide may induce a decrease in fluorescence, whereas binding with an incorrect nucleotide causes an increase in fluorescence. Binding between a polymerase and a template nucleic acid in the presence of a correct nucleotide may induce an increase in fluorescence, whereas binding with an incorrect nucleotide causes a decrease in fluorescence. The fluorescent signals may be used to monitor the kinetics of a nucleotide-induced conformational change and identify the next base in the template nucleic acid sequence.

Optionally, the polymerase/nucleic-acid interaction may be monitored by scattering signal originating from the polymerase or tags attached to the polymerase, for instance, nanoparticle tags.

Conditions for Forming and Manipulating Closed-Complexes

As used herein, a closed-complex can be a ternary complex that includes a polymerase, primed template nucleic acid, and nucleotide. The closed-complex may be in a pre-chemistry conformation, wherein a nucleotide is sequestered but not incorporated. The closed-complex may alternatively be in a pre-translocation conformation, wherein a nucleotide is incorporated by formation of a phosphodiester bond with the 3'-end of the primer in the primed template nucleic acid. The closed-complex may be formed in the absence of catalytic metal ions or deficient levels of catalytic metal ions, thereby physically sequestering the next correct nucleotide within the polymerase active site without chemical incorporation. Optionally, the sequestered nucleotide may be a non-incorporable nucleotide. The closed-complex may be formed in the presence of catalytic metal ions, where the closed-complex includes a nucleotide analog which is incorporated, but a PPi is not capable of release. In this instance, the closed-complex is stabilized in a pre-translocation conformation. Optionally, a pre-translocation conformation is stabilized by chemically cross-linking the polymerase. Optionally, the closed-complex may be stabilized by external means. In some instances, the closed-complex may be stabilized by allosteric binding of small molecules, or macromolecules such as antibodies or aptamers. Optionally, closed-complex may be stabilized by pyrophosphate analogs that bind close to the active site with high affinity, preventing translocation of the polymerase.

As used herein, a stabilized closed-complex or stabilized ternary complex refers to a polymerase trapped at the polymerization initiation site (3'-end of the primer) of the primed template nucleic acid by one or a combinations of means, including but not limited to, crosslinking the thumb and finger domains in the closed conformation, binding of an allosteric inhibitor that prevents return of the polymerase to an open conformation, binding of pyrophosphate analogs that trap polymerase in the pre-translocation step, absence of catalytic metal ions in the active site of the polymerase, and addition of a metal ions such as nickel, tin and $Sr^{2+}$ as substitutes for a catalytic metal ion. As such, the polymerase may be trapped at the polymerization initiation site even after the incorporation of a nucleotide. Therefore, the polymerase may be trapped in the pre-chemistry conformation, pre-translocation step, post-translocation step or any intermediate step thereof. Thus, allowing for sufficient examination and identification of the next correct nucleotide or base.

As described herein, a polymerase-based, sequencing-by-binding reaction generally involves providing a primed template nucleic acid with a polymerase and one or more of four different nucleotides in a serial fashion, wherein the nucleotides may or may not be complementary to the next base of the primed template nucleic acid, and examining the interaction of the polymerase with the primed template nucleic acid under conditions wherein chemical incorporation of a nucleotide into the primed template nucleic acid is disabled or severely inhibited in the pre-chemistry conformation. Optionally, wherein the pre-chemistry conformation is stabilized prior to nucleotide incorporation, preferably using stabilizers, a separate incorporation step may follow the examination step to incorporate a single nucleotide to the 3'-end of the primer. Optionally, where a single nucleotide incorporation occurs, the pre-translocation conformation may be stabilized to facilitate examination and/or prevent subsequent nucleotide incorporation.

As indicated above, the presently described methods for sequencing a nucleic acid include an examination step. The examination step involves binding a polymerase to the polymerization initiation site of a primed template nucleic acid in a reaction mixture including at least one of four different nucleotides in a serial fashion, and monitoring the interaction. Optionally, a nucleotide is sequestered within the polymerase-primed template nucleic acid complex to form a closed-complex, under conditions in which incorporation of the enclosed nucleotide by the polymerase is attenuated or inhibited. Optionally a stabilizer is added to stabilize the ternary complex in the presence of the next correct nucleotide. This closed-complex is in a stabilized or polymerase-trapped pre-chemistry conformation. A closed-complex allows for the incorporation of the enclosed nucleotide but does not allow for the incorporation of a subsequent nucleotide. This closed-complex is in a stabilized or trapped pre-translocation conformation. Optionally, the polymerase is trapped at the polymerization site in its closed-complex by one or a combination of means including, but not limited to, crosslinking of the polymerase domains, crosslinking of the polymerase to the nucleic acid, allosteric inhibition by small molecules, uncompetitive inhibitors, competitive inhibitors, non-competitive inhibitors, and denaturation; wherein the formation of the trapped closed-complex provides information about the identity of the next base on the nucleic acid template.

Optionally, a closed-complex is released from its trapped or stabilized conformation, which may allow for nucleotide incorporation to the 3'-end of the template nucleic acid primer. The closed-complex can be destabilized and/or released by modulating the composition of the reaction conditions. In addition, the closed-complex can be destabilized by electrical, magnetic, and/or mechanical means. Mechanical means include mechanical agitation, for example, by using ultrasound agitation. Mechanical vibration destabilizes the closed complex and suppresses binding of the polymerase to the DNA. Thus, rather than a wash step where the examination reaction mixture is replaced with an incorporation mixture, mechanical agitation may be used to remove the polymerase from the template nucleic acid, enabling cycling through successive incorporation steps with a single nucleotide addition per step.

Any combination of closed-complex stabilization or closed-complex release reaction conditions and/or methods may be combined. For example, a polymerase inhibitor that stabilizes a closed-complex may be present in the examination reaction with a catalytic ion, which functions to release the closed-complex. In the aforementioned example, the closed complex may be stabilized or released, depending on the polymerase inhibitor properties and concentration, the concentration of the catalytic metal ion, other reagents and/or conditions of the reaction mixture, and any combination thereof.

The closed-complex can be stabilized under reaction conditions where covalent attachment of a nucleotide to the 3'-end of the primer in the primed template nucleic acid is attenuated. Optionally, the closed-complex is in a pre-chemistry conformation or ternary complex. Optionally, the closed-complex is in a pre-translocation conformation. The formation of this closed-complex can be initiated and/or stabilized by modulating the availability of a catalytic metal ion that permits closed-complex release and/or chemical incorporation of a nucleotide to the primer in the reaction mixture. Exemplary metal ions include, but are not limited to, magnesium, manganese, cobalt, and barium. Catalytic ions may be any formulation, for example, salts such as $MgCl_2$, $Mg(CH_3CO_2)_2$, and $MnCl_2$.

The selection and/or concentration of the catalytic metal ion may be based on the polymerase and/or nucleotides in the sequencing reaction. For example, the HIV reverse transcriptase utilizes magnesium for nucleotide incorporation (N Kaushik, *Biochemistry* 35:11536-11546 (1996), and H P Patel, *Biochemistry* 34:5351-5363 (1995), which are incorporated by reference herein in their entireties). The rate of closed-complex formation using magnesium versus manganese can be different depending on the polymerase and the identity of the nucleotide. Thus, the stability of the closed complex may differ depending on catalytic metal ion, polymerase, and/or nucleotide identity. Further, the concentration of catalytic ion necessary for closed-complex stabilization may vary depending on the catalytic metal ion, polymerase, and/or nucleotide identity and can be readily determined using the guidance provided herein. For example, nucleotide incorporation may occur at high catalytic ion concentrations of one metal ion but does not occur at low concentrations of the same metal ion, or vice versa. Therefore, modifying metal ion identity, metal ion concentration, polymerase identity, and/or nucleotide identity allows for controlled examination reaction conditions.

The closed-complex may be formed and/or stabilized by sequestering, removing, reducing, omitting, and/or chelating a catalytic metal ion during the examination step of the sequencing reaction so that closed-complex release and/or chemical incorporation does not occur. Chelation includes any procedure that renders the catalytic metal ion unavailable for nucleotide incorporation, including using EDTA and/or EGTA. A reduction includes diluting the concentration of a catalytic metal ion in the reaction mixture. The reaction mixture can be diluted or replaced with a solution including a non-catalytic metal ion, which permits closed-complex formation, but inhibits nucleotide incorporation. Non-catalytic ions that inhibit polymerase-mediated incorporation include, but are not limited to, calcium, strontium, scandium, titanium, vanadium, chromium, iron, cobalt, nickel, copper, zinc, gallium, germanium, arsenic, selenium, rhodium, and strontium. Optionally, $Ni^{2+}$ is provided in an examination reaction to facilitate closed-complex formation. Optionally, $Sr^{2+}$ is provided in an examination reaction to facilitate closed-complex formation. Optionally, a non-catalytic metal ion and a catalytic metal ion are both present in the reaction mixture, wherein one ion is present in a higher effective concentration than the other. In the provided methods, a non-catalytic ion such as cobalt can become catalytic (i.e., facilitate nucleotide incorporation) at high concentrations. Thus, optionally, a low concentration of a non-catalytic metal ion is used to facilitate ternary complex formation and a higher concentration of the non-catalytic metal ion is used to facilitate incorporation.

Non-catalytic ions that inhibit polymerase-mediated incorporation may be added to a reaction mixture under examination conditions. The reaction may already include nucleotides. Optionally, non-catalytic ions are complexed to one or more nucleotides, and complexed nucleotides are added to the reaction mixture. Non-catalytic ions can complex to nucleotides by mixing nucleotides with non-catalytic ions at elevated temperatures (about 80° C.). For example, a chromium nucleotide complex may be added to a mixture to facilitate closed-complex formation and stabilization. Optionally, a chromium nucleotide complex is a chromium monodentate, bidentate, or tridentate complex. Optionally, a chromium nucleotide complex is an α-monodentate, or β-γ-bidentate nucleotide.

Optionally, a closed-complex is formed between a polymerase, primed template nucleic acid, and nucleotide in reaction conditions including $Sr^{2+}$, wherein $Sr^{2+}$ promotes the formation of the closed-complex. The presence of $Sr^{2+}$ can allow for the favorable formation of a closed-complex including a next correct nucleotide over the formation a complex including an incorrect nucleotide. The $Sr^{2+}$ ion may be present at concentrations from about 0.01 mM to about 30 mM. Optionally, $Sr^{2+}$ is present as 10 mM $SrCl_2$. The formation of the closed-complex is monitored under examination conditions to identify the next base in the template nucleic acid of the closed-complex. The affinity of the polymerase (e.g., Klenow fragment of E. coli DNA polymerase I, Bst) for each of the dNTPs (e.g., dATP, dTTP, dCTP, dGTP) in the presence of $Sr^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilize the ternary interactions between the polymerase, the primed template nucleic acid, and the next correct nucleotide. After examination, a wash step removes unbound nucleotides, and $Mg^{2+}$ is added to the reaction to induce pyrophosphate (PPi) cleavage and nucleotide incorporation. Optionally, the wash step includes $Sr^{2+}$ to maintain the stability of the ternary complex, preventing the dissociation of the ternary complex. The reaction may be repeated until a desired sequence read length is obtained.

Optionally, a closed-complex is formed between a polymerase, primed template nucleic acid, and nucleotide in reaction conditions including $Ni^{2-}$, wherein $Ni^{2+}$ promotes the formation of the closed-complex. The presence of $Ni^{2+}$ can allow for the favorable formation of a closed-complex including a next correct nucleotide over the formation a complex including an incorrect nucleotide. The $Ni^{2+}$ ion may be present at concentrations from about 0.01 mM to about 30 mM. Optionally, $Ni^{2+}$ is present as 10 mM $NiCl_2$. The formation of the closed-complex is monitored under examination conditions to identify the next base in the template nucleic acid of the closed-complex. The affinity of the polymerase (e.g., Klenow fragment of E. coli DNA polymerase I, Bst) for each of the dNTPs (e.g., dATP, dTTP, dCTP, dGTP) in the presence of $Sr^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilize the ternary interactions between the polymerase, the primed template nucleic acid, and the next correct nucleotide. After examination, a wash removes unbound nucleotides and polymerase, and $Mg^{2+}$ is added to the reaction to induce pyrophosphate (PPi) cleavage and nucleotide incorporation. Optionally, the wash buffer includes $Ni^{2+}$ to maintain the stability of the ternary complex, preventing the dissociation of the ternary complex. The reaction may be repeated until a desired sequence read length is obtained.

Optionally, a closed-complex is formed between a polymerase, primed template nucleic acid, and nucleotide in reaction conditions including non-catalytic concentrations of $Co^{2+}$, wherein $Co^{2+}$ promotes the formation of the closed-complex. The presence of non-catalytic concentrations of $Co^{2+}$ can allow for the favorable formation of a closed-complex including a next correct nucleotide over the formation a complex including an incorrect nucleotide. The $Co^{2+}$ ion may be present at concentrations from about 0.01 mM to about 0.5 mM. Optionally, $Co^{2+}$ is present as 0.5 mM $CoCl_2$. The formation of the closed-complex is monitored under examination conditions to identify the next base in the template nucleic acid of the closed-complex. The affinity of the polymerase (e.g., Klenow fragment of E. coli DNA polymerase I, Bst) for each of the dNTPs (e.g., dATP, dTTP, dCTP, dGTP) in the presence of $Co^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilize the ternary interactions between the polymerase, the primed template nucleic acid, and the next correct nucleotide. After examination, a wash removes unbound nucleotides and polymerase, and $Co^{2+}$ at a catalytic concentration is added to the reaction to induce pyrophosphate (PPi) cleavage and nucleotide incorporation. Optionally, the wash buffer includes non-catalytic amounts of $Co^{2+}$ to maintain the stability of the ternary complex, preventing the dissociation of the ternary complex. The reaction may be repeated until a desired sequence read length is obtained.

Optionally, a catalytic metal ion may facilitate the formation of a closed complex without subsequent nucleotide incorporation and closed-complex release. Optionally, a concentration of 0.5, 1, 2, 3, 4, 5, 6, 7, 8, 9, or 10 μM $Mg^{2+}$ in a reaction mixture can induce conformational change of a polymerase to form a closed-complex without subsequent nucleotide incorporation, PPi and closed-complex release. Optionally, the concentration of $Mg^{2+}$ is from about 0.5 μM to about 10 μM, from about 0.5 μM to about 5 μM, from about 0.5 μM to about 4 μM, from about 0.5 μM to about 3 μM, from about μM to about 5 μM, from about 1 μM to about 4 μM, and from about 1 μM to about 3 μM.

Optionally, the concentration of available catalytic metal ion in the sequencing reaction which is necessary to allow nucleotide incorporation is from about 0.001 mM to about 10 mM, from about 0.01 mM to about 5 mM, from about 0.01 mM to about 3 mM, from about 0.01 mM to about 2 mM, from about 0.01 mM to about 1 mM, from about 0.05 mM to about 10 mM, from about 0.05 mM to about 5 mM, from about 0.05 mM to about 3 mM, from about 0.05 to about 2 mM, or from about 0.05 mM to about 1 mM. Optionally, the concentration of catalytic metal ion is from 5 mM to 50 mM. Optionally, the concentration of catalytic metal ion is from 5 mM to 15 mM, or about 10 mM.

A non-catalytic ion that inhibits polymerase-mediated incorporation may be added to the reaction mixture at any stage including before, during, or after any of the following reaction steps: providing a primed template nucleic acid, providing a polymerase, formation of a binary complex, providing a nucleotide, formation of a pre-chemistry closed-complex, nucleotide incorporation, formation of a pre-translocation closed-complex, and formation of a post-translocation conformation. The non-catalytic ion may be added to the reaction mixture during wash steps. The non-catalytic ion may be present through the reaction in the reaction mixture. For example, a catalytic ion is added to the reaction mixture at concentrations which dilute the non-catalytic metal ion, allowing for nucleotide incorporation.

The ability of catalytic and non-catalytic ions to modulate nucleotide incorporation may depend on conditions in the reaction mixture including, but not limited to, pH, ionic strength, chelating agents, chemical cross-linking, modified polymerases, non-incorporable nucleotides, mechanical or vibration energy, and electric fields.

Optionally, the concentration of non-catalytic metal ion in the sequencing reaction necessary to allow for closed-complex formation without nucleotide incorporation is from about 0.1 mM to about 50 mM, from about 0.1 mM to about 40 mM, from about 0.1 mM to about 30 mM, from about 0.1 mM to about 20 mM, from about 0.1 mM to about 10 mM, from about 0.1 mM to about 5 mM, from about 0.1 to about 1 mM, from about 1 mM to about 50 mM, from about 1 to about 40 mM, from about 1 mM to about 30 mM, from about 1 mM to about 20 mM, from about 1 mM to about 10 mM, from about 1 mM to about 5 mM, from about 2 mM to about 30 mM, from about 2 mM to about 20 mM, from about 2 mM to about 10 mM, or any concentration within these ranges.

A closed-complex may be formed and/or stabilized by the addition of a polymerase inhibitor to the examination reaction mixture. Inhibitor molecules phosphonoacetate (phosphonoacetic acid) and phosphonoformate (phosphonoformic acid, common name Foscarnet), Suramin, Aminoglycosides, INDOPY-1 and Tagetitoxin are non-limiting examples of uncompetitive or noncompetitive inhibitors of polymerase activity. The binding of the inhibitor molecule, near the active site of the enzyme, traps the polymerase in either a pre-translocation or post-translocation step of the nucleotide incorporation cycle, stabilizing the polymerase in its closed-complex conformation before or after the incorporation of a nucleotide, and forcing the polymerase to be bound to the template nucleic acid until the inhibitor molecules are not available in the reaction mixture by removal, dilution or chelation.

Thus, provided is a method for sequencing a template nucleic acid molecule that includes a series of examination steps, each including providing a template nucleic acid molecule primed with a primer; contacting the primed template nucleic acid molecule with a first reaction mixture including a polymerase, a polymerase inhibitor and at least one unlabeled nucleotide molecule; monitoring the interaction of the polymerase with the primed template nucleic acid molecule in the presence of the unlabeled nucleotide molecule without incorporation of the nucleotide into the primer of the primed template nucleic acid molecule; and identifying the nucleotide that is complementary to the next base of the primed template nucleic acid molecule by the monitored interaction. The polymerase inhibitor prevents the incorporation of the unlabeled nucleotide molecule into the primer of the primer template nucleic acid. Optionally, the inhibitor is a non-competitive inhibitor, an allosteric inhibitor, or an uncompetitive allosteric inhibitor. Optionally, the polymerase inhibitor competes with a catalytic ion binding site in the polymerase.

Detection Platforms: Instrumentation for Detecting the Closed-Complex

The interaction between the polymerase and the template nucleic acid in the presence of nucleotides can be monitored with or without the use of an exogenous label. For example, the sequencing reaction may be monitored by detecting the change in refractive index, fluorescence emission, charge detection, Raman scattering detection, ellipsometry detection, pH detection, size detection, mass detection, surface plasmon resonance, guided mode resonance, nanopore optical interferometry, whispering gallery mode resonance, nanoparticle scattering, photonic crystal, quartz crystal microbalance, bio-layer interferometry, vibrational detection, pressure detection and other label-free detection schemes that detect the added mass or refractive index due to polymerase binding in a closed-complex with a template nucleic acid.

Optionally, detecting a change in refractive index is accomplished by one or a combination of means, including, but not limited to, surface plasmon resonance sensing, localized plasmon resonance sensing, plasmon-photon coupling sensing, transmission sensing through sub-wavelength nanoholes (enhanced optical transmission), photonic crystal sensing, interferometry sensing, refraction sensing, guided mode resonance sensing, ring resonator sensing, or ellipsometry sensing. Optionally, nucleic acid molecules may be localized to a surface, wherein the interaction of polymerase with nucleic acids in the presence of various nucleotides may be measured as a change in the local refractive index.

Optionally, the template nucleic acid is tethered to or localized appropriately on or near a surface, such that the interaction of polymerase and template nucleic acid in the presence of nucleotides changes the light transmitted across or reflected from the surface. The surface may contain nanostructures. Optionally, the surface is capable of sustaining plasmons or plasmon resonance. Optionally, the surface is a photonic substrate, not limited to a resonant cavity, resonant ring or photonic crystal slab. Optionally, the surface is a guided mode resonance sensor. Optionally, the nucleic acid is tethered to, or localized appropriately on or near a nanohole array, a nanoparticle or a microparticle, such that the interaction of polymerase and template nucleic acid in the presence of nucleotides changes the absorbance, scattering, reflection or resonance of the light interacting with the microparticle or nanoparticle.

Optionally, a nanohole array on a gold surface is used as a refractive index sensor. The template nucleic acid may be attached to a metal surface by standard thiol chemistry, incorporating the thiol group on one of the primers used in a PCR reaction to amplify the DNA. When the dimensions of the nanohole array are appropriately tuned to the incident light, binding of the polymerase to the template nucleic acid in the presence of nucleotides can be monitored as a change in light transmitted across the nanoholes. For both the labeled and label-free schemes, simple and straightforward measurement of equilibrium signal intensity may reveal the formation of a stable closed complex.

Optionally, nucleic acid molecules are localized to a surface capable of sustaining surface plasmons, wherein the change in refractive index caused by the polymerase interaction with localized nucleic acids may be monitored through the change in the properties of the surface plasmons, wherein further, said properties of surface plasmons may include surface plasmon resonance. Surface plasmons, localized surface plasmons (LSP), or surface plasmon polaritons (SPP), arise from the coupling of electromagnetic waves to plasma oscillations of surface charges. LSPs are confined to nanoparticle surfaces, while SPPs and are confined to high electron density surfaces, at the interface between high electron mobility surfaces and dielectric media. Surface plasmons may propagate along the direction of the interface, whereas they penetrate into the dielectric medium only in an evanescent fashion. Surface plasmon resonance conditions are established when the frequency of incident electromagnetic radiation matches the natural frequency of oscillation of the surface electrons. Changes in dielectric properties at the interface, for instance due to binding or molecular crowding, affects the oscillation of surface electrons, thereby altering the surface plasmon resonance wavelength. Surfaces capable of surface plasmon resonance include, in a non-limiting manner, nanoparticles, clusters and aggregates of nanoparticles, continuous planar surfaces, nanostructured surfaces, and microstructured surfaces. Materials such as gold, silver, aluminum, high conductivity metal oxides (e.g., indium tin oxide, zinc oxide, tungsten oxide) are capable of supporting surface plasmon resonance at their surfaces.

Optionally, a single nucleic acid molecule, or multiple clonal copies of a nucleic acid, are attached to a nanoparticle, such that binding of polymerase to the nucleic acid causes a shift in the localized surface plasmon resonance (LSPR). Light incident on the nanoparticles induces the conduction electrons in them to oscillate collectively with a resonant frequency that depends on the nanoparticles' size, shape and composition. Nanoparticles of interest may assume different shapes, including spherical nanoparticles, nanorods, nanopyramids, nanodiamonds, and nanodiscs. As a result of these LSPR modes, the nanoparticles absorb and scatter light so intensely that single nanoparticles are easily observed by eye using dark-field (optical scattering) microscopy. For example, a single 80-nm silver nanosphere scatters 445-nm blue light with a scattering cross-section of $3 \times 10^{-2}$ m$^2$, a million-fold greater than the fluorescence cross-section of a fluorescein molecule, and a thousand fold greater than the cross-section of a similarly sized nanosphere filled with fluorescein to the self-quenching limit. Optionally, the nanoparticles are plasmon-resonant particles configured as ultra-bright, nanosized optical scatters with a scattering peak anywhere in the visible spectrum. Plasmon-resonant particles are advantageous as they do not bleach. Optionally, plasmon-resonant particles are prepared, coated with template nucleic acids, and provided in a reaction mixture including a polymerase and one or more nucleotides, wherein a polymerase-template nucleic acid-particle interaction is detected. One or more of the aforementioned steps may be based on or derived from one or more methods disclosed by Schultz et al., in *PNAS* 97:996-1001 (2000), which is incorporated by reference herein in its entirety.

The very large extinction coefficients at resonant wavelength enables noble-metal nanoparticles to serve as extremely intense labels for near-surface interactions. Optionally, polymerase interaction with nanoparticle-localized DNA results in a shift in the resonant wavelength. The change in resonant wavelength due to binding or binding interactions can be measured in one of many ways. Optionally, the illumination is scanned through a range of wavelengths to identify the wavelength at which maximum scattering is observed at an imaging device. Optionally, broadband illumination is utilized in conjunction with a dispersive element near the imaging device, such that the resonant peak is identified spectroscopically. Optionally, the nanoparticle system may be illuminated at its resonant wavelength, or near its resonant wavelength, and any binding interactions may be observed as a drop in intensity of light scattered as the new resonant wavelength shifts away from the illumination wavelength. Depending on the positioning of the illuminating wavelength, interactions may even appear as an increase in nanoparticle scattering as the resonance peak shifts towards the illumination wavelength. Optionally, DNA-attached-nanoparticles may be localized to a surface, or, alternatively, the DNA-attached-nanoparticles may be suspended in solution. A comprehensive review of biosensing using nanoparticles is described by Anker et al., in *Nature Materials* 7: 442-453 (2008), which is incorporated in its entirety herein by reference.

Optionally, nano-features capable of LSPR are lithographically patterned on a planar substrate. The two dimensional patterning of nano-features has advantages in multiplexing and high-throughput analysis of a large number of different nucleic acid molecules. Optionally, gold nanoposts are substrates for surface plasmon resonance imaging detection of polymerase-template nucleic acid interactions, wherein the nucleic acids are attached to the nanoposts. Nanostructure size and period can influence surface plasmon resonance signal enhancement, optionally, providing a 2, 3, 4, 5, 6, 7, 8-fold or higher signal amplification when compared to control films.

Optionally, surface plasmon resonance may be sustained in planar surfaces. A number of commercial instruments based on the Kretschmann configuration (e.g., Biacore, Uppsala, Sweden) and surface plasmon resonance imaging (e.g., GWC Technologies; Madison, Wis.; or Horiba; Kyoto, Japan) are available and have well established protocols for attaching DNA to their surfaces, as single spots and in multiplexed array patterns. In the Kretschmann configuration, a metal film, typically gold, is evaporated onto the side of a prism and incident radiation is launched at an angle to excite the surface plasmons. An evanescent wave penetrates through the metal film exciting plasmons on the other side, where it may be used to monitor near-surface and surface interactions near the gold film. At the resonant angle, the light reflected from the prism-gold interface is severely attenuated. Assuming fixed wavelength illumination, binding interactions may be examined by monitoring both the intensity of the reflected light at a fixed angle close to the resonant angle, as well as by monitoring the changes in angle of incidence required to establish surface plasmon resonance conditions (minimum reflectivity). When a 2D imaging device such as a CCD or CMOS camera is utilized to monitor the reflected light, the entire illumination area may be imaged with high resolution. This method is called surface plasmon resonance imaging (SPRi). It allows high throughput analysis of independent regions on the surface simultaneously. Broadband illumination may also be used, in a fixed angle configuration, wherein the wavelength that is coupled to the surface plasmon resonance is identified spectroscopically by looking for dips in the reflected spectrum. Surface interactions are monitored through shifts in the resonant wavelength.

Surface plasmon resonance is a well-established method for monitoring protein-nucleic acid interactions, and there exist many standard protocols both for nucleic acid attachment as well as for analyzing the data. Illustrative references from the literature include Cho et al., "Binding Kinetics of DNA-Protein Interaction Using Surface Plasmon Resonance," *Protocol Exchange*, May 22, 2013; and Brockman et al., "A Multistep Chemical Modification Procedure To Create DNA Arrays on Gold Surfaces for the Study of Protein-DNA Interactions with Surface Plasmon Resonance Imaging," *Journal of the American Chemical Society* 121: 8044-51 (1999), both of which are incorporated by reference herein in their entireties.

Polymerase/nucleic-acid interactions may be monitored on nanostructured surfaces capable of sustaining localized surface plasmons. Optionally, polymerase/nucleic-acid interactions may be monitored on nanostructured surfaces capable of sustaining surface plasmon polaritons.

Optionally, polymerase/nucleic-acid interactions may be monitored on nanostructured surfaces capable of sustaining localized surface plasmons. Optionally, polymerase/nucleic-acid interactions may be monitored on nanostructured surfaces capable of sustaining surface plasmon polaritons.

Optionally, extraordinary optical transmission (EOT) through a nanoholes array may be used to monitor nucleic-acid/polymerase interactions. Light transmitted across sub-wavelength nanoholes in plasmonic metal films is higher than expected from classical electromagnetic theory. This enhanced optical transmission may be explained by considering plasmonic resonant coupling to the incident radiation, whereby at resonant wavelength, a larger than anticipated fraction of light is transmitted across the metallic nanoholes. The enhanced optical transmission is dependent on the dimensions and pitch of the nanoholes, properties of the metal, as well as the dielectric properties of the medium on either side of the metal film bearing the nanoholes. In the context of a biosensor, the transmissivity of the metallic nanohole array depends on the refractive index of the medium contacting the metal film, whereby, for instance, the interaction of polymerase with nucleic acid attached to the metal surface may be monitored as a change in intensity of light transmitted across the nanoholes array. Instrumentation and alignment requirements when using the EOT/plasmonic nanohole array approach of surface plasmon resonance may be employed using very compact optics and imaging elements. Low power LED illumination and a CMOS or CCD camera may suffice to implement robust EOT plasmonic sensors. An exemplary nanohole array-based surface plasmon resonance sensing device is described by Escobedo et al., in "Integrated Nanohole Array Surface Plasmon Resonance Sensing Device Using a Dual-Wavelength Source," *Journal of Micromechanics and Microengineering* 21: 115001 (2011), which is herein incorporated by reference in its entirety.

The plasmonic nanohole array may be patterned on an optically opaque layer of gold (greater than 50 nm thickness) deposited on a glass surface. Optionally, the plasmonic nanohole array may be patterned on an optically thick film of aluminum or silver deposited on glass. Optionally, the nanohole array is patterned on an optically thick metal layer deposited on low refractive index plastic. Patterning plasmonic nanohole arrays on low refractive index plastics enhances the sensitivity of the device to refractive index changes by better matching the refractive indices on the two sides of the metal layer. Optionally, refractive index sensitivity of the nanohole array is increased by increasing the distance between holes. Optionally, nanohole arrays are fabricated by replication, for example, by embossing, casting, imprint-lithography, or template-stripping. Optionally, nanohole arrays are fabricated by self-assembly using colloids. Optionally, nanohole arrays are fabricated by projection direct patterning, such as laser interference lithography.

A nano-bucket configuration may be preferable to a nanohole configuration. In the nanohole configuration, the bottom of the nano-feature is glass or plastic or other appropriate dielectric, whereas in the nano-bucket configuration, the bottom of the nano-feature includes a plasmonic metal. The nano-bucket array advantageously is relatively simple to fabricate while maintaining the transmission sensitivity to local refractive index.

Optionally, the nanohole array plasmonic sensing is combined with lens-free holographic imaging for large area imaging in an inexpensive manner. Optionally, a plasmonic biosensing platform includes a plasmonic chip with nanohole arrays, a light-emitting diode source configured to illuminate the chip, and a CMOS imager chip to record diffraction patterns of the nanoholes, which is modulated by molecular binding events on the surface. The binding events may be the formation of a closed-complex between a polymerase and a template nucleic acid in the presence of a nucleotide.

The methods to functionalize surfaces (for nucleic acid attachment) for surface plasmon resonance sensing may be directly applied to EOT nanohole arrays as both sensing schemes employ similar metal surfaces to which nucleic acids need to be attached.

Optionally, the refractive index changes associated with polymerase/nucleic acid interaction may be monitored on nanostructured surfaces that do not support plasmons. Optionally, guided mode resonance may be used to monitor the polymerase/nucleic-acid interaction. Guided-mode resonance or waveguide-mode resonance is a phenomenon wherein the guided modes of an optical waveguide can be excited and simultaneously extracted by the introduction of a phase-matching element, such as a diffraction grating or prism. Such guided modes are also called "leaky modes," as they do not remain guided and have been observed in one and two-dimensional photonic crystal slabs. Guided mode resonance may be considered a coupling of a diffracted mode to a waveguide mode of two optical structured placed adjacent or on top of each other. For instance, for a diffraction grating placed on top of an optical waveguide, one of the diffracted modes may couple exactly into the guided mode of the optical waveguide, resulting in propagation of that mode along the waveguide. For off-resonance conditions, no light is coupled into the waveguide, so the structure may appear completely transparent (if dielectric waveguides are used). At resonance, the resonant wavelength is strongly coupled into the waveguide and may be couple out of the structure depending on downstream elements from the grating-waveguide interface. In cases where the grating coupler is extended over the entire surface of the waveguide, the light cannot be guided, as any light coupled in is coupled out at the next grating element. Therefore, in a grating waveguide structure, resonance is observed as a strong reflection peak, whereas the structure is transparent to off-resonance conditions. The resonance conditions are dependent on angle, grating properties, polarization and wavelength of incident light. For cases where the guided mode propagation is not present, for instance due to a grating couple to the entire surface of the waveguide, the resonant mode may also be called leaky-mode resonance, in light of the strong optical confinement and evanescent propagation of radiation in a transverse direction from the waveguide layer. Change in dielectric properties near the grating, for instance due to binding of biomolecules affects the coupling into the waveguide, thereby altering the resonant conditions. Optionally, where nucleic acid molecules are attached to the surface of grating waveguide structures, the polymerase/nucleic-acid interaction may be monitored as a change in wavelength of the leaky mode resonance.

A diffraction element may be used directly on a transparent substrate without an explicit need for a waveguide element. The change in resonance conditions due to interactions near the grating nanostructure may be monitored as resonant wavelength shifts in the reflected or transmitted radiation.

Reflected light from a nucleic acid attached guided mode resonant sensor may be used to monitor the polymerase/nucleic-acid interaction. A broadband illumination source may be employed for illumination, and a spectroscopic examination of reflected light could reveal changes in local refractive index due to polymerase binding.

Optionally, a broadband illumination may be used and the transmitted light may be examined to identify resonant shifts due to polymerase interaction. A linearly polarized narrow band illumination may be used, and the transmitted light may be filtered through a cross-polarizer; wherein the transmitted light is completely attenuated due to the crossed polarizers excepting for the leaky mode response whose polarization is modified. This implementation converts refractive index monitoring to a simple transmission assay that may be monitored on inexpensive imaging systems. Published material describe the assembly of the optical components. See, Nazirizadeh et al., "Low-Cost Label-Free Biosensors Using Photonic Crystals Embedded between Crossed Polarizers," *Optics Express* 18: 19120-19128 (2010), which is incorporated herein by reference in its entirety.

In addition to nanostructured surfaces, plain, unstructured surfaces may also be used advantageously for monitoring refractive index modulations. Optionally, interferometry may be employed to monitor the interaction of polymerase with nucleic acid bound to an un-structured, optically transparent substrate. Nucleic acid molecules may be attached to the top surface of a glass slide by any means known in the art, and the system illuminated from the bottom surface of the glass slide. There are two reflection surfaces in this configuration, one reflection from the bottom surface of the glass slide, and the other from the top surface which has nucleic acid molecules attached to it. The two reflected waves may interfere with each other causing constructive or destructive interference based on the path length differences, with the wave reflected from the top surface modulated by the changes in dielectric constant due to the bound nucleic acid molecules (and subsequently by the interaction of polymerase with the bound nucleic acid molecules). With the reflection from the bottom surface unchanged, any binding to the nucleic acid molecules may be reflected in the phase difference between the beams reflected from the top and bottom surfaces, which in turn affects the interference pattern that is observed. Optionally, bio-layer interferometry is used to monitor the nucleic acid/polymerase interaction. Bio-layer interferometry may be performed on commercial devices such as those sold by Pall Forte Bio corporation (Menlo Park, Calif.).

Optionally, the reflected light from the top surface is selectively chosen by using focusing optics. The reflected light from the bottom surface is disregarded because it is not in the focal plane. Focusing only on the nucleic-acid-attached top surface, the light collected by the focusing lens includes a planar wave, corresponding to the partially reflected incident radiation, and a scattered wave, corresponding to the radiations scattered in the collection direction by molecules in the focal plane. These two components may be made to interfere if the incident radiation is coherent. This scattering based interferometric detection is extremely sensitive and can be used to detect down to single protein molecules.

Optionally, a field-effect transistor (FET) is configured as a biosensor for the detection of a closed-complex. A gate terminal of the FET is modified by the addition of template nucleic acids. The binding of a polymerase including a charged tag results in changes in electrochemical signals. Binding of a polymerase with a next correct nucleotide to the template nucleic acid provides different signals than polymerase binding to a template nucleic acid in the presence of other incorrect nucleotides, where each incorrect nucleotide may also provide a different signal. Optionally, polymerase interactions with a template nucleic acid are monitored using FET without the use of an exogenous label on the polymerase, primed template nucleic acid, or nucleotide. Optionally, the pH change that occurs due to release of $H^+$ ions during the incorporation reaction is detected using a FET. Optionally, the polymerase includes a tag that generates continuous $H^+$ ions that is detected by the FET. Optionally, the continuous $H^+$ ion generating tag is an ATP synthase. Optionally, the continuous $H^+$ ion generation tag is palladium, copper or another catalyst. Optionally, the release of a PPi after nucleotide incorporation is detected using FET. For example, one type of nucleotide may be provided to a reaction at a time. Once the next correct nucleotide is added and conditions allow for incorporation, PPi is cleaved, released, and detected using FET, therefore identifying the next correct nucleotide and the next base. Optionally, template nucleic acids are bound to walls of a nanotube. Optionally, a polymerase is bound to a wall of a nanotube. FET is advantageous for use as a sequencing sensor due to its small size and low weight, making it appropriate for use as a portable sequencing monitoring component. Details of FET detection of molecular interactions are described by Kim et al., in "An FET-Type Charge Sensor for Highly Sensitive Detection of DNA Sequence," *Biosensors and Bioelectronics, Microsensors and Microsystems* 20: 69-74 (2004), doi:10.1016/j.bios.2004.01.025; and by Star et al., in "Electronic Detection of Specific Protein Binding Using Nanotube FET Devices," *Nano Letters* 3: 459-63 (2003), doi:10.1021/nl0340172, which are incorporated by reference herein in their entireties.

By way of example, the polymerase includes a fluorescent tag. To monitor polymerase-nucleic acid interaction with high signal-to-noise, evanescent illumination or confocal imaging may be employed. The formation of a closed-complex on localized template nucleic acids may be observed as an increased fluorescence compared to the background, for instance, whereas in some instances it may also be observed as a decreased fluorescence due to quenching or change in local polar environment. Optionally, a fraction of polymerase molecules may be tagged with a fluorophore while another fraction may be tagged with a quencher in the same reaction mixture; wherein, the formation of closed-complex on a localized, clonal population of nucleic acid is revealed as decrease in fluorescence compared to the background. The clonal population of nucleic acids may be attached to a support surface such as a planar substrate, microparticle, or nanoparticle. Optionally, a polymerase is tagged with a fluorophore, luminophore, chemiluminophore, chromophore, or bioluminophore.

Optionally, a plurality of template nucleic acids is tethered to a surface and one (or more) dNTPs are flowed in sequentially. The spectrum of affinities reveals the identity of the next correct nucleotide and therefore the next base in the template nucleic acid. Optionally, the affinities are measured without needing to remove and replace reaction mixture conditions (i.e., a wash step). Autocorrelation of the measured intensities of the binding interaction, for instance, could readily reveal the dynamics of nucleic acid sequence. Optionally, examination includes monitoring the affinity of the polymerase to the primed template nucleic acid in the presence of nucleotides. Optionally, the polymerase binds transiently with the nucleic acid and the binding kinetics and affinity provides information about the identity of the next base on the template nucleic acid. Optionally, a closed complex is formed, wherein the reaction conditions involved in the formation of the closed complex provide information about the next base on the nucleic acid.

Any technique that can measure dynamic interactions between a polymerase and nucleic acid may be used to measure the affinities and enable the sequencing reaction methods disclosed herein.

Systems for Detecting Nucleotide-Specific Ternary Complex Formation

The provided methods can be performed using a platform, where any component of the nucleic acid polymerization reaction is localized to a surface. Optionally, the template nucleic acid is attached to a planar substrate, a nanohole array, a microparticle, or a nanoparticle. Optionally, all reaction components are freely suspended in the reaction mixture, and not immobilized to a solid support substrate.

Optionally, the template nucleic acid is immobilized to a surface. The surface may be a planar substrate, a hydrogel, a nanohole array, a microparticle, or a nanoparticle. Optionally, the reaction mixtures contain a plurality of clonally amplified template nucleic acid molecules. Optionally, the reaction mixtures contain a plurality of distinguishable template nucleic acids.

Provided herein, inter alia, are systems for performing sequencing reactions involving the examination of the interaction between a polymerase and a primed template nucleic acid in the presence of nucleotides to identify the next base in the template closed-complex by one or a combination of means including, but not limited to, crosslinking of the polymerase domains, crosslinking of the polymerase to the nucleic acid, allosteric inhibition by small molecules, uncompetitive inhibitors, competitive inhibitors, non-competitive inhibitors, and denaturation; wherein the formation of the trapped polymerase complex provides information about the identity of the next base on the nucleic acid template.

Also provided is a system for performing one or more steps of any sequencing method disclosed herein. Optionally, the system includes components and reagents necessary to perform a polymerase and template nucleic acid binding assay in the presence of nucleotides, wherein the template nucleic acid is provided on a nanostructure. Optionally, the system includes one or more reagents and instructions necessary to bind template DNA molecules onto a nanostructure. For example, the system provides a nanostructure, such as a chip, configured for use with surface plasmon resonance to determine binding kinetics. An example of such a chip is a CM5 Sensor S chip (GE Healthcare; Piscatawany, N.J.). The system may provide instrumentation such as a surface plasmon resonance instrument. The system may provide streptavidin and/or biotin. Optionally, the system provides biotin-DNA, DNA ligase, buffers, and/or DNA polymerase for preparation of biotinylated template DNA. Optionally, the system provides a gel or reagents (e.g., phenol:chloroform) for biotinylated DNA purification. Alternatively, the system provides reagents for biotinylated template DNA characterization, for example, mass spectrometry or HPLC. Optionally, the system includes streptavidin, a chip, reagents, instrumentation, and/or instructions for immobilization of streptavidin on a chip. Optionally, a chip is provided in the system already configured for template DNA coating, wherein the chip is immobilized with a reagent capable of binding template nucleic acids or modified template nucleic acids (e.g., biotinylated template DNA). Optionally, the system provides reagents for chip regeneration.

Also provided is a system for performing one or more steps of any sequencing method disclosed herein. Optionally, the system includes components and reagents necessary to perform a polymerase and template nucleic acid binding assay in the presence of nucleotides, wherein the template nucleic acid is provided on a nanoparticle. Optionally, the system includes one or more reagents and instructions necessary to bind template DNA molecules onto a nanoparticle. The nanoparticle may be configured for the electrochemical detection of nucleic acid-polymerase interaction, for instance, by using gold nanoparticles. Optionally, the DNA-nanoparticle conjugates are formed between aqueous gold colloid solutions and template DNA molecules including, for example, free thiol or disulfide groups at their ends. The conjugates may include same nucleic acid sequence. Optionally, the nanoparticle conjugates are stabilized against flocculation and precipitation at high temperature (e.g., greater than 60° C.) and high ionic strength (e.g., 1M Na$^+$). Optionally, the system provides reagents for preparing template DNA molecules for nanoparticle attachment, including, generating template DNA molecules with disulfides or thiols. Disulfide-containing template nucleic acids may be synthesized using, for example, a 3'-thiol modifier controlled-pore glass (CPG) or by beginning with a universal support CPG and adding a disulfide modifier phosphoramidite as the first monomer in the sequence. The system may provide nucleic acid synthesis reagents and/or instructions for obtaining disulfide-modified template nucleic acids. Thiol-containing template nucleic acids may also be generated during nucleic acid synthesis with a 5'-tritylthiol modifier phosphoramidite. The system may provide reagents and/or instructions for nanoparticle conjugate purification using for example, electrophoresis or centrifugation. Optionally, nanoparticle conjugates are used to monitor polymerase-template nucleic acid interactions colorimetrically. In this instance, the melting temperature of the nanoparticle conjugate increases in the presence of strong polymerase binding. Therefore, the strength of DNA binding can be determined by the change in this melting transition, which is observable by a color change. The systems optionally include reagents and equipment for detection of the melting transition.

Also provided is a system for performing one or more steps of any sequencing method disclosed herein. Optionally, the system includes components and reagents necessary to perform a polymerase and template nucleic acid binding assay in the presence of nucleotides, using a detectable polymerase. Optionally, the polymerase is detectably labeled. Optionally, the polymerase is detected using intrinsic properties of the polymerase, for example, aromatic amino acids. Optionally, the polymerase and template nucleic acids present in the system are configured for use in solution, without conjugation to a support. The detectable label on the polymerase may be a fluorophore, wherein fluorescence is used to monitor polymerase-template nucleic acid binding events. Optionally, the detectable polymerase may be used in combination with template nucleic acids in solution, or template nucleic acids conjugated to a support structure. Optionally, one or more cysteine residues of the polymerase is labeled with Cy3-maleimide. Optionally, the system includes reagents and/or instructions necessary to prepare fluorescently labeled polymerase molecules. The system may include reagents and/or instructions for purification of fluorescently labeled polymerases.

Enhancing Nucleotide Identification Using a Plurality of Nucleotides in Multiple Examination Steps The disclosed sequencing-by-binding technique can be performed using more than one nucleotide during each cycle of an examination step. For example, a single examination step optionally can be conducted using two, three, or even four different nucleotides. Optionally, each of the nucleotides is an unlabeled nucleotide, such as a native nucleotide (i.e., dATP, dGTP, dCTP, dTTP or dUTP). Preferably, a primed template nucleic acid molecule is contacted with a plurality of reaction mixtures in a serial fashion, without incorporation of any nucleotide into the primed template nucleic acid. Optionally, each different reaction mixture includes a polymerase and a different combination of two or three different nucleotides. For example, there can be four different reaction mixtures where, in aggregate, each different nucleotide (e.g., dATP, dGTP, dCTP, and dTTP) is present two times. This could be accomplished, for example, by using the following four combinations of nucleotides: (dATP and dTTP), (dATP and dGTP), (dTTP and dCTP), and (dGTP and dCTP). An alternative would be the combinations: (dGTP and dCTP), (dGTP and dTTP), (dATP and dCTP), and (dATP and dTTP). Yet another alternative would be the combinations: (dATP and dGTP), (dATP and dCTP), (dGTP and dTTP), and (dCTP and dTTP). Examination steps can be conducted using four combinations of two different nucleotides, one after the other (i.e., such that the first combination is replaced by the second combination, the second replaced by the third, and the third replaced by the fourth). When this is the case, and when monitoring of the interaction of the polymerase with the primed template nucleic acid yields a signal confirming the binding interaction, the next correct nucleotide can be identified as the nucleotide common to two different nucleotide combinations yielding positive binding signals. If it is desired to represent each different nucleotide three times among the collection of nucleotide combinations, an exemplary combination could be: (dATP and dTTP), (dATP and dGTP), (dATP and dCTP), (dTTP and dGTP), (dTTP and dCTP), and (dGTP and dCTP). Examination steps can be conducted using six combinations of two different nucleotides, one after the other (i.e., such that the first combination is replaced by the second combination, the second replaced by the third, the third replaced by the fourth, the fourth replaced by the fifth, and the fifth replaced by the sixth). When this is the case, and when monitoring of the interaction of the polymerase with the primed template nucleic acid yields a signal confirming the binding interaction, the next correct nucleotide can be identified as the nucleotide common to three different nucleotide combinations yielding a positive binding signal.

One advantage underlying use of more than one nucleotide during the examination step relates to confirmatory evidence that can be used for establishing the template sequence in the sequencing-by-binding procedure. When, for one or another reason, a single particular examination step yields only a moderate signal representing the binding interaction, testing carried out using the same nucleotide in more than one combination of nucleotides offers the opportunity for detecting the binding interaction more than once for each particular nucleotide. This enhances correct base calling by reducing the incidence of erroneously low, or false-negative results in the monitoring step.

Signal Processing Alternatives

One aspect of the disclosed technique involves identifying two of four possible nucleotides that are associated with the highest magnitude of ternary complex formation in an examination step. This can involve gathering and quantifying binding signals by any approach, and then comparing the results. For example, results from measurement of binding signals can be quantified simply by determining peak heights, where the different peaks reflect the extent of binding or interaction of the different components of the binding reaction. Of course, any standard adjustment, such as baseline subtraction, can be applied to this type of assessment. Another quantitative approach can involve integrating the area under a binding curve. The integrated values can be compared to identify the two highest values. Yet another quantitative approach can involve fitting a curve to the measured binding signal, and then projecting the curve forward to assess the point at which a plateau is reached (e.g., the point at which the first derivative of the curve reaches zero). Of course, other approaches for processing measured binding signals also can be applied to quantify binding signals, to compare the binding signals, and to identify in rank order the two highest binding signals out of four measurements (i.e., achieved using four different nucleotides). Other parameters that may be used for assessing the magnitude of ternary complex formation include peak height and/or shape of the binding curve. Still other useful parameters include calculated kinetic parameters, such as time to reach a plateau of saturation, $k_{obs}$ (i.e., the rate of ternary complex formation), or $R_{eq}$ (i.e., the maximum magnitude of the projected saturation level, where the projection involves mathematical curve fitting).

Procedural Features of the Methods

Following the examination step, where identities of the next two bases have been identified via formation of detectable complexes, the reaction conditions may be reset, recharged, or modified as appropriate, in preparation for the optional incorporation step or an additional examination step. Optionally, the identity of the next base has been identified without chemically incorporating a nucleotide. Optionally, the identity of the next base is identified with chemical incorporation of a nucleotide, wherein a subsequent nucleotide incorporation has been inhibited. Optionally, all components of the examination step, excluding the template nucleic acid being sequenced, are removed or washed away, returning the system to the pre-examination condition. Optionally, partial components of the examination step are removed. Optionally, additional components are added to the examination step.

Optionally, reversible terminator nucleotides are used in the incorporation step to ensure one, and only one nucleotide is incorporated per cycle. No labels are required on the reversible terminator nucleotides as the base identity is known from the examination step. Non-fluorescently labeled reversible terminators are readily available from commercial suppliers. Non-labeled reversible terminator nucleotides are expected to have faster incorporation kinetics compared to labeled reversible terminators due to their smaller steric footprint, and similar size to natural nucleotides.

Disclosed herein, in part, are reagent cycling sequencing methods, wherein sequencing reagents are introduced, one after another, for every cycle of examination and/or incorporation. Optionally, the sequencing reaction mixture includes a polymerase, a primed template nucleic acid, and at least one type of nucleotide. Optionally, the nucleotide and/or polymerase are introduced cyclically to the sequencing reaction mixture. Optionally, the sequencing reaction mixture includes a plurality of polymerases, primed template nucleic acids, and nucleotides. Optionally, a plurality of nucleotides and/or a plurality of polymerases are introduced cyclically to the sequencing reaction mixture. Optionally, the examination step of the sequencing reaction has a different composition than the incorporation step of the sequencing reaction.

Optionally, one or more nucleotides are sequentially added to and removed from the sequencing reaction. Optionally, 1, 2, 3, 4, or more types of nucleotides are added to and removed from the reaction mixture. For example, one type of nucleotide is added to the sequencing reaction, removed, and replaced by another type of nucleotide. Optionally, a nucleotide type present during the examination step is different from a nucleotide type present during the incorporation step. Optionally, a nucleotide type present during one examination step is different from a nucleotide type present during a sequential examination step (i.e., the sequential examination step is performed prior to an incorporation step). Optionally, 1, 2, 3, 4 or more types of nucleotides are present in the examination reaction mixture and 1, 2, 3, 4, or more types of nucleotides are present in the incorporation reaction mixture.

Optionally, a polymerase is cyclically added to and removed from the sequencing reaction. One or more different types of polymerases may be cyclically added to and removed from the sequencing reaction. Optionally, a polymerase type present during the examination step is different from a polymerase type present during the incorporation step. A polymerase type present during one examination step may be different from a polymerase type present during a sequential examination step (i.e., the sequential examination step is performed prior to an incorporation step).

Optionally, conditions such as the presence of reagents, pH, temperature, and ionic strength are varied throughout the sequencing reaction. Optionally, a metal is cyclically added to and removed from the sequencing reaction. For example, a catalytic metal ion may be absent during an examination step and present during an incorporation step. Alternatively, a polymerase inhibitor may be present during an examination step and absent during an incorporation step. Optionally, reaction components that are consumed during the sequencing reaction are supplemented with the addition of new components at any point during the sequencing reaction.

Nucleotides can be added one type at a time, with the polymerase, to a reaction condition that favors closed-complex formation. The polymerase binds only to the template nucleic acid if the next correct nucleotide is present. A wash step after every nucleotide addition ensures all excess polymerases and nucleotides not involved in a closed-complex are removed from the reaction mixture. Optionally, the wash step removes any bound polymerase and nucleotide. If the nucleotides are added one at a time, in a known order, the next base on the template nucleic acid is determined by the formation of a closed-complex when the added nucleotide is the next correct nucleotide. The closed-complex may be identified by both the conformational change and the increased stability of the polymerase-template nucleic acid-nucleotide interaction. Optionally, the stability of the closed-complex formed in the presence of the next correct nucleotide is at least an order of magnitude greater than the unstable interactions of the polymerase with the template nucleic acid in the presence of incorrect nucleotides. The use of a wash step ensures that there are no unbound nucleotides and polymerases and that the only nucleotides present in the reaction are those sequestered in a closed-complex with a polymerase and a template nucleic acid. Once the next base on the template nucleic acid is determined, the next correct nucleotide sequestered in the closed complex may be incorporated by flowing in reaction conditions that favor dissociation or destabilization of the closed-complex and extending the template nucleic acid primer strand by one base (incorporation). Therefore, the wash step ensures that the only nucleotide incorporated is the next correct nucleotide from the closed-complex. This reagent cycling method may be repeated and the nucleic acid sequence determined. This reagent cycling method may be applied to a single template nucleic acid molecule, or to collections of clonal populations such as PCR products or rolling-circle amplified DNA. Many different templates can be sequenced in parallel if they are arrayed, for instance, on a solid support. Optionally, the wash step destabilizes binary complex formation. Optionally, the washing is performed for a duration of time that ensures that the binary complex is removed, leaving the stabilized closed complex in the reaction mixture. Optionally, the wash step includes washing the reaction with a high ionic strength or a high pH solution. Optionally, the wash step destabilizes both binary and ternary complexes, removing any bound polymerase and nucleotide from an immobilized primed template nucleic acid molecule (optionally blocked at its 3'-end from forming a phosphodiester bond). Such a wash step may involve contacting immobilized complexes with a solution that includes EDTA to chelate metal ions.

Optionally, the incorporation step is a three stage process. In the first stage, all four nucleotide types are introduced into a reaction including a primed template nucleic acid, with a high fidelity polymerase, in reaction conditions which favor the formation of a closed-complex, and the next correct nucleotides are allowed to form stable closed-complexes with the template nucleic acid. In a second stage, excess nucleotides and unbound polymerase are washed away. In a third stage, reaction conditions are modified so that the closed-complex is destabilized and the sequestered nucleotides within the closed-complex become incorporated into the 3'-end of the template nucleic acid primer. In an alternative approach, the second stage is modified to remove completely any of the high fidelity polymerase and cognate nucleotide that may have been present in the closed-complex, and the removed components are then replaced with a second polymerase and one or more nucleotides (e.g., reversible terminator nucleotides). Formation of tight polymerase-nucleic acid complexes in the incorporation step can be enabled by standard techniques such as fusing a non-specific DNA binding domain to the polymerase (e.g., the Phusion polymerase, which is available from Thermo Fisher Scientific; Waltham, Mass.), and utilizing high concentrations of nucleotides to ensure correct nucleotides are always present in the closed complex.

Polymerase molecules bind to primed template nucleic acid molecules in a fingers-closed conformation in the presence of the next correct nucleotide even in the absence of divalent metal ions that are typically required for polymerase synthesis reactions. The conformational change traps the nucleotide complementary to the next template base within the active site of the polymerase. Optionally, the formation of the closed-complex may be used to determine the identity of next base on the template nucleic acid. Optionally, the primed template nucleic acids may be contacted serially by different nucleotides in the presence of polymerase, in the absence of catalytic divalent metal ions; wherein the formation of a closed complex indicates the nucleotide currently in contact with the template nucleic acid is the complementary nucleotide to the next base on the nucleic acid. A known order of nucleotides (in the presence of polymerase and absence of catalytic metal ions) brought into contact with the template nucleic acid ensures facile identification of the complementary nucleotide based on the particular position in the order that induces closed-complex formation. Optionally, an appropriate wash step may be performed after every nucleotide addition to ensure removal of all excess enzymes and nucleotides, leaving behind only the polymerase that is bound to nucleic acids in a closed-complex with the next correct nucleotide at the active site. The closed-complex may be identified by means that reveal the conformational change of the polymerase in the closed conformation or by means that reveal the increased stability of the polymerase/nucleic-acid/next-correct-nucleotide complex compared to binary polymerase-nucleic acid complexes or compared to unstable interactions between the polymerase, primed template nucleic acid and incorrect nucleotides.

Optionally, the process of identifying the next complementary nucleotide (examination step) includes the steps of contacting immobilized primed template nucleic acids with an examination mixture including polymerase and nucleotides of one kind under conditions that inhibit the chemical incorporation of the nucleotide, removing unbound reagents by a wash step, detecting the presence or absence of polymerase closed-complex on the immobilized nucleic acids, and repeating these steps serially, with nucleotides of different kinds until a closed-complex formation is detected. The closed-complex may be identified by both the conformational change and the increased stability of the polymerase/nucleic-acid/next-correct-nucleotide complex. The wash step between successive nucleotide additions may be eliminated by the use of detection mechanisms that can detect the formation of the closed complex with high fidelity, for instance, evanescent wave sensing methods or methods that selectively monitor signals from the closed-complex. The examination steps noted above may be followed by an incorporation step including, contacting the closed-complex with catalytic metal ions to covalently add the nucleotide sequestered in the closed-complex to the 3'-end of the primer. Optionally, the incorporation step may include, contacting the immobilized nucleic acids with a pre-incorporation mixture including a combination of multiple types of nucleotides and polymerase under conditions that inhibit the chemical incorporation of the nucleotides; wherein the pre-incorporation mixture may contain additives and solution conditions to ensure highly efficient closed-complex formation (e.g., low-salt conditions). The methods may also include performing a wash step to remove unbound reagents and providing the immobilized complexes with an incorporation mixture, including catalytic metal ions, to chemically incorporate nucleotides sequestered within the active site of the polymerase. The pre-incorporation mixture ensures highly efficient closed-complex formation, while the wash step and incorporation mixture ensure the addition of a single nucleotide to the 3'-end of the primer. Optionally, the incorporation step may occur directly after examination an addition of one type of nucleotide. For instance, a repeated pattern used for sequencing may include the following flow pattern (i) dATP+/polymerase, (ii) Wash, (iii) $Mg^{2+}$, (iv) Wash, (v) dTTP+/polymerase, (vi) Wash, (vii) $Mg^{2+}$, (viii) Wash, (ix) dCTP+/polymerase, (x) Wash (xi) $Mg^{2+}$, (xii) Wash, (xiii) dGTP+/polymerase, (xiv) Wash, (xv) $Mg^{2+}$, (xvi)Wash. Optionally, the repeated pattern used for sequencing may include (i) dATP+/polymerase, (ii) Wash, (iii) dTTP+/polymerase, (iv) Wash, (v) dGTP+/polymerase, (vi) Wash, (vii) dCTP+/polymerase, (viii) Wash, (ix) Pre-incorporation mixture, (x) Wash, (xi) Mg, (xii)Wash. The wash steps typically contain metal ion chelators and other small molecules to prevent accidental incorporations during the examination steps. After the incorporation step, the primer strand is typically extended by one base. Repeating this process, sequential nucleobases of a nucleic acid may be identified, effectively determining the nucleic acid sequence. Optionally, the examination step is performed at high salt conditions, for example, under conditions of 50 mM to 1,500 mM salt.

For sequencing applications, it can be advantageous to minimize or eliminate fluidics and reagents exchange. Removing pumps, valves and reagent containers can allow for simplified manufacturing of smaller devices. Disclosed herein, in part, are "all-in" sequencing methods, wherein the need to introduce reagents one after another, for every cycle of examination and/or incorporation, is eliminated. Reagents are added only once to the reaction, and sequencing-by-synthesis is performed by manipulating reagents already enclosed within the sequencing reaction. A scheme such as this requires a method to distinguish different nucleotides, a method to synchronize incorporation of nucleotides across a clonal population of nucleic acids and/or across different nucleic acid molecules, and a method to ensure only one nucleotide is added per cycle.

Optionally, the sequencing reaction mixture includes a polymerase, a primed template nucleic acid, and at least one type of nucleotide. Optionally, the sequencing reaction mixture includes a plurality of polymerases, primed template nucleic acids, and nucleotides. As provided herein, a polymerase refers to a single polymerase or a plurality of polymerases. As provided herein, a primed template nucleic acid or template nucleic acid refers to a single primed template nucleic acid or single template nucleic acid, or a plurality of primed template nucleic acids or a plurality of template nucleic acids. As provided herein, a nucleotide refers to one nucleotide or a plurality of nucleotides. As provided herein, a single nucleotide is one nucleotide. Optionally, the sequencing reaction nucleotides include, but are not limited to, 1, 2, 3, or 4 of the following nucleotides: dATP, dGTP, dCTP, dTTP, and dUTP.

Optionally, the examination step and the incorporation step take place in a single sequencing reaction mixture.

Optionally, 1, 2, 3, 4 or more types of nucleotides (e.g., dATP, dGTP, dCTP, dTTP) are present in the reaction mixture together at the same time, wherein one type of nucleotide is a next correct nucleotide. The reaction mixture further includes at least one polymerase and at least one primed template nucleic acids. Optionally, the template nucleic acid is a clonal population of template nucleic acids. Optionally, the polymerase, primed template nucleic acid, and the nucleotide form a closed-complex under examination reaction conditions.

In the provided methods, four types of nucleotides can be present at distinct and different concentrations wherein the diffusion and binding times of the polymerase to the template nucleic acid are different for each of the four nucleotides, should they be the next correct nucleotide, due to the different concentrations of the four nucleotides. For example, the nucleotide at the highest concentration would bind to its complementary base on the template nucleic acid at a fast time, and the nucleotide at the lowest concentration would bind to its complementary base on the template nucleic acid at a slower time; wherein binding to the complementary base on the template nucleic acid refers to the polymerase binding to the template nucleic acid with the next correct nucleotide in a closed closed-complex. The identity of the next correct nucleotide is therefore determined by monitoring the rate or time of binding of polymerase to the template nucleic acid in a closed-complex. Optionally, the four types of nucleotides may be distinguished by their concentration, wherein the different concentrations of the nucleotides result in measurably different on-rates for the polymerase binding to the nucleic acid. Optionally, the four types of nucleotides may be distinguished by their concentration, wherein the different concentrations of the nucleotides result in measurably different on-rates for the formation of a stabilized closed-complex.

Optionally, the polymerase is labeled. In some instances, the polymerase is not labeled (i.e., does not harbor an exogenous label, such as a fluorescent label) and any label-free detection method disclosed herein or known in the art is employed. Optionally, the binding of the polymerase to the nucleic acid is monitored via a detectable feature of the polymerase. Optionally, the formation of a stabilized closed-complex is monitored via a detectable feature of the polymerase. A detectable feature of the polymerase may include, but is not limited to, optical, electrical, thermal, colorimetric, mass, and any combination thereof.

Optionally, 1, 2, 3, 4, or more nucleotides types (e.g., dATP, dTTP, dCTP, dGTP) are tethered to 1, 2, 3, 4, or more different polymerases; wherein each nucleotide type is tethered to a different polymerase and each polymerase has a different exogenous label or a detectable feature from the other polymerases to enable its identification. All tethered nucleotide types can be added together to a sequencing reaction mixture forming a closed-complex including a tethered nucleotide-polymerase; the closed-complex is monitored to identify the polymerase, thereby identifying the next correct nucleotide to which the polymerase is tethered. The tethering may occur at the gamma phosphate of the nucleotide through a multi-phosphate group and a linker molecule. Such gamma-phosphate linking methods are standard in the art, where a fluorophore is attached to the gamma phosphate linker. Optionally, different nucleotide types are identified by distinguishable exogenous labels. Optionally, the distinguishable exogenous labels are attached to the gamma phosphate position of each nucleotide.

Optionally, the sequencing reaction mixture includes a catalytic metal ion. Optionally, the catalytic metal ion is available to react with a polymerase at any point in the sequencing reaction in a transient manner. To ensure robust sequencing, the catalytic metal ion is available for a brief period of time, allowing for a single nucleotide complementary to the next base in the template nucleic acid to be incorporated into the 3'-end of the primer during an incorporation step. In this instance, no other nucleotides, for example, the nucleotides complementary to the bases downstream of the next base in the template nucleic acid, are incorporated. Optionally, the catalytic metal ion magnesium is present as a photocaged complex (e.g., DM-Nitrophen) in the sequencing reaction mixture such that localized UV illumination releases the magnesium, making it available to the polymerase for nucleotide incorporation. Furthermore, the sequencing reaction mixture may contain EDTA, wherein the magnesium is released from the polymerase active site after catalytic nucleotide incorporation and captured by the EDTA in the sequencing reaction mixture, thereby rendering magnesium incapable of catalyzing a subsequent nucleotide incorporation.

Thus, in the provided methods, a catalytic metal ion can be present in a sequencing reaction in a chelated or caged form from which it can be released by a trigger. For example, the catalytic metal ion catalyzes the incorporation of the closed-complex next correct nucleotide, and, as the catalytic metal ion is released from the active site, it is sequestered by a second chelating or caging agent, disabling the metal ion from catalyzing a subsequent incorporation. The localized release of the catalytic metal ion from its cheating or caged complex is ensured by using a localized uncaging or un-chelating scheme, such as an evanescent wave illumination or a structured illumination. Controlled release of the catalytic metal ions may occur for example, by thermal means. Controlled release of the catalytic metal ions from their photocaged complex may be released locally near the template nucleic acid by confined optical fields, for instance by evanescent illumination such as waveguides or total internal reflection microscopy. Controlled release of the catalytic metal ions may occur for example, by altering the pH of the solution near the vicinity of the template nucleic acid. Chelating agents such as EDTA and EGTA are pH dependent. At a pH below 5, divalent cations $Mg^{2+}$ and $Mn^{2+}$ are not effectively chelated by EDTA. A method to controllably manipulate the pH near the template nucleic acid allows the controlled release of a catalytic metal ion from a chelating agent. Optionally, the local pH change is induced by applying a voltage to the surface to which the nucleic acid is attached. The pH method offers an advantage in that that metal goes back to its chelated form when the pH is reverted back to the chelating range.

Optionally, a catalytic metal ion is strongly bound to the active site of the polymerase, making it necessary to remove the polymerase from the template nucleic acid after a single nucleotide incorporation. The removal of polymerase may be accomplished by the use of a highly distributive polymerase, which falls off the 3'-end of the strand being synthesized (e.g., primer) after the addition of every nucleotide. The unbound polymerase may further be subjected to an electric or magnetic field to remove it from the vicinity of the nucleic acid molecules. Any metal ions bound to the polymerase may be sequestered by chelating agents present in the sequencing reaction mixture, or by molecules which compete with the metal ions for binding to the active site of the polymerase without disturbing the formation of the closed complex. The forces which remove or move the polymerase away from the template nucleic acid (e.g., electric field, magnetic field, and/or chelating agent) may be terminated, allowing for the polymerase to approach the template nucleic acid for another round of sequencing (i.e., examination and incorporation). The next round of sequencing, in a non-limiting example, includes the formation of a closed-complex, removing unbound polymerase away from the vicinity of the template nucleic acid and/or closed-complex, controlling the release of a catalytic metal ion to incorporate a single nucleotide sequestered within the closed-complex, removing the polymerase which dissociates from the template nucleic acid after single incorporation away from the vicinity of the template nucleic acid, sequestering any free catalytic metal ions through the use of chelating agents or competitive binders, and allowing the polymerase to approach the template nucleic acid to perform the next cycle of sequencing.

Described above are polymerase-nucleic acid binding reactions for the identification of a nucleic acid sequence. However, nucleic acid sequence identification may include information regarding nucleic acid modifications, including methylation and hydroxymethylation. Methylation may occur on cytosine bases of a template nucleic acid. DNA methylation may stably alter the expression of genes. DNA methylation is also indicated in the development of various types of cancers, atherosclerosis, and aging. DNA methylation therefore can serve as an epigenetic biomarker for human disease.

Optionally, one or more cytosine methylations on a template nucleic acid are identified during the sequencing by binding methods provided herein. The template nucleic acid may be clonally amplified prior to sequencing, wherein the amplicons include the same methylation as their template nucleic acid. Amplification of the template nucleic acids may include the use of DNA methyltransferases to achieve amplicon methylation. The template nucleic acids or amplified template nucleic acids are provided to a reaction mixture including a polymerase and one or more nucleotide types, wherein the interaction between the polymerase and nucleic acids is monitored. Optionally, the interaction between the polymerase and template nucleic acid in the presence of a methylated cytosine is different than the interaction in the presence of an unmodified cytosine. Therefore, based on examination of a polymerase-nucleic acid interaction, the identity of a modified nucleotide is determined.

Optionally, following one or more examination and/or incorporation steps, a subset of nucleotides is added to reduce or reset phasing. Thus, the methods can include one or more steps of contacting a template nucleic acid molecule being sequenced with a composition comprising a subset of nucleotides and an enzyme for incorporating the nucleotides into the strand opposite the template strand of the nucleic acid molecule. The contacting can occur under conditions to reduce phasing in the nucleic acid molecule. Optionally, the step of contacting the template nucleic acid molecule occurs after an incorporation step and/or after an examination step. Optionally, the contacting occurs after 1, 2, 3, 4, 5, 6, 7, 8, 9, 10, 15, 20, 25, 30, 35, 40, 45, 50, 60, 65, 70, 75, 80, 85, 90, 95, or 100 rounds or more of sequencing, i.e., rounds of examination and incorporation. Optionally, the contacting occurs after 30 to 60 rounds of sequencing. Optionally, the contacting occurs after every round of sequencing (i.e., after one set of examination and incorporation steps). Optionally, multiple contacting steps occur after every round of sequencing, wherein each contacting step may comprise different subsets of nucleotides. Optionally, the method further comprises one or more washing steps after contacting. Optionally, the subset comprises two or three nucleotides. Optionally, the subset comprises three nucleotides. Optionally, the subset of nucleotides is selected from three of dATP, dGTP, dCTP, dTTP or a derivative thereof. Optionally, the three nucleotides comprise adenosine, cytosine, and guanine. Optionally, the three nucleotides comprise adenosine, cytosine, and thymine. Optionally, the three nucleotides comprise cytosine, guanine and thymine. Optionally, the three nucleotides comprise adenosine, guanine and thymine. Optionally, each round of contacting comprises the same subset or different subsets of nucleotides. Optionally, sequencing of a nucleic acid template is monitored and the contacting with the subset of nucleotides occurs upon detection of phasing. See also for example, U.S. Pat. No. 8,236,532, which is incorporated herein by reference in its entirety.

Optionally, the sequencing reaction involves a plurality of template nucleic acids, polymerases and/or nucleotides, wherein a plurality of closed-complexes is monitored. Clonally amplified template nucleic acids may be sequenced together wherein the clones are localized in close proximity to allow for enhanced monitoring during sequencing. Optionally, the formation of a closed-complex ensures the synchronicity of base extension across a plurality of clonally amplified template nucleic acids. The synchronicity of base extension allows for the addition of only one base per sequencing cycle.

EXAMPLES

The following Example illustrates examination steps that employed catalytic amounts of $Mg^{2+}$ ion in combination with a primer having a 3'-blocking group. The blocking group of the primer was removed after measuring binding of the primed template nucleic acid molecule to polymerase in the presence of each different native nucleotide. The measured binding was sufficient to identify which of the nucleotides represented the cognate nucleotide for a particular position. In the next step of the workflow, a reversible terminator nucleotide was incorporated without any intervening examination step (i.e., without intervening binding, detection or identification of any nucleotide). Notably, examination and incorporation steps were carried out using two different polymerase enzymes. Optionally, a single polymerase, such as the 3PDX polymerase disclosed in U.S. Pat. No. 8,703,461 for the purpose of interrogating nucleotide analogs and incorporating reversible terminator nucleotides, also may be used.

Example 1 describes examination of a primed template nucleic acid molecule, where the primer strand was blocked from extension at its 3'-end. The examination step (i.e., involving measuring interaction between the primed template nucleic acid molecule, the polymerase, and a test nucleotide) was conducted in the presence of a catalytic metal ion with the intention of enhancing discriminatory activity of the polymerase enzyme. Results presented below demonstrated efficient identification of the next correct nucleotide, and even the following next correct nucleotide.

Example 1

Examination of a Primed Template Nucleic Acid Molecule Having a 3'-Blocked Primer in the Presence of Catalytic Concentrations of Magnesium Ion A FORTEBIO® (Menlo Park, Calif.) OCTET® instrument employing biolayer interferometry to measure binding reactions at the surface of a fiber optic tip was used in a multiwell plate format to illustrate the sequencing technique. Template strands biotinylated at their 5'-ends were used to immobilize primed template nucleic acid molecule onto fiber optic tips functionalized with streptavidin (SA) according to standard procedures. A 3'-blocked primer was prepared by incorporating a cognate reversible terminator nucleotide that included a 3'-$ONH_2$ blocking group, using Therminator DNA polymerase (New England BioLabs Inc.; Ipswich, Mass.) according to the manufacturer's instructions. A description of the reversible terminator nucleotide can be found in U.S. Pat. No. 7,544,794, the disclosure of which is incorporated by reference. Binding of incoming nucleotides was investigated using 68 units/mL of Bsu DNA polymerase (New England BioLabs Inc.; Ipswich, Mass.) in a buffer that further included 30 mM Tris (pH 8.0), 220 mM KCl, 160 mM potassium glutamate, either 0.1 mM or 1 mM $MgCl_2$, 0.01% Tween-20, and 1 mM β-mercaptoethanol. Ternary complex formation indicating cognate nucleotide binding was investigated by contacting the primed template nucleic acid molecule having the 3'-blocked primer with the Bsu DNA polymerase and one of four native dNTP nucleotides (dATP, dGTP, dCTP, and dTTP) for a period of 20 seconds in a serial fashion. Each of the different nucleotides was used at a concentration of 100 µM during the examination procedure. Thereafter, biosensors were washed with a solution that included 20 mM EDTA for 25 seconds to chelate magnesium ions. The biosensors were then equilibrated with regeneration buffer that included 30 mM Tris (pH 8.0), 220 mM KCl, 160 mM potassium glutamate, 1 mM $MgCl_2$, 0.01% Tween-20, 1 mM β-mercaptoethanol. The same steps were repeated for the remaining nucleotides in sequence until collecting all binding curves for all four dNTPs. After completing examination of the different nucleotides, and acquiring measurement data for identifying the next correct nucleotide, the biosensor was transferred into a cleavage buffer solution (1 M sodium acetate pH 5.5 and 500 mM $NaNO_2$) for 60 seconds to remove the blocking group from the 3'-end of the primer. Biosensors were next equilibrated with a regeneration buffer (20 mM Tris pH 8.0, 10 mM KCl, and 0.01% Tween-20). Correct nucleotide was subsequently incorporated using the Therminator polymerase at a concentration of 30 units/mL in a buffer that included 20 mM Tris (pH 8.8), 10 mM ammonium sulfate, 10 mM KCl, 2 mM $MgCl_2$, 0.1% Triton-X-100, and all four reversible terminator nucleotides at a concentration of 100 µM each. All buffers were prepared with HPLC grade water and the incorporation buffer included HPLC water with 0.5 wt % $OH$—$NH_2$. The incorporation step was carried out for 60 seconds, after which time the bound polymerase was washed away from the biosensor with 20 mM EDTA for 5 seconds before commencing the next examination cycle, as described above.

Figure 1B:
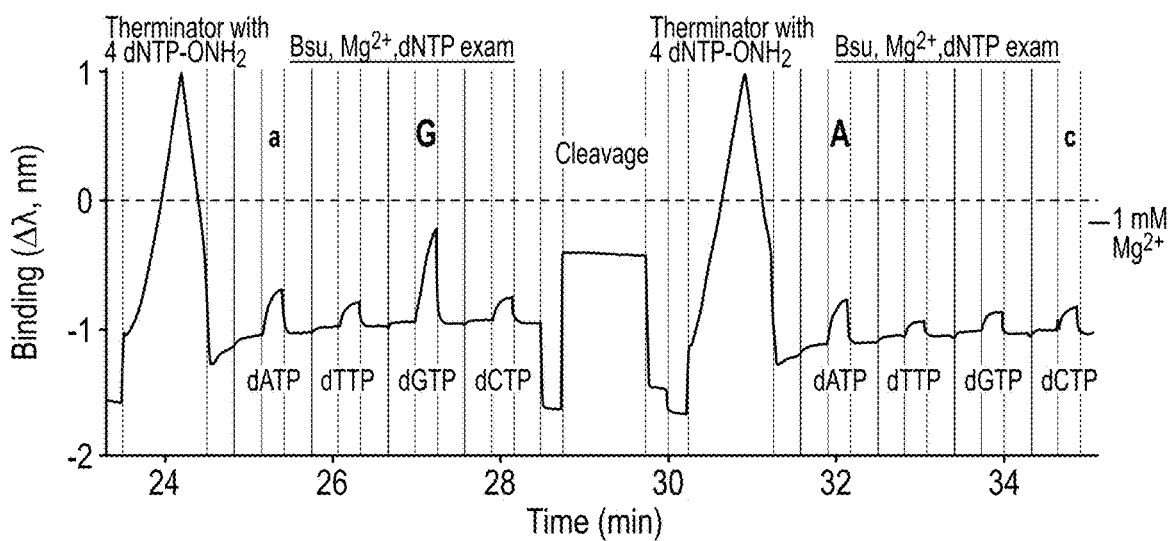

FIGS. 1A-1B show the traces for independent binding of all four nucleotides followed by the cleavage traces and incorporation traces, as discussed above. The expected base sequence in this example was GAC. As described above, a 3'-$ONH_2$ blocked primer was first formed by incorporating a reversible terminator using the Therminator polymerase. Next, for each cycle of examination the blocked primed template nucleic acid molecule was contacted with polymerase and a different nucleotide (dATP or dTTP or dGTP or dCTP) in the presence of catalytic magnesium ions for 20 seconds. High binding signals were observed if the examined nucleotide included the complementary base to the next base of the template strand. In addition to this peak, a second-high binding signal was also observed for the second correct base complementary to the second next base of the template strand. After all four nucleotides had been examined, a cleavage reaction removed the 3' blocking group from the primer. After removing the cleavage reagent with two wash steps (corresponding to the two steps with progressively reduced binding signals immediately following the cleavage step), a single incorporation reaction was carried out to add the next reversible terminator nucleotide. The procedure can be used for identifying the next correct nucleotide (next incoming nucleotide at the n+1 position), and can be repeated a plurality of times to determine the sequence of the template nucleic acid. As well, the results showed how the correct nucleotide at the n+2 position also could be determined. This observation was reproduced for all the positions in the sequence. Optionally, serial incorporation of two reversible terminators can be carried out without intervening examination steps using different types of nucleotides (i.e., other than reversible terminators) to speed the process of sequence determination.

Example 2 describes a collection of procedures that confirmed the next two correct nucleotides could be identified from a single complete cycle of examination reactions in a sequencing-by-binding protocol. More specifically, the following Example further illustrates how the next correct nucleotide, and the subsequent correct nucleotide were identified from one cycle of examining four nucleotides in a serial fashion, and then comparing the results. The use of reversible terminator nucleotides ensured that only a single nucleotide was incorporated at the end of the examination cycle.

Example 2

Examination of a Primed Template Nucleic Acid Molecule to Identify the Next Two Correct Nucleotides A FORTEBIO® (Menlo Park, Calif.) OCTET® instrument employing biolayer interferometry to measure binding reactions at the surface of a fiber optic tip was used in a multiwell plate format to illustrate the sequencing technique. Template strands biotinylated at their 5'-ends were used to immobilize primed template nucleic acid molecule onto fiber optic tips functionalized with streptavidin (SA) according to standard procedures. The primed template nucleic acid molecule was contacted for 20 seconds with 68 U/mL of Bsu DNA polymerase (New England BioLabs Inc.; Ipswich, Mass.) in a buffer that included 30 mM Tris (pH 8.0), 220 mM KCl, 160 mM potassium glutamate, 2 mM $NiSO_4$, 0.01% Tween-20, 1 mM β-mercaptoethanol, and the first incoming test nucleotide (dTTP) at a concentration of 100 µM. Thereafter, biosensors were washed with a solution that included 20 mM EDTA for 25 seconds to chelate nickel ions and remove any complexed polymerase. Biosensors were next contacted with a regeneration buffer that included 30 mM Tris (pH 8.0), 220 mM KCl, 160 mM potassium glutamate, 2 mM $NiSO_4$, 0.01% Tween-20, 1 mM β-mercaptoethanol. The same steps were repeated for the individual remaining nucleotides (dATP, dGTP, and dCTP) in sequence until collecting binding data for all four dNTPs. After completing examination of the different nucleotides, and acquiring measurement data for identifying the next correct nucleotide, the biosensor was transferred into a solution that included 20 mM EDTA for 25 seconds to chelate nickel ions and remove any complexed polymerase. The biosensors were then contacted with a buffer that included 20 mM Tris (pH 8.0), 10 mM KCl, and 0.01% Tween-20. Subsequently, a reversible terminator nucleotide was incorporated using Therminator polymerase (New England BioLabs Inc.; Ipswich, Mass.) at 30 units/mL in a buffer made 20 mM Tris (pH 8.8), 10 mM ammonium sulfate, 10 mM KCl, 2 mM $MgCl_2$, and 0.1% Triton-X-100, together with all four 3'-$ONH_2$ derivatives at concentrations of 100 µM each. All buffers were prepared with HPLC grade water and the incorporation buffer included HPLC water with 0.5 wt % $OH$—$NH_2$. The incorporation step was allowed to proceed for 60 seconds. Bound polymerase was removed from the biosensor by washing with a solution of 20 mM EDTA for 5 seconds before initiating the cleavage reaction. The incorporated reversible terminator moiety was deaminated for 60 seconds using a cleavage buffer made 1 M sodium acetate (pH 5.5) and 500 mM $NaNO_2$. The biosensor was next equilibrated with a regeneration buffer appropriate for the DNA polymerase enzyme of the examination step before commencing the next cycle. This procedure was used for examination of primed template nucleic acid molecules having free 3'-OH groups.

Figure 2:
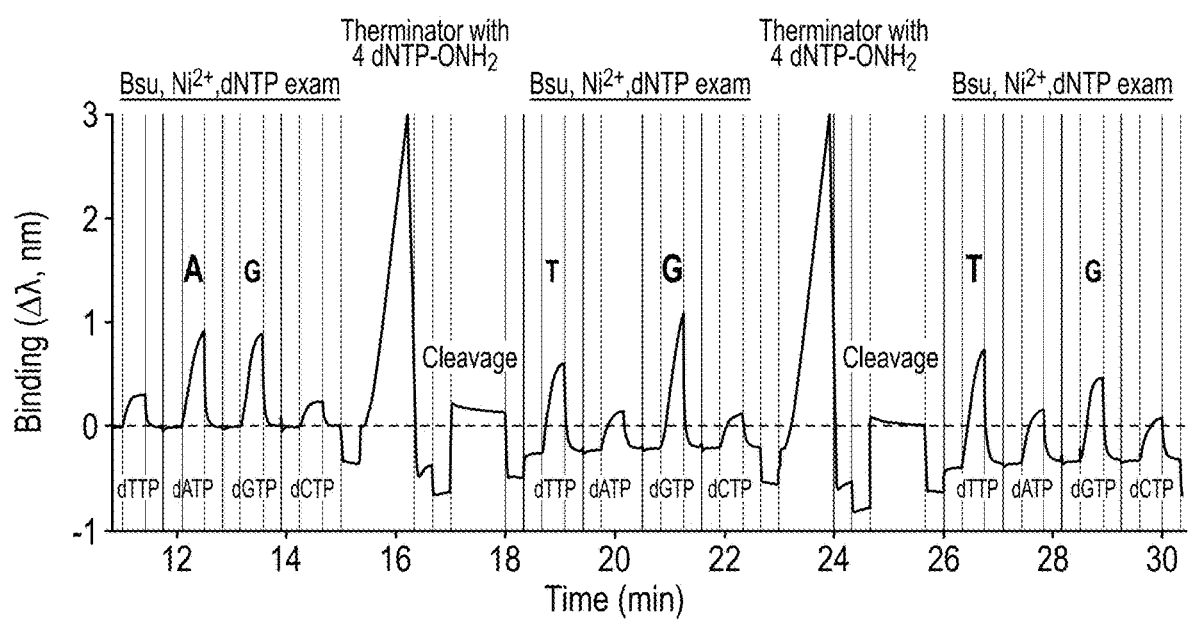
FIG. 2 is an interferometry trace for the interrogation cycles of the expected sequence (AGTG) showing all four dNTP binding signals for the same position. All examination cycles were conducted after incorporating the correct aminooxy nucleotide, and then cleaving the 3'-ONH$_2$ reversible terminator moiety to reveal an extendable 3'-OH group. The next correct incoming nucleotide (n+1) bases are highlighted in bold with a larger font size for their respective positions in the sequence. Subsequent next correct bases are highlighted in bold with smaller font size on their respective binding signal peaks. The order of examination was dTTP, dATP, dGTP, and dCTP.

FIG. 2 presents interferometry traces for serial examinations carried out using all four nucleotides, along with reversible terminator nucleotide incorporation and cleavage traces. In all instances, examination was conducted using primed template nucleic acid molecules having free 3'-OH groups. The expected sequence was AGTG. The traces illustrate two high-binding signals, where the signal indicating the most extensive ternary complex formation (e.g., as judged by highest magnitude or signal trajectory indicating a later plateau) identified the next correct nucleotide. The signal indicating the second most extensive ternary complex formation (e.g., as judged by the second highest magnitude or signal trajectory indicating a later plateau) identified the subsequent next correct nucleotide. Incorporating a single reversible terminator nucleotide extended the primer by one nucleotide. Taken together, the results presented in FIGS. 1 and 2 confirmed that the sequencing-by-binding platform was capable of identifying the next two nucleotides downstream of the primer in a primed template nucleic acid molecule.

The following Example demonstrates double incorporation of reversible terminator nucleotides, with removal of the reversible terminator moieties after each of the first and second incorporations. While the procedure described immediately below involved examination of primed template nucleic acids having free 3'-OH groups and incorporation of two reversible terminators with removal of the reversible terminator moiety before examining the next test nucleotide, variations on this procedure can be used and fall within the scope of the disclosure. For example, the order of reactions can be changed so that reversibly terminated primers are used in the examination step, with the reversible terminator moiety being cleaved from the primer after all examination reactions have been completed. Another reversible terminator nucleotide can be incorporated, its reversible terminator moiety cleaved, and then optionally yet another reversible terminator incorporated to provide a primer having a blocked 3'-end. The blocked primer can be used in the examination steps, after which the reversible terminator moiety is removed, and the next two reversible terminator nucleotides incorporated.

Example 3

Rapid Sequencing by Double Incorporation of Reversible Terminator Nucleotides

Procedures for preparing biosensors having immobilized primed template nucleic acids, for performing examination reactions in the presence of non-catalytic metal ions that inhibit polymerase-mediated incorporation, and for performing incorporation and cleavage reactions were essentially as described in Example 2. In this instance however, two reversible terminator nucleotides were incorporated, and their reversible terminator moieties removed before subsequent examination steps were conducted using native nucleotides. Magnitudes of monitored binding signals indicating complex formation were assessed simply by judging relative peak heights. Alternative assessments were based on calculating areas under the curves, kinetic trajectories leading to plateaus, etc. These approaches for assessing relative magnitudes of binding signals apply generally to the methods described herein.

Figure 3:
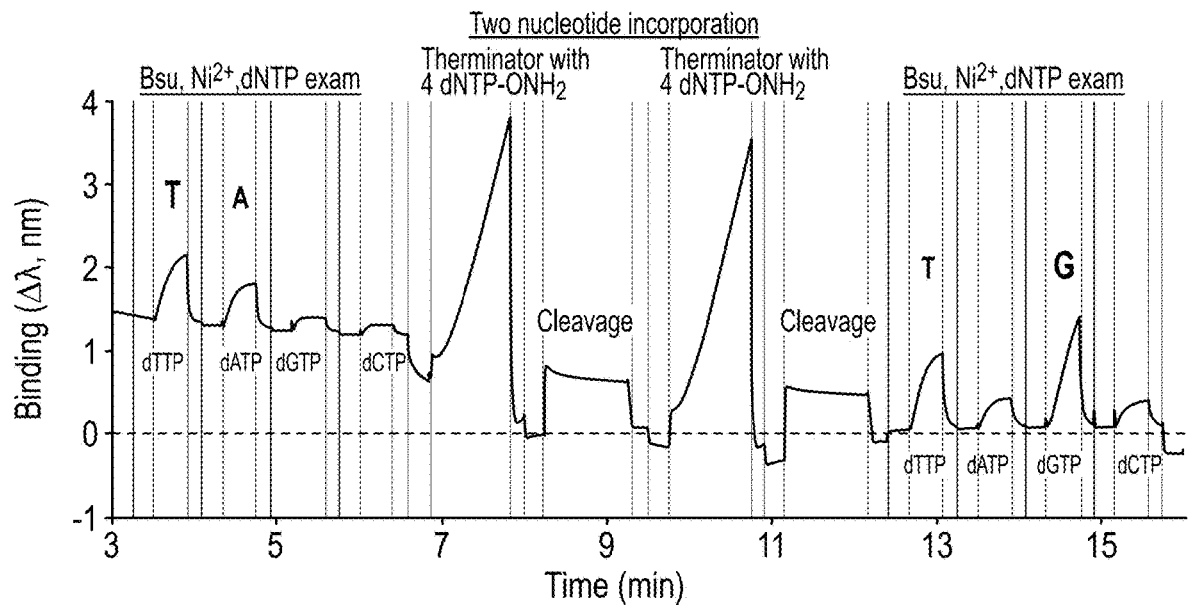
FIG. 3 is an interferometry trace for the interrogation cycles of the expected sequence (TAGT) showing all four dNTP binding signals for the same position. All interrogation cycles were conducted after incorporating two aminooxy nucleotides with their respective cleavage reactions. All the next correct incoming nucleotide (n+1) bases are highlighted in bold with larger font size for their respective positions in the sequence. Moreover, the second correct bases are highlighted in bold with smaller font size on their respective binding signal peaks in the graph. The interrogation order was dTTP, dATP, dGTP, and dCTP.

FIG. 3 presents interferometry traces for examination carried out using all four nucleotides, along with incorporation and cleavage traces obtained by examination of primed template nucleic acid molecules having free 3'-OH groups. The expected sequence was TAGT. The traces illustrate two high-binding signals, where the higher of the two signals identified the next correct nucleotide, and the second-highest binding signal identified the subsequent correct nucleotide downstream of the primer. Referring to the first set of four examination reactions, the highest binding signal indicated that the next correct nucleotide was dTTP, and the second-highest binding signal indicated the subsequent correct nucleotide was dATP. Referring to the second set of four examination reactions (i.e., following the double incorporation of reversible terminator nucleotides), the highest binding signal indicated the next correct nucleotide was dGTP, and the second-highest binding signal indicated the subsequent correct nucleotide was dTTP. Incorporating two reversible terminator nucleotides extended the primer by two nucleotides for the next round of examination.

Figure 4:
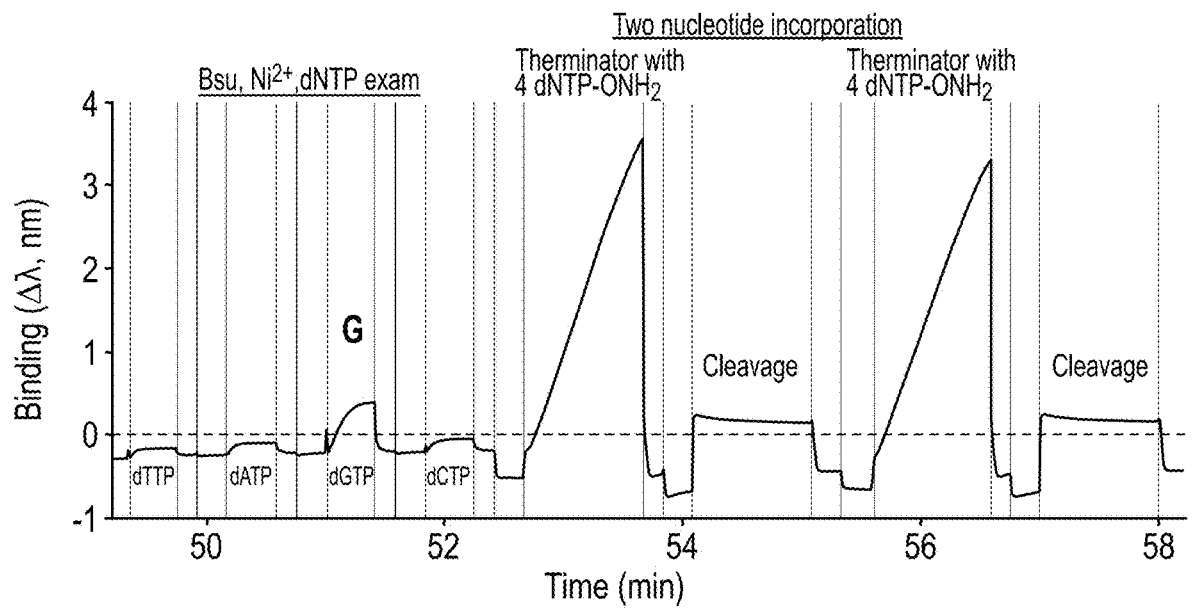
FIG. 4 is an interferometry trace for examination cycles of the expected sequence of a GG homopolymer region. The polymerase showed only one binding signal for dGTP since the sequence consisted of GG.

FIG. 4 presents interferometry traces for examination carried out using all four nucleotides, along with incorporation and cleavage traces obtained by examination of primed template nucleic acid molecules having free 3'-OH groups. The expected sequence was GGC. The traces illustrate only a single high-binding signal during the examination of dGTP. This correctly indicated that both of the next two nucleotides were the same (i.e., dGTP). Incorporating two reversible terminator nucleotides extended the primer by two nucleotides for the next round of examination.

Example 4 describes how pairwise combinations of nucleotides could be used during examination steps to increase confidence in the accuracy of base calling, and to aid in identification of the next two correct nucleotides for a primed template nucleic acid molecule. All examination reactions were carried out using nucleotide combinations, as discussed above. The demonstration included examination of one primed template nucleic acid molecule having a free 3'-OH, and another having a reversibly terminated primer.

Example 4

Examination Using Pairwise Combinations of Nucleotides

A FORTEBIO® (Menlo Park, Calif.) OCTET® instrument employing biolayer interferometry to measure binding reactions at the surface of a fiber optic tip was used in a multiwell plate format to illustrate the sequencing technique. Template strands biotinylated at their 5'-ends were used to immobilize primed template nucleic acid molecule onto fiber optic tips functionalized with streptavidin (SA) according to standard procedures. The first primed template nucleic acid molecule included a free 3'-OH group on the primer, and was examined in the presence of a non-catalytic metal ion ($Ni^{2+}$) that inhibit polymerase-mediated incorporation to stabilize ternary complexes. The second primed template nucleic acid molecule included a reversible terminator moiety (i.e., 3'-$ONH_2$) on the 3' terminal nucleotide, and was also examined in the presence of $Ni^{2+}$, although the non-catalytic metal ion is not believed necessary when using the blocked primer. The immobilized primed template nucleic acids were contacted for 20 seconds with 68 U/mL of Bsu DNA polymerase (New England BioLabs Inc.; Ipswich, Mass.) in a buffer that included 30 mM Tris (pH 8.0), 220 mM KCl, 160 mM potassium glutamate, 2 mM $NiSO_4$, 0.01% Tween-20, 1 mM β-mercaptoethanol, and the first incoming pair of test nucleotides (dATP and dGTP) at concentrations of 100 μM each. Thereafter, biosensors were washed with a solution that included 20 mM EDTA for 25 seconds to chelate nickel ions and remove any complexed polymerase. Biosensors were next contacted with a regeneration buffer that included 30 mM Tris (pH 8.0), 220 mM KCl, 160 mM potassium glutamate, 2 mM NiSO$_4$, 0.01% Tween-20, 1 mM β-mercaptoethanol. The same steps were repeated for the individual remaining pairs of nucleotides until monitoring data for binding of all four dNTPs (each being present at 100 μM concentrations) had been collected. The remaining pairs of nucleotides used in the procedure were: dATP and dCTP; dATP and dTTP; dGTP and dCTP; dTTP and dGTP; and dTTP and dCTP. After completing examination of the different nucleotide pairs, and acquiring measurement data, the biosensors were transferred into a solution that included 20 mM EDTA for 25 seconds to chelate nickel ions and remove any complexed polymerase. The biosensors were then contacted with a buffer that included 20 mM Tris (pH 8.0), 10 mM KCl, and 0.01% Tween-20. In the case where the primed template nucleic acid already included a 3'-ONH$_2$ reversible terminator moiety, that moiety was cleaved to reveal a free 3'-OH group. More specifically, the incorporated reversible terminator moiety was deaminated for 60 seconds using a cleavage buffer made of 1 M sodium acetate (pH 5.5) and 500 mM NaNO$_2$. The biosensors were then available to participate in subsequent incorporation reactions.

Figure 5A:
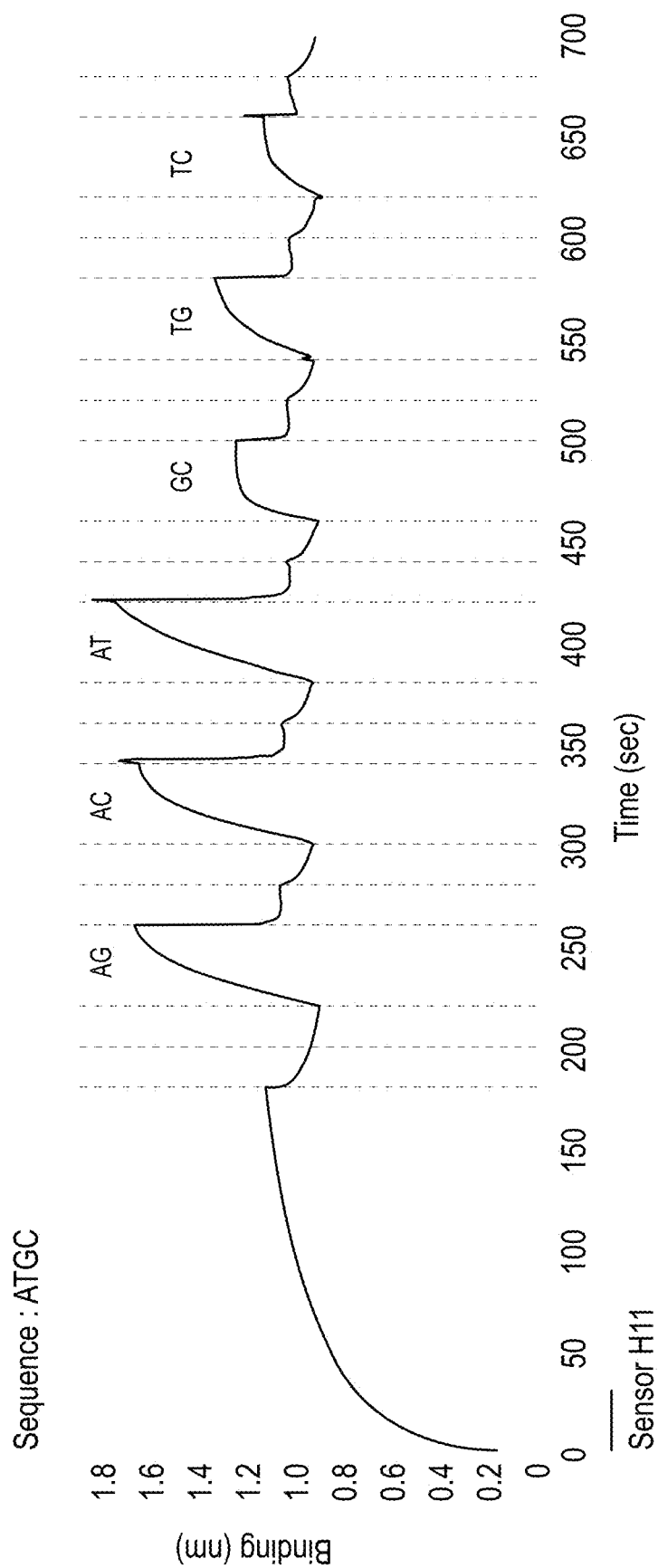
FIGS. 5A-5C are a series of graphs showing results from examination of a primed template nucleic acid (having a free 3'-OH group) using pairwise combinations of nucleotides.
Figure 5B:
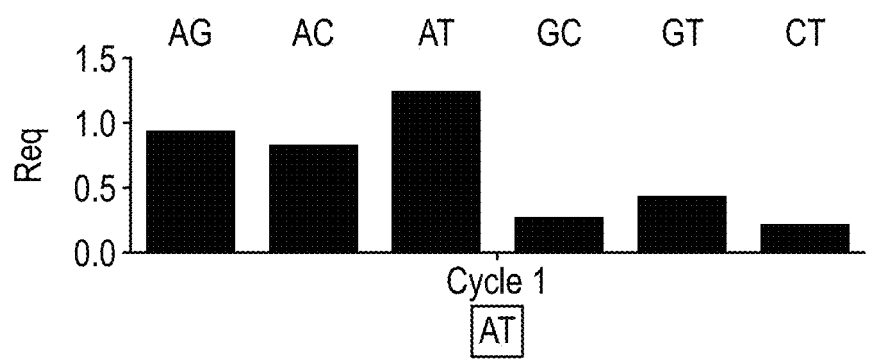
Figure 5C:
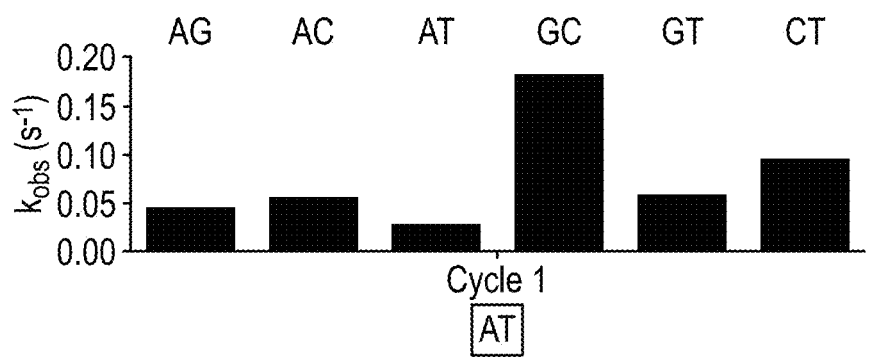

Results shown in FIGS. 5A-5C, obtained using primers terminating in free 3'-OH groups, confirmed that the next correct nucleotide, and the subsequent correct nucleotide were easily identified by using pairwise combinations of nucleotides in the examination step. FIG. 5A shows that the highest magnitudes of ternary complex formation were associated with nucleotide pairs that shared dATP, thereby indicating that this nucleotide was the next correct base. Of the three nucleotide pairs containing the first correct nucleotide (dATP), the "AT" combination (contained dATP and dTTP) yielded the highest magnitude of ternary complex formation, as judged by peak height and projected latest time to reach a plateau. Thus, dTTP was the subsequent correct nucleotide. Identity of dTTP as the correct second position was supported by the fact that the TG combination yielded a stronger signal than TC. FIGS. 5B-5C graphically present results of parameters calculated by the Octet interferometry instrument that also could be used for assessing the extent of ternary complex formation. Here the highest $R_{eq}$ values and the lowest $k_{obs}$ values indicated signal strengths in the binding assay. Again, each parameter supported determination that the next two cognate nucleotides were AT.

Figure 6A:
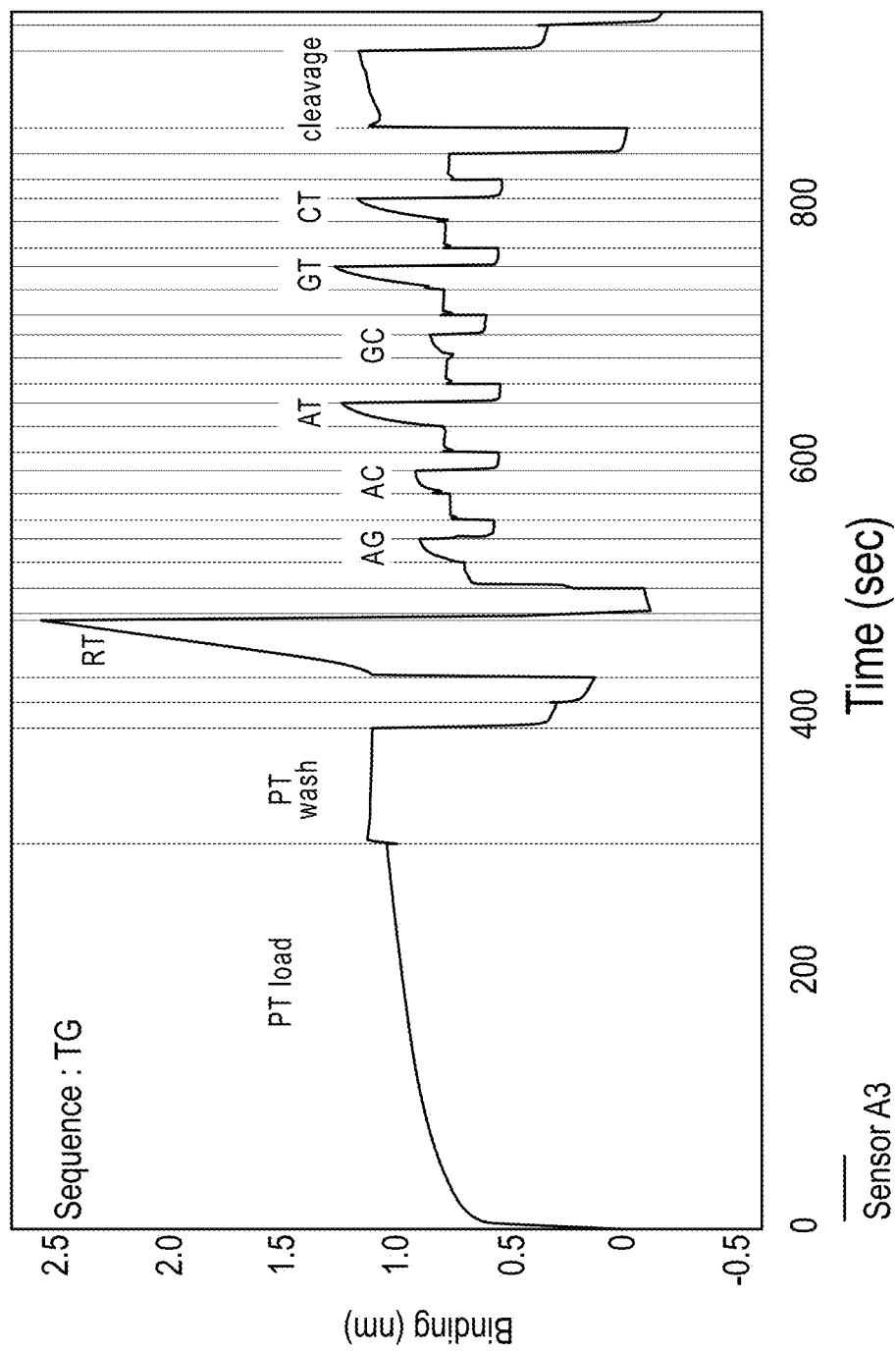
FIGS. 6A-6C are a series of graphs showing results from examination of a primed template nucleic acid (having a 3' reversibly terminated nucleotide) using pairwise combinations of nucleotides.
Figure 6B:
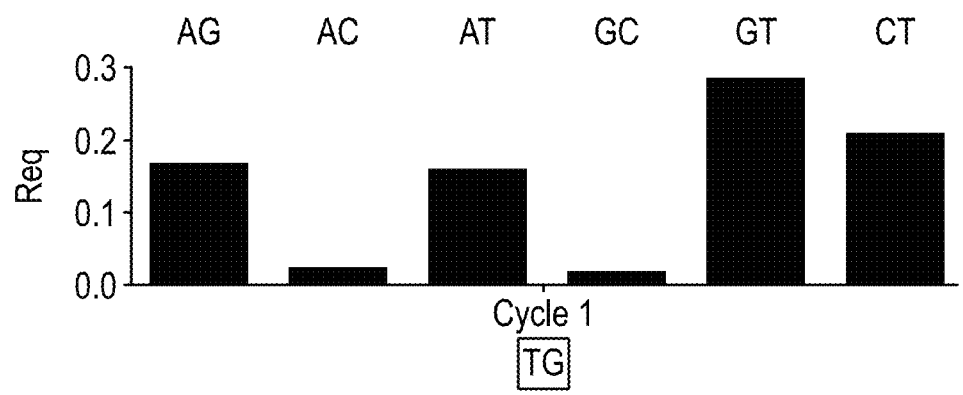
Figure 6C:
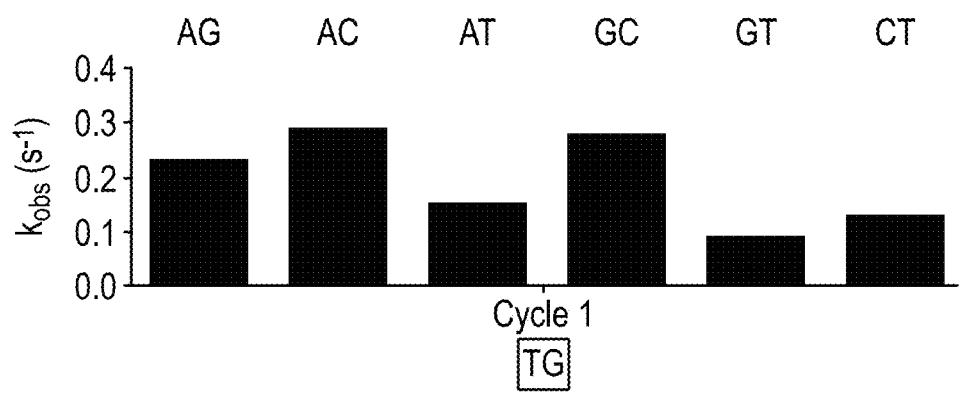

Results shown in FIGS. 6A-6C, obtained using primers reversibly blocked at their 3'-ends, further confirmed that the next correct nucleotide, and the subsequent correct nucleotide were easily identified by using pairwise combinations of nucleotides in the examination step. Again, the nucleotide pairs yielding the three highest magnitudes of ternary complex formation shared in common the presence of dTTP, thereby indicating that dTTP was the next correct nucleotide. The GT nucleotide pair yielded the highest magnitude of ternary complex formation, and so indicated the next two correct nucleotides were "TG." FIGS. 6B-6C graphically present results of parameters calculated by the Octet interferometry instrument, where the highest $R_{eq}$ values, and the lowest $k_{obs}$ values indicated signal strengths in the binding assay. Again, each parameter supported determination that the next two cognate nucleotides were TG.

Notably, very good sequencing results were obtained using a reiterative process employing: (a) examination of a primed template nucleic acid having a free 3'-OH group on the primer; (b) examination with six pairwise combinations of nucleotides, as described above; and (c) incorporation and cleavage of a reversible terminator nucleotide at the 3'-end of the primer at the conclusion of the examination step. Indeed, 47/47 nucleotides of a model template were determined correctly using essentially the procedure described in Example 4, except that the Bst polymerase was substituted in place of the Bsu polymerase. Accordingly, success of the procedure extended to multiple different DNA polymerases.

The foregoing procedures employed a plurality of examination reactions to obtain the information needed for identifying a cognate nucleotide before conducting an incorporation reaction using reversible terminator nucleotides. Generally speaking, data processing for base calling need not be contemporaneous with the examination and incorporation reactions using this approach. Optionally, base calling algorithms can employ recorded measurement data acquired during the examination steps. Further, it is to be understood that while examination and incorporation steps in the illustrated protocol used two different enzymes to demonstrate procedural flexibility, these steps optionally can be carried out using the same polymerase enzyme. Still further, the reversibly blocked primer employed in the examination step permitted use of a catalytic metal ion during that step. Optionally, however, non-catalytic metal ions that inhibit polymerase-mediated incorporation, or mixtures of non-catalytic and catalytic metal ions, can be substituted in place of the catalytic metal ions when using a primed template nucleic acid molecule having a 3'-blocked primer.

Disclosed above are materials, compositions, and components that can be used for, can be used in conjunction with, can be used in preparation for, or are products of the disclosed methods and compositions. It is to be understood that when combinations, subsets, interactions, groups, etc. of these materials are disclosed, and that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure, including steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein, and the material for which they are cited, are hereby specifically incorporated by reference in their entireties. All publications, patents, and patent applications mentioned in this specification are herein incorporated by reference to the same extent as if each individual publication, patent, or patent application was specifically and individually indicated to be incorporated by reference.

It is to be understood that the headings used herein are for organizational purposes only and are not meant to limit the description or claims.

A number of embodiments have been described. Nevertheless, it will be understood that various modifications may be made. Accordingly, other embodiments are within the scope of the claims.

What is claimed is:

1. A method of determining the identity of the next two bases of a template strand immediately downstream of a primer in a primed template nucleic acid molecule, the method comprising:
   (a) contacting a plurality of primed template nucleic acid molecules with a reaction mixture, the reaction mixture comprising a plurality of polymerases and a plurality of different test nucleotides under conditions that prevent incorporation of the test nucleotides into the plurality of primed template nucleic acid molecules;
   (b) measuring, under the conditions that prevent incorporation of the test nucleotides into the plurality of primed template nucleic acid molecules, a plurality of signals obtained from the plurality of primed template nucleic acid molecules indicating magnitudes of binding of a polymerase from the plurality of polymerases, and a test nucleotide from the plurality of different test nucleotides to the primed template nucleic acid molecules to identify for each primed template nucleic acid molecule a test nucleotide associated with the highest magnitude of binding and a test nucleotide associated with the second-highest magnitude of binding; and
   (c) determining the identity of a first correct nucleotide downstream of the primer as the test nucleotide with the highest magnitude of binding, and determining the identity of a second correct nucleotide downstream of the primer as the test nucleotide with the second highest magnitude of binding using the measured binding signals from step (b).

2. The method of claim 1, wherein step (a) comprises at least four rounds of the contacting.

3. The method of claim 1, wherein the first plurality of primed template nucleic acid molecules are blocked primed template nucleic acid molecules, and wherein the primers of the blocked primed template nucleic acid molecules comprise a reversible terminator moiety that blocks phosphodiester bond formation.

4. The method of claim 1, further comprising the step of:
   (d) incorporating a reversible terminator nucleotide comprising a reversible terminator moiety into the plurality of primed template nucleic acid molecules to produce blocked primed template nucleic acid molecules.

5. The method of claim 4, further comprising the step of:
   (e) removing the reversible terminator moieties from the blocked primed template nucleic acid molecules to produce de-blocked primed template nucleic acid molecules.

6. The method of claim 5, further comprising repeating steps (a)-(c) using the de-blocked primed template nucleic acid molecules.

7. The method of claim 5, further comprising the steps of: incorporating reversible terminator nucleotides comprising reversible terminator moieties into the de-blocked primed template nucleic acid molecules to produce a second-plurality of blocked primed template nucleic acid molecules; and
   (g) removing the reversible terminator moieties from the second plurality of blocked primed template nucleic acid molecules to produce a second plurality of de-blocked primed template nucleic acid molecules.

8. The method of claim 7, further comprising repeating steps (a)-(c) using the second plurality of de-blocked primed template nucleic acid molecules.

9. The method of claim 7, wherein step (c) occurs after all of the other steps have been performed.

10. The method of claim 1, wherein none of the different test nucleotides comprises an exogenous fluorescent labels.

11. The method of claim 1, wherein each of the different test nucleotides is a different native nucleotide.

12. The method of claim 1, wherein the polymerase does not comprise an exogenous fluorescent label, and wherein step (b) does not comprise measuring any fluorescent signal produced by the polymerase.

13. The method of claim 1, wherein the reaction mixture comprises a non-catalytic metal ion.

14. The method of claim 1, wherein the reaction mixture comprises a catalytic metal ion.

15. The method of claim 1, wherein the different test nucleotides each comprise an exogenous fluorescent label, and wherein step (b) comprises measuring fluorescent signal produced by the nucleotides.

16. The method of claim 1, wherein the polymerase comprises an exogenous fluorescent label, and wherein step (b) comprises measuring fluorescent signal produced by the polymerase.

* * * * *

UNITED STATES PATENT AND TRADEMARK OFFICE
CERTIFICATE OF CORRECTION

PATENT NO. : 11,203,779 B2  
APPLICATION NO. : 16/540825  
DATED : December 21, 2021  
INVENTOR(S) : Pinar Iyidogan et al.

Page 1 of 1

It is certified that error appears in the above-identified patent and that said Letters Patent is hereby corrected as shown below:

In the Claims

Claim 7, Column 72, Line 12:
Replace "incorporating reversible terminator nucleotides compris-" with --(f) incorporating reversible terminator nucleotides compris- --

Signed and Sealed this
Nineteenth Day of April, 2022

Katherine Kelly Vidal
*Director of the United States Patent and Trademark Office*